US008629113B2

(12) United States Patent
Lazar et al.

(10) Patent No.: US 8,629,113 B2
(45) Date of Patent: Jan. 14, 2014

(54) CTLA4-IG IMMUNOADHESINS

(71) Applicants: Gregory A. Lazar, Arcadia, CA (US); Matthew J. Bernett, Monrovia, CA (US)

(72) Inventors: Gregory A. Lazar, Arcadia, CA (US); Matthew J. Bernett, Monrovia, CA (US)

(73) Assignee: Xencor, Inc., Monrovia, CA (US)

( * ) Notice: Subject to any disclaimer, the term of this patent is extended or adjusted under 35 U.S.C. 154(b) by 0 days.

(21) Appl. No.: 13/710,305

(22) Filed: Dec. 10, 2012

(65) Prior Publication Data

US 2013/0089550 A1   Apr. 11, 2013

Related U.S. Application Data

(62) Division of application No. 13/032,491, filed on Feb. 22, 2011, now Pat. No. 8,329,867.

(60) Provisional application No. 61/412,309, filed on Nov. 10, 2010, provisional application No. 61/334,806, filed on May 14, 2010, provisional application No. 61/306,311, filed on Feb. 19, 2010.

(51) Int. Cl.
*C07K 14/00* (2006.01)

(52) U.S. Cl.
USPC .......................................................... 514/21.2

(58) Field of Classification Search
None
See application file for complete search history.

(56) References Cited

U.S. PATENT DOCUMENTS

2011/0305712 A1* 12/2011 Akamatsu et al. ......... 424/173.1

FOREIGN PATENT DOCUMENTS

WO   WO 2008/047150 A2   4/2008
WO   WO 2009/058564 A2   5/2009

OTHER PUBLICATIONS

Larsen et al. (American Journal of Transplantation, 2005; 5: 443-453).*
U.S. Appl. No. 11/124,620, filed May 5, 2005, Lazar, et al.
U.S. Appl. No. 11/256,060, filed Oct. 21, 2005, Lazar, et al.
U.S. Appl. No. 11/396,495, filed Mar. 31, 2006, Lazar, et al.
U.S. Appl. No. 11/981,606, filed Oct. 31, 2007, Lazar, et al.
U.S. Appl. No. 12/156,183, filed May 30, 2008, Chu, et al.
U.S. Appl. No. 12/341,769, filed Dec. 22, 2008, Chamberlain, et al.
U.S. Appl. No. 12/434,533, filed May 1, 2009, Alley, et al.
Alegre, M.L. et al., "T-Cell Regulation by CD28 and CTLA-4," *Nat. Rev. Immunol.* (1) 220-228 (2001).
Ashkenazi, A. and S.M. Chamow, "Immunoadhesins as Research Tools and Therapeutic Agents," *Curr. Opin. Immunol.* (9)195-200 (1997).
Bluestone, J.A. et al., "CTLA4Ig: Bridging the Basic Immunology With Clinical Application," *Immunity* (24) 233-238 (2006).
Bretscher, P.A., "A Two-Step, Two—Signal Model for the Primary Activation of Precursor Helper T-Cells," *Proc. Natl. Acad. Sci. USA*, 96:185-190 (1999).

Campbell, Christine and P. Stanley, "A Dominant Mutation to Ricin Resistance in Chinese Hamster Ovary Cells Induces UDP-GlcNAc:Glycopeptide β-4-N-Acetylglucosaminyltransferase III Activity," *J. Biol. Chem.* 261(21):13370-13378 (1984).
Chamow, S.M. and A. Ashkenazi, "Immunoadhesins: Principles and Applications," *TIBTECH* (14)52-60 (1996).
Clark, M.R., "Chemical Immunology Antibody Engineering IgG Effector Mechanisms," Dissertation submitted to Immmunology Div of Dept of Pathology, University, UK *J. Chem. Immunol.* (65) 88-110 (1997).
Collins, A., et al., "The Interaction Properties of Costimulatory Molecules Revisited," *Immunity*, 17:201-210 (2002).
Cox, K.M. et al., "Glycan optimization of a Human Monoclonal Antibody in the Aquatic Plant Lemna minor," *Nat Biotechnol* 24[12]:1591-1597 (2006).
Dall'Acqua, W.F. et al., "Increasing the Affinity A Human IgG1 for the Neonatal Fc Receptor: Biological Consequences," *J. Immunol.* (169) 5171-5180 (2002).
Dall'Acqua, W.F., et al., "Biological Consequences IgG1 for the Neonatal Fc Receptor: Increasing the Affinity of a Human," *J Biol Chem*, 281:23514-23524 (2006).
Davies, J. et al., "Expression of GnTIII in a Recombinant Anti-CD20 CHO Production Cell Line: Expression of Antibodies With Altered Glycoforms Leads to an Increase in ADCC Through Higher Affinity to FcγRIII," *Biotech and Bioeng* 74(4) 288-294 (2001).
Edelman, et al., "The Covalent Structure of an Entire yG Immunoglobulin Molecule," *Biochemistry* (62) 78-85 (1969).
Ghetie, V. and E.S. Ward, "Multiple Roles for the Major Histocompatibility Complex Class I-Related Receptor FcRn," *Annu. Rev. Immunol.* (18) 739-766 (2000).
Gorman, S.D. and M.R. Clark, "Humanisation of Monoclonal Antibodies for Therapy," *Semin Immunol*, 2[6]:457-66 (1990).
Hayhurst A. and G. Georgiou, "High-Throughput Antibody Isolation," *Curr. Opin. Chem. Biol.* (5)683-689 (2001).
Hinton, P.R. et al., "Engineering Human IgG Antibodies With Longer Serum Half-Lives in Primates," *J. Biol. Chem.*, 279(8): 6213-6216 (2004).
Hinton, P.R., et al., "An Engineered Human IgG1 Antibody with Longer Serum Half-Life," *J Immunol*, 176:346-356 (2006).
Holliger, P. et al., "Diabodies": Small bivalent and bispecific antibody fragments, *Proc Natl Acad Sci USA*, 990:6444-6448 (1993).
Holliger, P and P.J. Hudson, "Engineered Antibody Fragments and the Rise of Single Domains," *Nature Biotechnology*, 23[9]:1126-1136 (2005).
Hubbard, S.C. et al., "Synthesis and Processing of Aspargine-Linked Oligosaccharides," *Ann Rev Biochem*, 50:555-583 (1981).
Jansson, A., et al., "A Theoretical Framework for Quantitative Analysis of the Molecular Basis of Costimulation," *J. Immunol.* 175:1575-1585 (2005).
Jefferis, R. et al., "Interaction Sites on Human IgG-Fc for FcγR: Current Models," *Immunol. Lett.* 82(1): 57-65 (2002).
Kaneko, Y. et al., "Anti-Inflammatory Activity of Immunoglobulin G Resulting from Fc Sialylation," *Science*, 313:670-673 (2006).
Kim, T.D. et al., "Analysis of FcγRIII and IgG Fc Polymorphism Reveals Functional and Evolutionary Implications of Protein-Protein Interaction," *J. Mol. Evol.* (53)1-9 (2001).
Kirk, A.D., et al., "CTLA4-Ig and Anti-CD40 Ligand Prevent Renal Allograft Rejection in Primates," *Proc. Natl. Acad. Sci., USA* 94:8789-8794 (1997).
Krummel, M.F. and J.P. Allison, "CTLA-4 Engagement Inhibits IL-2 Accumulation and Cell Cycle Progression Upon Activation of Resting T Cells," *J. Exp. Med.* 182:459-465 (1995).

(Continued)

*Primary Examiner* — Ilia Ouspenski

(74) *Attorney, Agent, or Firm* — Robin M. Silva; Ada O. Wong; Morgan, Lewis & Bockius, LLP

(57) ABSTRACT

The present application relates to CTLA4-Ig immunoadhesins that target CD80 and CD86, and their use, particularly for therapeutic purposes.

23 Claims, 14 Drawing Sheets

(56) References Cited

OTHER PUBLICATIONS

Lefranc, G. et al., "Gm, Am and Km Immunoglobulin Allotypes of Two Populations in Tunisia," *Hum Genet*, 50:199-211 (1979).

Levisetti, M.G., et al., "Immunosuppresive Effects of Human CTLA4Ig in a Non-Human Primate Model of Allogenic Pancreatic Islet Transplantation," J. Immunol., 159: 5187-5191 (1997).

Li, H. et al., "Optimization of Humanized IgGs in Glycoengineered *Pichia pastoris,*" *Nature Biotechnol*, 24[2]:210-215 (2006).

Liu, C.C. and P.G. Schultz, "Adding New Chemistries to the Genetic Code," *Annu Rev Biochem*, 79:413-444 (2010).

Maynard, J. and G. Georgiou, "Antibody Engineering," *Annu Rev Biomed Eng*, 2:339-376 (2000).

Mechetina, L.V., et al., "Identification of CD16-2, a novel mouse receptor homologous to CD16/FcγRIII," *Immunogenetics*, 54:463-468 (2002).

Nechansky, A. et al., "Compensation of endogenous IgG mediated inhibition of antibody-dependent cellular cytotoxicity by glycol-engineering of therapeutic antibodies," *Mol Immunol*, 44[7]:1815-1817 (2007).

Pierce Chemical Company catalog, technical section on cross-linkers, pp. 155-200, 1994 (2009 version provided, pp. 1-45).

Poljak, R.J. et al., "Production and Structure of Diabodies," *Structure*, 2:1121-1123 (1994).

Raghavan, M. And P.J. Bjorkman, "Fc Receptors and Their Interactions With Immunoglobulins," *Annu. Rev. Cell Dev. Biol.* (12) 181-220 (1996).

Ravetch, J.V. and S. Bolland, "IgG Fc Receptors," *Annu. Rev. Immunol.* (19) 275-290 (2001).

Sakaguchi, S., et al., "Regulatory T-Cells: How Do They Suppress Immune Responses?" *Int'l Journal Immunol.* 21(10):1105-1111 (2009).

Scallon, B.J. et al., "Higher levels of sialylated Fc gylcans in immunoglobulin G molecules can adversely impact functionality," *Mol Immunol*, 44[7]:1524-1534 (2007).

Shields, R.L. et al., "High Resolution Mapping of the Binding Site on Human IgG1 for FcγRI, FcγRIII and FcRn and Design of IgG1 Variants With Improved Binding to the FcγR," *J. Biol. Chem.* 276(9) 6591-6604 (2001).

Shields, R.L. et al.,"Lack of Fucose on Human IgG1 N-Linked Oligosaccharide Improves Binding to Human FcγRIII and Antibody-Dependent Cellular Toxicity," *J. Biol. Chem.* 277(30) 26733-26740 (2002).

Shinkawa, T. et al., "The Absence of Fucose but Not the Presence of Galactose or Bisecting *N*-Acetylglucosamine of Human IgG1 Complex-Type Oligosaccharides Shows the Critical Role of Enhancing Antibody-Dependent Cellular Cytotoxicity," *J. Biol. Chem.* 278(5) 3466-3473 (2003).

Strohl, W.R., "Optimization of Fc-mediated Effector Functions of Monoclonal Antibodies," *Curr Opin. in Biotechnology*, 20:1-7 (2009).

Trail, P. and A.B. Bianchi, "Monoclonal Antibody Drug Conjugates in the Treatment of Cancer," *Curr. Opin. Immunol.* (11) 584-588 (1999).

Umana, P. et al., "Engineered Glycoforms of an Antineuro-Blastoma IgG1 With Optimized Antibody-Dependent Cellular Cytotoxicity Activity," *Nature* (17) 176-180 (1999).

Van Loghem E., "Allotypic Markers," *Monogr. Allergy* 19:40-51 (1986).

Walunas, T.L., et al., "CTLA-4 Can Function as a Negative Regulator of T Cell Activation," *Immunity* (1):405-413 (1994).

Who Review of the Notation for the Allotypic and Related Markers of Human Immunogolobulins, *J. Immunogen* (3) 357-362 (1976).

Who Review of the Notation for the Allotypic and Related Markers of Human Immunoglobulins, *Eur. J. Immunol.* (6) 599-601 (1976).

Yeung, Y.A. et al., "Engineering Human IgG1 Affinity to Human Neonatal Fc Receptor: Impact of Affinity Improvement on Parmakokinetics in Primates," *J Immunol*, 182:7663-7671 (2010).

\* cited by examiner

Figure 1

Human CTLA4 (SEQ ID NO: 5)

MACLGFQRHKAQLNLATRTWPCTLLFFLLFIPVFCKAMHVAQPAVVLASSRGIASFVCEYAS
PGKATEVRVTVLRQADSQVTEVCAATYMMGNELTFLDDSICTGTSSGNQVNLTIQGLRAMD
TGLYICKVELMYPPPYYLGIGNGTQIYVIDPEPCPDSDFLLWILAAVSSGLFFYSFLLTAVSLS
KMLKKRSPLTTGVYVKMPPTEPECEKQFQPYFIPIN

Human CTLA4 ECD (Sequential numbering 1-124) (SEQ ID NO: 6)

MHVAQPAVVLASSRGIASFVCEYASPGKATEVRVTVLRQADSQVTEVCAATYMMGNELTF
LDDSICTGTSSGNQVNLTIQGLRAMDTGLYICKVELMYPPPYYLGIGNGTQIYVIDPEPCPDS
D

Belatacept CTLA4(29Y/104E) (Sequential numbering 1-124) (SEQ ID NO: 7)

MHVAQPAVVLASSRGIASFVCEYASPGKYTEVRVTVLRQADSQVTEVCAATYMMGNELTF
LDDSICTGTSSGNQVNLTIQGLRAMDTGLYICKVELMYPPPYYEGIGNGTQIYVIDPEPCPDS
D

Consensus sequence (Sequential numbering 1-124) (SEQ ID NO: 8)

MHVAQPAVVLASSRGIASFVCEYASPGK(A/H)TEVRVTVLRQADSQVTEVCAA(T/N)Y(M/Y)
MGNELTF(L/E)DDSICTGTSSGNQVNLTIQGLRAMDTGLYIC(K/Q)VELMYPPPYYLGIGNGT
QIYVIDPEPCPDSD

Bolded amino acids means that either amino acid residue can be found at the position.

Figure 2

Fc(IgG1) (EU numbering 230-447) (SEQ ID NO: 9)
PAPELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPQVYTL
PPSRDELTKNQVSLTCLVKGFYPSDIAVEWESNGQPENNYKTTPPVLDSDGSFFLYSKLTV
DKSRWQQGNVFSCSVMHEALHNHYTQKSLSLSPGK Fc(IgG2) (EU numbering 230-447) (SEQ ID NO: 10)
PAPPVAGPSVFLFPPKPKDTLMISRTPEVTCVVVDVSHEDPEVQFNWYVDGVEVHNAKTKP
REEQFNSTFRVVSVLTVVHQDWLNGKEYKCKVSNKGLPAPIEKTISKTKGQPREPQVYTLP
PSREEMTKNQVSLTCLVKGFYPSDIAVEWESNGQPENNYKTTPPMLDSDGSFFLYSKLTVD
KSRWQQGNVFSCSVMHEALHNHYTQKSLSLSPGK Fc(IgG3) (EU numbering 230-447) (SEQ ID NO: 11)
PAPELLGGPSVFLFPPKPKDTLMISRTPEVTCVVVDVSHEDPEVQFKWYVDGVEVHNAKTK
PREEQYNSTFRVVSVLTVLHQDWLNGKEYKCKVSNKALPAPIEKTISKTKGQPREPQVYTL
PPSREEMTKNQVSLTCLVKGFYPSDIAVEWESSGQPENNYNTTPPMLDSDGSFFLYSKLTV
DKSRWQQGNIFSCSVMHEALHNRFTQKSLSLSPGK Fc(IgG4) (EU numbering 230-447) (SEQ ID NO: 12)
PAPEFLGGPSVFLFPPKPKDTLMISRTPEVTCVVVDVSQEDPEVQFNWYVDGVEVHNAKTK
PREEQFNSTYRVVSVLTVLHQDWLNGKEYKCKVSNKGLPSSIEKTISKAKGQPREPQVYTL
PPSQEEMTKNQVSLTCLVKGFYPSDIAVEWESNGQPENNYKTTPPVLDSDGSFFLYSRLTV
DKSRWQEGNVFSCSVMHEALHNHYTQKSLSLSLGK Fc(IgG1-238S) (aka abatacept Fc) (EU numbering 230-447) (SEQ ID NO: 13)
PAPELLGGSSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPQVYTL
PPSRDELTKNQVSLTCLVKGFYPSDIAVEWESNGQPENNYKTTPPVLDSDGSFFLYSKLTV
DKSRWQQGNVFSCSVMHEALHNHYTQKSLSLSPGK Fc(IgG2-233E/234L/235L/236G) (EU numbering 230-447) (SEQ ID NO: 14)
PAPELLGGPSVFLFPPKPKDTLMISRTPEVTCVVVDVSHEDPEVQFNWYVDGVEVHNAKTK
PREEQFNSTFRVVSVLTVVHQDWLNGKEYKCKVSNKGLPAPIEKTISKTKGQPREPQVYTL
PPSREEMTKNQVSLTCLVKGFYPSDIAVEWESNGQPENNYKTTPPMLDSDGSFFLYSKLTV
DKSRWQQGNVFSCSVMHEALHNHYTQKSLSLSPGK Fc(IgG2-233E/234L/235L/236G/238S) (EU numbering 230-447) (SEQ ID NO:15)
PAPELLGGSSVFLFPPKPKDTLMISRTPEVTCVVVDVSHEDPEVQFNWYVDGVEVHNAKTK
PREEQFNSTFRVVSVLTVVHQDWLNGKEYKCKVSNKGLPAPIEKTISKTKGQPREPQVYTL
PPSREEMTKNQVSLTCLVKGFYPSDIAVEWESNGQPENNYKTTPPMLDSDGSFFLYSKLTV
DKSRWQQGNVFSCSVMHEALHNHYTQKSLSLSPGK

Figure 3

Linker(IgG1) (EU numbering 216-229) (SEQ ID NO: 16)

EPKSCDKTHTCPPC

Linker(IgG2) (EU numbering 216-229) (SEQ ID NO: 17)

ERKCCVECPPC

Linker(IgG3) (EU numbering 216-229) (SEQ ID NO: 18)

ELKTPLGDTTHTCPRCPEPKSCDTPPPCPRCPEPKSCDTPPPCPRCPEPKSCDTPPPCPRC

Linker(IgG4) (EU numbering 216-229) (SEQ ID NO: 19)

ESKYGPPCPSC

Linker(IgG1-220S/226S/229S) (EU numbering 216-229) (SEQ ID NO: 20)

EPKSSDKTHTSPPS

Linker(IgG2-219S/220S/226S/229S) (SEQ ID NO: 21)

ERKSSVESPPS

Linker(Q-IgG1-220S/226S/229S) (aka abatacept linker) (SEQ ID NO: 22)

QEPKSSDKTHTSPPS

Linker(Q-IgG2-219S/220S/226S/229S) (SEQ ID NO: 23)

QERKSSVESPPS

Figure 4

Ig(ab) [Linker(Q-IgG1-220S/226S/229S)+Fc(IgG1-238S)] (SEQ ID NO: 24)

QEPKSSDKTHTSPPSPAPELLGGSSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIEKTI
SKAKGQPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPGK

Ig(ab-238P) [Linker(Q-IgG1-220S/226S/229S)+Fc(IgG1)] (SEQ ID NO: 25)

QEPKSSDKTHTSPPSPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIEKTI
SKAKGQPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPGK

Ig(G2) [Linker(Q-IgG2-219S/220S/226S/229S)+Fc(IgG2)] (SEQ ID NO: 26)

QERKSSVESPPSPAPPVAGPSVFLFPPKPKDTLMISRTPEVTCVVVDVSHEDPEVQFNWYV
DGVEVHNAKTKPREEQFNSTFRVVSVLTVVHQDWLNGKEYKCKVSNKGLPAPIEKTISKTK
GQPREPQVYTLPPSREEMTKNQVSLTCLVKGFYPSDIAVEWESNGQPENNYKTTPPMLDS
DGSFFLYSKLTVDKSRWQQGNVFSCSVMHEALHNHYTQKSLSLSPGK

Ig(G2-ELLG) [Linker(Q-IgG1-220S/226S/229S)+Fc(IgG2-233E/234L/235L/236G)] (SEQ ID NO: 27)

QEPKSSDKTHTSPPSPAPELLGGPSVFLFPPKPKDTLMISRTPEVTCVVVDVSHEDPEVQF
NWYVDGVEVHNAKTKPREEQFNSTFRVVSVLTVVHQDWLNGKEYKCKVSNKGLPAPIEKTI
SKTKGQPREPQVYTLPPSREEMTKNQVSLTCLVKGFYPSDIAVEWESNGQPENNYKTTPP
MLDSDGSFFLYSKLTVDKSRWQQGNVFSCSVMHEALHNHYTQKSLSLSPGK

Figure 5

Abatacept CTLA4-Ig(ab) (XENP8420) (SEQ ID NO: 28)

MHVAQPAVVLASSRGIASFVCEYASPGKATEVRVTVLRQADSQVTEVCAATYMMGNELTF
LDDSICTGTSSGNQVNLTIQGLRAMDTGLYICKVELMYPPPYYLGIGNGTQIYVIDPEPCPDS
DQEPKSSDKTHTSPPSPAPELLGGSSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIEK
TISKAKGQPREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPGK

CTLA4-Ig(G2) (XENP8445) (SEQ ID NO: 29)

MHVAQPAVVLASSRGIASFVCEYASPGKATEVRVTVLRQADSQVTEVCAATYMMGNELTF
LDDSICTGTSSGNQVNLTIQGLRAMDTGLYICKVELMYPPPYYLGIGNGTQIYVIDPEPCPDS
DQERKSSVESPPSPAPPVAGPSVFLFPPKPKDTLMISRTPEVTCVVVDVSHEDPEVQFNWY
VDGVEVHNAKTKPREEQFNSTFRVVSVLTVVHQDWLNGKEYKCKVSNKGLPAPIEKTISKT
KGQPREPQVYTLPPSREEMTKNQVSLTCLVKGFYPSDIAVEWESNGQPENNYKTTPPMLD
SDGSFFLYSKLTVDKSRWQQGNVFSCSVMHEALHNHYTQKSLSLSPGK

Belatacept CTLA4(29Y/104E)-Ig(ab) (XENP8448) (SEQ ID NO: 30)

MHVAQPAVVLASSRGIASFVCEYASPGKYTEVRVTVLRQADSQVTEVCAATYMMGNELTF
LDDSICTGTSSGNQVNLTIQGLRAMDTGLYICKVELMYPPPYYEGIGNGTQIYVIDPEPCPDS
DQEPKSSDKTHTSPPSPAPELLGGSSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIEK
TISKAKGQPREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPGK

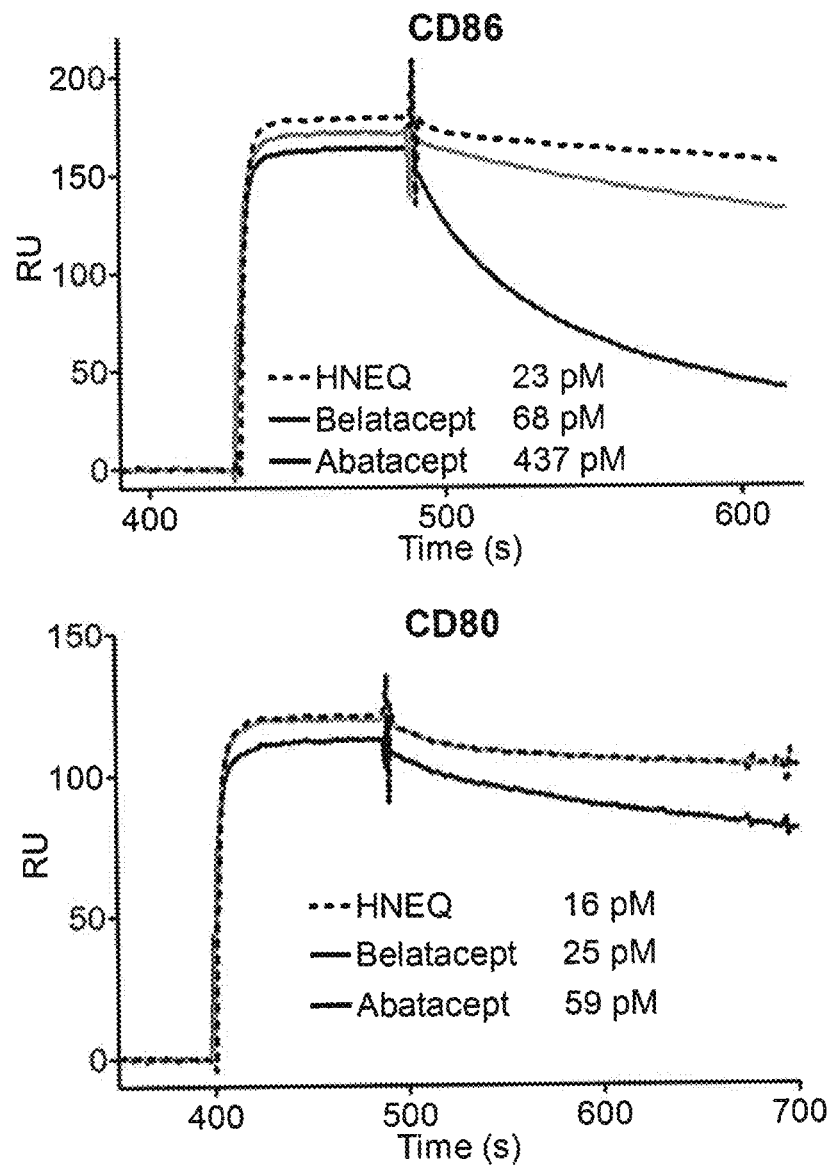

Figure 9

CTLA4(HNEQ) (29H/51N/61E/93Q) (H1.135) (SEQ ID NO: 31)

MHVAQPAVVLASSRGIASFVCEYASPGKHTEVRVTVLRQADSQVTEVCAANYMMGNELTF
EDDSICTGTSSGNQVNLTIQGLRAMDTGLYICQVELMYPPPYYLGIGNGTQIYVIDPEPCPD
SD

CTLA4(NEQ) (51N/61E/93Q) (H1.144) (SEQ ID NO: 32)

MHVAQPAVVLASSRGIASFVCEYASPGKATEVRVTVLRQADSQVTEVCAANYMMGNELTF
EDDSICTGTSSGNQVNLTIQGLRAMDTGLYICQVELMYPPPYYLGIGNGTQIYVIDPEPCPD
SD

CTLA4(HNEQ)-Ig(ab) (XENP9360) (SEQ ID NO: 33)

MHVAQPAVVLASSRGIASFVCEYASPGKHTEVRVTVLRQADSQVTEVCAANYMMGNELTF
EDDSICTGTSSGNQVNLTIQGLRAMDTGLYICQVELMYPPPYYLGIGNGTQIYVIDPEPCPD
SDQEPKSSDKTHTSPPSPAPELLGGSSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNYKTT
PPVLDSDGSFFLYSKLTVDKSRWQQGNVFSCSVMHEALHNHYTQKSLSLSPGK

CTLA4(NEQ)-Ig(ab) (XENP9369) (SEQ ID NO: 34)

MHVAQPAVVLASSRGIASFVCEYASPGKATEVRVTVLRQADSQVTEVCAANYMMGNELTF
EDDSICTGTSSGNQVNLTIQGLRAMDTGLYICQVELMYPPPYYLGIGNGTQIYVIDPEPCPD
SDQEPKSSDKTHTSPPSPAPELLGGSSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNYKTT
PPVLDSDGSFFLYSKLTVDKSRWQQGNVFSCSVMHEALHNHYTQKSLSLSPGK

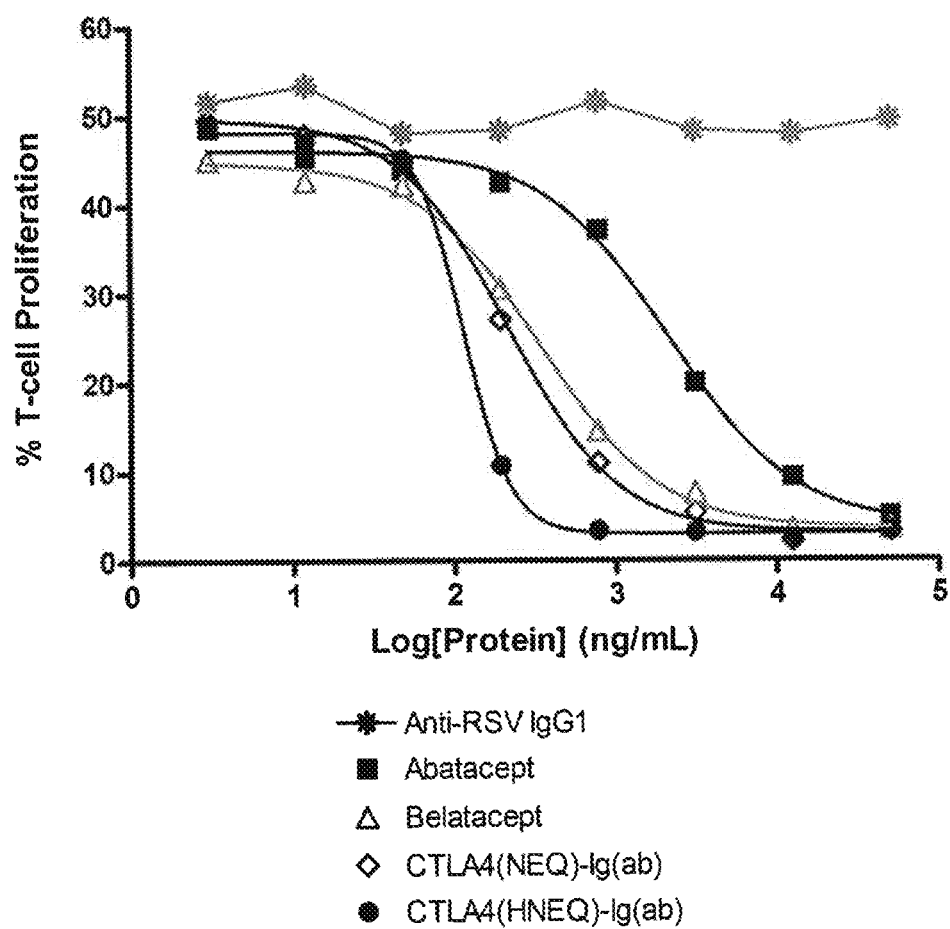

Figure 11

Abatacept CTLA4-Ig(ab-428L/434S) (XENP8441) (SEQ ID NO: 35)

MHVAQPAVVLASSRGIASFVCEYASPGKATEVRVTVLRQADSQVTEVCAATYMMGNELTF
LDDSICTGTSSGNQVNLTIQGLRAMDTGLYICKVELMYPPPYYLGIGNGTQIYVIDPEPCPDS
DQEPKSSDKTHTSPPSPAPELLGGSSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIEK
TISKAKGQPREPQVYTLPPSRDELTKNQVSLTCLVKGFYPSDIAVEWESNGQPENNYKTTP
PVLDSDGSFFLYSKLTVDKSRWQQGNVFSCSVLHEALHSHYTQKSLSLSPGK

CTLA4-Ig(G2-428L/434S) (XENP8447) (SEQ ID NO: 36)

MHVAQPAVVLASSRGIASFVCEYASPGKATEVRVTVLRQADSQVTEVCAATYMMGNELTF
LDDSICTGTSSGNQVNLTIQGLRAMDTGLYICKVELMYPPPYYLGIGNGTQIYVIDPEPCPDS
DQERKSSVESPPSPAPPVAGPSVFLFPPKPKDTLMISRTPEVTCVVVDVSHEDPEVQFNWY
VDGVEVHNAKTKPREEQFNSTFRVVSVLTVVHQDWLNGKEYKCKVSNKGLPAPIEKTISKT
KGQPREPQVYTLPPSREEMTKNQVSLTCLVKGFYPSDIAVEWESNGQPENNYKTTPPMLD
SDGSFFLYSKLTVDKSRWQQGNVFSCSVLHEALHSHYTQKSLSLSPGK

CTLA4(HNEQ)-Ig(G2-ELLG-428L/434S) (XENP9523) (SEQ ID NO: 37)

MHVAQPAVVLASSRGIASFVCEYASPGKHTEVRVTVLRQADSQVTEVCAANYMMGNELTF
EDDSICTGTSSGNQVNLTIQGLRAMDTGLYICQVELMYPPPYYLGIGNGTQIYVIDPEPCPD
SDQEPKSSDKTHTSPPSPAPELLGGPSVFLFPPKPKDTLMISRTPEVTCVVVDVSHEDPEV
QFNWYVDGVEVHNAKTKPREEQFNSTFRVVSVLTVVHQDWLNGKEYKCKVSNKGLPAPIE
KTISKTKGQPREPQVYTLPPSREEMTKNQVSLTCLVKGFYPSDIAVEWESNGQPENNYKTT
PPMLDSDGSFFLYSKLTVDKSRWQQGNVFSCSVLHEALHSHYTQKSLSLSPGK

CTLA4(NEQ)-Ig(G2-ELLG-428L/434S) (XENP9524) (SEQ ID NO: 38)

MHVAQPAVVLASSRGIASFVCEYASPGKATEVRVTVLRQADSQVTEVCAANYMMGNELTF
EDDSICTGTSSGNQVNLTIQGLRAMDTGLYICQVELMYPPPYYLGIGNGTQIYVIDPEPCPD
SDQEPKSSDKTHTSPPSPAPELLGGPSVFLFPPKPKDTLMISRTPEVTCVVVDVSHEDPEV
QFNWYVDGVEVHNAKTKPREEQFNSTFRVVSVLTVVHQDWLNGKEYKCKVSNKGLPAPIE
KTISKTKGQPREPQVYTLPPSREEMTKNQVSLTCLVKGFYPSDIAVEWESNGQPENNYKTT
PPMLDSDGSFFLYSKLTVDKSRWQQGNVFSCSVLHEALHSHYTQKSLSLSPGK

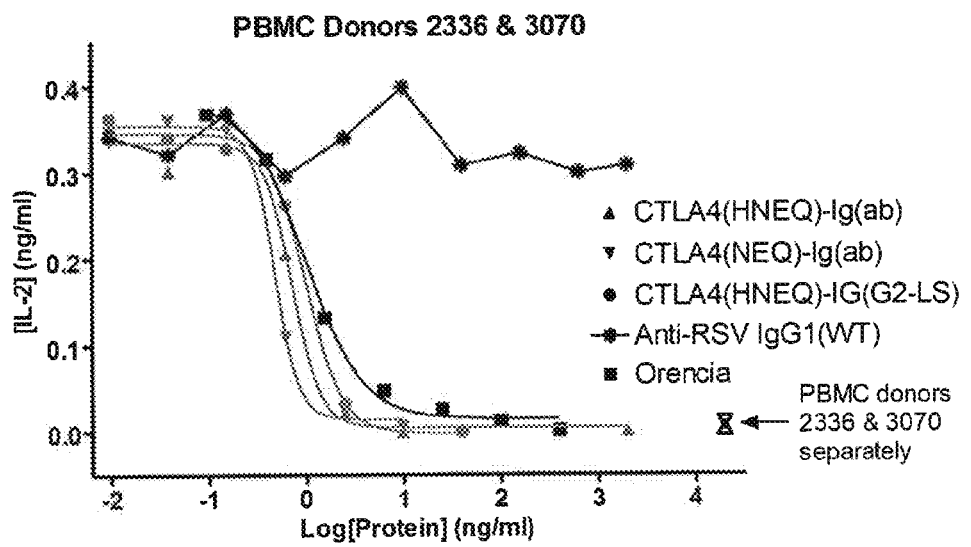
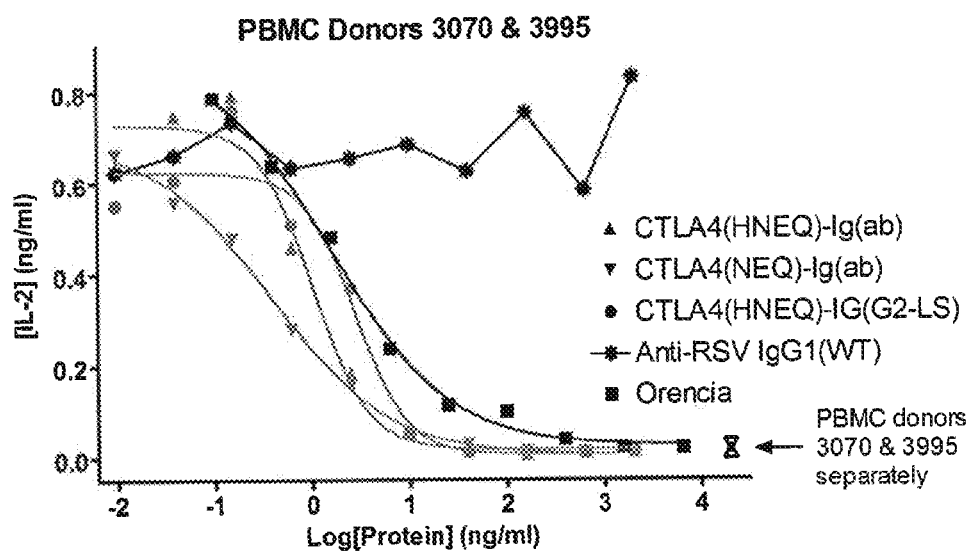
Figure 15

Day 21
IgG response to tetanus toxoid
1 mg/kg CTLA4-Ig proteins

CTLA4-IG IMMUNOADHESINS

This application is a divisional application of U.S. application Ser. No. 13/032,491, now U.S. Pat. No. 8,329,867, filed Feb. 22, 2011 which claims benefit under 35 U.S.C. §119(e) to U.S. Ser. No. 61/412,309, filed Nov. 10, 2010; U.S. Ser. No. 61/334,806, filed May 14, 2010; and U.S. Ser. No. 61/306,311, filed Feb. 19, 2010 entirely incorporated herein by reference.

FIELD OF THE INVENTION

The present application relates to CTLA4-Ig immunoadhesins that target CD80 and CD86, and their use, particularly for therapeutic purposes.

BACKGROUND OF THE INVENTION

T lymphocytes play a central role in the adaptive immune response to antigen. Naive T cells require two signals for their full activation (Bretscher 1999, Proc Natl Acad Sci USA 96:185-90). The first signal is antigen-specific and is provided by interaction of the T-cell receptor (TCR) with MHC/peptide complex on an antigen-presenting cell (APC). The second signal is a costimulatory signal provided by the interactions between receptors on the T cell and their ligands on the APC. Engagement of both TCR/MHC and co-stimulatory interactions leads to T-cell activation via a number of intracellular pathways, including calcium-calcineurin and RAS mitogen-activated protein kinase, and subsequent activation of transcription factors for a number of effector compounds, including cytokines such as IL-2. These events lead to T-cell proliferation, generation of a $CD4^+$ helper T-cell ($T_H$) pool, and expansion of activated $CD8^+$ cytotoxic T cells. Not only is co-stimulation critical for full T-cell activation, its absence during TCR/MHC engagement results in anergy and/or apoptosis.

Although multiple positive and negative costimulatory pathways are involved in T-cell regulation, the most critical are between CD28 on T cells and B7-1 (CD80) and B7-2 (CD86) on APCs. CD28 promotes T-cell differentiation into TH1 phenotype cells and enhances antibody production by B cells and activation of T cells. B7-1 and B7-2, expressed on APCs such as dendritic cells (DC) and B cells, have overlapping but distinct functions. B7-2 is constitutively expressed and is rapidly upregulated on APCs coincident with TCR/MHC engagement (signal 1). B7-1 expression is very low on the resting cell, but is typically induced after prolonged T-cell stimulation. These differences suggest that while B7-2 may be important in initialization of T-cell activation, B7-1 may play a greater role in perpetuating the immune response.

Subsequent to T-cell activation, a negative regulatory receptor Cytotoxic T-Lymphocyte Antigen 4 (CTLA4 or CTLA-4, also called CD152), is upregulated on T cells (Alegre et al., 2001, Nat Rev Immunol 1:220-8). CTLA4 is structurally homologous to CD28 but binds more tightly to both B7-1 and B7-2 ligands. CLTA4 inhibits the immune response in two principal ways—it competes with CD28 for the B7 ligands and thus blocks costimulation, and it also negatively signals to inhibit T cell activation (Krummel and Allison, 1995, J Exp Med 182:459-465; Walunas et al., 1994, Immunity 1:405-413). Recent work has shown that B7-2 engages CD28 more than CTLA4 at the immune synapse, while B7-1 ligates more CTLA4 than CD28 (Collins et al., 2002, Immunity 17:201-210; Jansson et al., 2005, J Immunol 175:1575-1585).

Because of the critical role of the B7 co-stimulatory pathway in promoting and maintaining immune response, therapeutic agents designed to antagonize it are promising for the treatment of autoimmune diseases and disorders. Abatacept (Orencia®), is a CTLA4-Ig immunoadhesin consisting of the extracellular binding domain of CTLA4 linked to the Fc domain of a human IgG. Abatacept was developed to inhibit B7-mediated costimulation (Bluestone et al., 2006, Immunity 24:233-238), and is approved for the treatment of rheumatoid arthritis (RA) and in clinical trials for a number of other autoimmune indications. However, whereas abatacept shows some activity in treating RA, it is not effective for other indications. For example, CTLA4-Ig is far less efficacious in tolerance against transplant rejection (Kirk et al., 1997, Proc Natl Acad Sci USA 94:8789-8794; Levisetti et al., 1997, J Immunol 159:5187-5191).

The deficient clinical performance of abatacept has been attributed to its suboptimal affinity of native CTLA4 for the B7 ligands, particularly B7-2 due to its presumed importance in the initiation of immunity. The present invention provides novel variant CTLA4-Ig immunoadhesins with improved B7 affinities and enhanced T-cell inhibitory activities. Such novel immunoadhesins are of benefit in a variety of applications, particularly for treating immune related disorders, as discussed in detail below.

SUMMARY OF THE INVENTION

The present invention provides novel CTLA4-Ig immunoadhesins that inhibit interactions between antigen presenting cells (APCs) and T cells. The CTLA4-Ig immunoadhesins of the invention comprise a CTLA4 portion that binds with high affinity to human B7-1 (CD80) and B7-2 (CD86), and comprise an Ig Fc portion (or Fc region) that may bind to one or more Fc receptors or Fc ligands.

In one aspect of the invention, the CTLA4-Ig immunoadhesin comprises a variant CTLA4 protein, wherein said variant comprises at least one amino acid modification in a native CTLA4 protein, wherein said modification is a substitution selected from the group consisting of A29E, A29F, A29H, A29K, A29N, A29Q, A29R, T30E, T30H, T30R, T30V, E31D, E31I, E31M, E31T, E31V, R33E, R33F, R33I, R33L, R33M, R33Q, R33T, R33W, R33Y, T35D, T35E, T35F, T35M, T35V, T35Y, A49D, A49E, A49F, A49T, A49W, A49Y, T51D, T51E, T51H, T51L, T51N, T51Q, T51R, T51S, T51V, M53E, M53F, M53H, M53Q, M53W, M53Y, T59H, T59I, T59L, T59N, T59Q, T59V, T59Y, L61A, L61D, L61E, L61F, L61G, L61H, L61I, L61K, L61M, L61N, L61P, L61Q, L61R, L61S, L61T, L61V, L61W, L61Y, D63E, S64K, S64R, S64Y, K93D, K93E, K93F, K93H, K93N, K93Q, K93R, K93S, K93T, K93V, K93W, K93Y, E95D, E95H, E95L, E95Q, E95Y, M97D, M97F, M97I, M97N, M97V, Y98F, Y98W, Y102F, Y102W, Y103D, Y103E, Y103F, Y103H, Y103N, Y103Q, Y103W, L104F, L104H, L104M, L104V, L104Y, G105D, G105E, I106E, and I106Y, wherein said substitution provides enhanced binding to B7-1 and/or B7-2. In a preferred aspect of the invention, the CTLA4-Ig immunoadhesin comprises a CTLA4 substitution selected from the group consisting of A29H, T51N, M53Y, L61E, and K93Q, wherein said substitution provides enhanced binding to B7-1 and/or B7-2. In a most preferred aspect of the invention, the CTLA4-Ig immunoadhesin comprises a CTLA4 substitution selected from the group consisting of A29H, T51N, L61E, and K93Q, wherein said substitution provides enhanced binding to B7-1 and/or B7-2. In other aspects of the invention, the CTLA4-Ig immunoadhesin comprises a CTLA4 substitution selected from the group consisting of A29H, A29K, T51N, L61E, and Y103Q, wherein said substitution provides enhanced binding to B7-1 and/or B7-2. In other aspects of the invention, the CTLA4-Ig immunoadhesin comprises a CTLA4 substitution selected from the group consisting of K93V, L61Q, and L104H, wherein said substitution provides enhanced binding to B7-1 and/or B7-2.

In another aspect of the invention, the CTLA4-Ig immunoadhesin comprises a variant CTLA4 protein, wherein said variant comprises a combination of CTLA4 substitutions selected from the group consisting of A29H/K93Q, A29H/M53Y, A29H/T51N, T51N/K93Q, T51N/M53Y, A29H/L61E/K93Q, A29H/M53Y/K93Q, A29H/M53Y/L61E, A29H/T51N/L61E, M53Y/L61E/K93Q, T51N/L61E/K93Q, T51N/M53Y/L61E, A29H/M53Y/L61E/K93Q, A29H/T51N/L61E/K93Q, A29H/T51N/M53Y/K93Q, A29H/T51N/M53Y/L61E, T51N/M53Y/L61E/K93Q, and A29H/T51N/M53Y/L61E/K93Q, wherein said variant provides enhanced binding to B7-1 and/or B7-2. In a preferred aspect of the invention, the CTLA4-Ig immunoadhesin comprises a combination of CTLA4 substitutions selected from the group consisting of T51N/L61E/K93Q and A29H/T51N/L61E/K93Q, wherein said variant provides enhanced binding to B7-1 and/or B7-2. In other aspects of the invention, the CTLA4-Ig immunoadhesin comprises a combination of CTLA4 substitutions selected from the group consisting of T51N/L61E/K93Q, A29H/T51N/L61E/K93Q, A29H/T51N, T51N/M53Y, and T51N/M53Y/L61E, wherein said variant provides enhanced binding to B7-1 and/or B7-2.

In another aspect of the invention, the CTLA4-Ig immunoadhesin comprises a variant CTLA4 protein, wherein said variant comprises a substitution at a CTLA4 position selected from the group consisting of 35, 49, 51, 53, 59, 61, and 95, wherein said variant provides enhanced binding to B7-1 and/or B7-2. In a preferred aspect of the invention, the CTLA4-Ig immunoadhesin comprises a variant CLTA4 protein, wherein said variant comprises a substitution at a CTLA4 position selected from the group consisting of 51 and 61, wherein said variant provides enhanced binding to B7-1 and/or B7-2.

In an additional aspect, the invention provides immunoadhesins comprising a first domain comprising a variant human CTLA4 and a second domain comprising an IgG Fc region, wherein said first domain has the formula: Fx(1-28)-Vb(29)-Fx(30-50)-Vb(51)-Fx(52)-Vb(53)-Fx(54-60)-Vb(61)-Fx(62-92)-Vb(93)-Fx(94-124)[SEQ ID NO: 1], wherein Fx(1-28) is the sequence MHVAQPAVVLASSRGIASFVCEYASPGK (positions 1-28 of SEQ ID NO: 1); Vb(29) is selected from the group consisting of A and H; Fx(30-50) is the sequence TEVRVTVLRQADSQVTEVCAA (positions 30-50 of SEQ ID NO: 1); Vb(51) is selected from the group consisting of T and N; Fx(52) is Y; Vb(53) is selected from the group consisting of M and Y; Fx(54-60) is the sequence MGNELTF (positions 54-60 of SEQ ID NO: 1); Vb(61) is selected from the group consisting of L and E; Fx(62-92) is the sequence DDSICTGTSSGNQVNLTIQGLRAMDTGLYIC (positions 62-92 of SEQ ID NO: 1); Vb(93) is selected from the group consisting of K and Q; and Fx(94-124) is the sequence VELMYPPPYYLGIGNGTQIYVIDPEPCPDSD (positions 94-124 of SEQ ID NO: 1); wherein said variant comprises at least one amino acid modification as compared to SEQ ID NO: 6 and wherein said variant exhibits increased binding to B7-1, B7-2 or both B7-1 and B7-2.

In a further aspect, the invention provides immunoadhesins comprising a first domain comprising a variant human CTLA4 and a second domain comprising an IgG Fc region, wherein said first domain has the formula: Fx(1-28)-Vb(29)-Fx(30-50)-Vb(51)-Fx(52)-Vb(53)-Fx(54-60)-Vb(61)-Fx(62-92)-Vb(93)-Fx(94-124) [SEQ ID NO: 2], wherein Fx(1-28) is the sequence MHVAQPAVVLASSRGIASFVCEYASPGK (positions 1-28 of SEQ ID NO: 2); Vb(29) is H; Fx(30-50) is the sequence TEVRVTVLRQADSQVTEVCAA (positions 30-50 of SEQ ID NO: 2); Vb(51) is selected from the group consisting of T and N; Fx(52) is Y; Vb(53) is selected from the group consisting of M and Y; Fx(54-60) is the sequence MGNELTF (positions 54-60 of SEQ ID NO: 2); Vb(61) is selected from the group consisting of L and E; Fx(62-92) is the sequence DDSICTGTSSGNQVNLTIQGLRAMDTGLYIC (positions 62-92 of SEQ ID NO: 2); Vb(93) is selected from the group consisting of K and Q; and Fx(94-124) is the sequence VELMYPPPYYLGIGNGTQIYVIDPEPCPDSD (positions 94-124 of SEQ ID NO: 2); wherein said variant exhibits increased binding to B7-1, B7-2 or both B7-1 and B7-2.

In an additional aspect, the invention provides immunoadhesins comprising a first domain comprising a variant human CTLA4 and a second domain comprising an IgG Fc region, wherein said first domain has the formula: Fx(1-28)-Vb(29)-Fx(30-50)-Vb(51)-Fx(52)-Vb(53)-Fx(54-60)-Vb(61)-Fx(62-92)-Vb(93)-Fx(94-124) [SEQ ID NO: 3], wherein Fx(1-28) is the sequence MHVAQPAVVLASSRGIASFVCEYASPGK (positions 1-28 of SEQ ID NO: 3); Vb(29) is selected from the group consisting of A and H; Fx(30-50) is the sequence TEVRVTVLRQADSQVTEVCAA (positions 30-50 of SEQ ID NO: 3); Vb(51) is N; Fx(52) is Y; Vb(53) is selected from the group consisting of M and Y; Fx(54-60) is the sequence MGNELTF (positions 54-60 of SEQ ID NO: 3); Vb(61) is selected from the group consisting of L and E; Fx(62-92) is the sequence DDSICTGTSSGNQVNLTIQGLRAMDTGLYIC (positions 62-92 of SEQ ID NO: 3); Vb(93) is selected from the group consisting of K and Q; and Fx(94-124) is the sequence VELMYPPPYYLGIGNGTQIYVIDPEPCPDSD (positions 94-124 of SEQ ID NO: 3); wherein said variant exhibits increased binding to B7-1, B7-2 or both B7-1 and B7-2.

In a further aspect, the invention provides immunoadhesins comprising a first domain comprising a variant human CTLA4 and a second domain comprising an IgG Fc region, wherein said first domain has the formula: Fx(1-28)-Vb(29)-Vb(30)-Vb(31)-Fx(32)-Vb(33)-Fx(34)-Vb(35)-Fx(36-48)-Vb(49)-Fx(50)-Vb(51)-Fx(52)-Vb(53)-Fx(54-58)-Vb(59)-Fx(60)-Vb(61)-Fx(62)-Vb(63)-Vb(64)-Fx(65-92)-Vb(93)-Fx(94)-Vb(95)-Fx(96)-Vb(97)-Vb(98)-Fx(99-101)-Vb(102)-Vb(103)-Vb(104)-Vb(105)-Vb(106)-Fx(107-124) [SEQ ID NO: 4]; wherein Fx(1-28) is the sequence MHVAQPAVVLASSRGIASFVCEYASPGK (positions 1-28 of SEQ ID NO: 4); Vb(29) is selected from the group consisting of A, E, F, H, K, N, Q and R; Vb(30) is selected from the group consisting of T, H and V; Vb(31) is selected from the group consisting of E, D, I, M, T and V; Fx(32) is V; Vb(33) is selected from the group consisting of R, E, F, I, L, M, Q, T, W and Y; Fx(34) is V; Vb(35) is selected from the group consisting of T, D, E, F, M, V and Y; Fx(36-48) is the sequence VLRQADSQVTEVC (positions 36-48 of SEQ ID NO: 4); Vb(49) is selected from the group consisting of A, D, E, F, T, W and Y; Fx(50) is A; Vb(51) is selected from the group consisting of T, D, E, H, L, N, Q, R, S and V; Fx(52) is Y; Vb(53) is selected from the group consisting of M, E, F, H, Q, W and Y; Fx(54-58) is the sequence MGNEL (positions 54-58 of SEQ ID NO: 4); Vb(59) is selected from the group consisting of T, H, I, L, N, Q, V and Y; Fx(60) is F; Vb(61) is selected from the group consisting of L, A, D, E, F, G, H, I, K, M, N, P, Q, R, S, T, V, W and Y; Fx(62) is D; Vb(63) is selected from the group consisting of D and E; Vb(64) is selected from the group consisting of S, K, R and Y; Fx(65-92) is the sequence ICTGTSSGNQVNLTIQGLRAMDTGLYIC (positions 65-92 of SEQ ID NO: 3); Vb(93) is selected from the group consisting of K, D, E, F, H, N, Q, R, S, T, V, W and Y; Fx(94) is V; Vb(95) is selected from the group consisting of E, D, H, L, Q and Y; Fx(96) is L; Vb(97) is selected from the group consisting of M, D, F, I, N and V; Vb(98) is selected from the group consisting of Y, F and W; Fx(99-101) is the sequence PPP; Vb(102) is selected from the group consisting of Y, F and W; Vb(103) is selected from the group consisting of Y, D, E, F, H, N, Q and W; Vb(104) is selected from the group consisting of L, F, H, M, V and Y; Vb(105) is selected from the group consisting of G, D and E; Vb(106) is selected from the group consisting of I, E and Y; and Fx(107-124) is the sequence GNGTQIYVIDPEPCPDSD (positions 107-124 of SEQ ID NO: 4), wherein said variant comprises at least one amino acid modification as compared to SEQ ID NO:2 band wherein said variant exhibits increased binding to B7-1, B7-2 or both B7-1 and B7-2.

In an additional aspect, the invention provides immunoadhesins comprising SEQ ID NO: 8, wherein said immunoadhesin comprises an amino acid modification as compared to SEQ ID NO: 6.

IN a further aspect, the invention provides immunoadhesins comprising a first domain comprising a variant CTLA4 as compared to SEQ ID NO:6 and a second domain comprising an IgG Fc region, wherein said CTLA4 variant comprises an amino acid modification selected from the group consisting of T51N, A29H, M53Y, L61E, and K93Q, wherein said variant provides enhanced binding to B7-1, B7-2, or both B7-1 and B7-2.

In an additional aspect, the invention provides immunoadhesins comprising a first domain comprising a variant CTLA4 as compared to SEQ ID NO: 6 and a second domain comprising an IgG Fc region, wherein said CTLA4 variant comprises an amino acid modification at a position selected from the group consisting of 51, 53, 61 and 93 using the number of SEQ ID NO: 6, wherein said variant provides enhanced binding to B7-1, B7-2, or both B7-1 and B7-2.

In one aspect of the invention, the CTLA4-Ig immunoadhesins comprise a native Fc region. Preferred native Fc regions of the invention include but are not limited to IgG1, IgG2, IgG3, and IgG4 Fc regions.

In preferred aspects of the invention, the CTLA4-Ig immunoadhesins comprise a variant Fc region. In a preferred aspect of the invention, the variant Fc region enhances affinity to the neonatal Fc receptor FcRn. In a most preferred aspect of the invention, the variant Fc region extends half-life of the CTLA4-Ig in vivo. Preferred variants for enhancing FcRn affinity and/or extending half-life in vivo include but are not limited to 259I, 307Q, 308F, 311I, 311V, 378V, 378T, 426V, 428L, 434S, 436I, 436V, 250Q, 434A, 252Y, 254T, and 256E, wherein numbering is according to the EU index. Most preferred variants for enhancing FcRn affinity and/or extending half-life in vivo are 428L and 434S, wherein numbering is according to the EU index.

The present invention provides isolated nucleic acids encoding the novel CTLA4-Ig immunoadhesins described herein. The present invention provides vectors comprising said nucleic acids, optionally, operably linked to control sequences. The present invention provides host cells containing the vectors, and methods for producing and optionally recovering the immunoadhesins.

The present invention provides novel CTLA4-Ig proteins. Said novel CTLA4-Ig proteins may find use in a therapeutic product.

The present invention provides compositions comprising CTLA4-Ig proteins described herein, and a physiologically or pharmaceutically acceptable carrier or diluent.

The present invention contemplates therapeutic and diagnostic uses for the CTLA4-Ig immunoadhesins disclosed herein. The CTLA4-Ig immunoadhesins of the invention are preferably used to treat an immune related disorder. In the most preferred embodiments of the invention, the CTLA4-Ig immunoadhesins described herein are used to treat Crohn's disease, systemic lupus erythematosus (SLE), lupus nephritis, psoriatic arthritis, psoriasis, rheumatoid arthritis, ulcerative colitis, and/or transplant rejection.

BRIEF DESCRIPTION OF THE DRAWINGS

FIG. 1. Amino acid sequences of full length human CTLA4, the extracellular domain (ECD) of human CTLA4, and the belatacept A29Y/L104E variant version of human CTLA4. The ECD of CTLA4 is highlighted in gray in the full length CTLA4 sequence. Gray in the belatacept sequence highlights the A29Y/L104E substitutions [SEQ ID NOs. 5-8].

FIG. 2. Amino acid sequences of exemplary Fc regions. The Fc region herein is defined as position 230 to the C-terminus (230-447) based on the EU numbering scheme. Gray highlights indicate modifications from native IgG Fc regions [SEQ ID NOs. 9-15].

FIG. 3. Amino acid sequences of exemplary linkers. The numbering of the linkers is based on the EU index, and contains residues 216-229, where 216 is the N-terminal 216E of the four native IgG isotypes based on EU numbering. Addition of the N-terminal Q does not alter the number (i.e. 216E is still 216E). Gray highlights indicate modifications from native IgG linkers [SEQ ID NOs. 16-23].

FIG. 4. Amino acid sequences of exemplary combinations of linkers and Fc regions used in the present study. Gray highlights indicate modifications from native IgG constant region sequences [SEQ ID NOs. 24-27].

FIG. 5. Amino acid sequences of select CTLA4-Ig immunoadhesins studied in the present work [SEQ ID NOs. 28-30].

FIG. 8. Biacore sensorgrams for binding to CD86 (top) and CD80 (bottom) comparing CTLA4-Ig variant HNEQ (A29H/T51N/L61E/K93Q) to abatacept and belatacept.

FIG. 9. Amino acid sequences of exemplary variant CTLA4 and variant CTLA4-Ig proteins [SEQ ID NOs. 31-34].

FIG. 10. T-cell inhibitory activity of CTLA4-Ig variants. T cells were activated by co-ligation of CD3 using an anti-CD3 antibody and B7-2 using recombinant B7-2-Ig. CFSE-labeled T cells were monitored using flow cytometry.

FIG. 11. Amino acid sequences of exemplary CTLA4-Ig variants with Fc variants that extend in vivo half-life [SEQ ID NOs. 35-38].

FIG. 15. T-cell inhibitory activity of CTLA4-Ig variants in a mixed lymphocyte reaction. T cells were activated by mixture of allogeneic PBMCs in two sets of experiments (one with donors 2336 and 3070 (top) and one with donors 3070 and 3995 (bottom). Activation was quantitated by measuring release of IL-2 measured by ELISA.

DETAILED DESCRIPTION OF THE INVENTION

Overview

Figure 6:
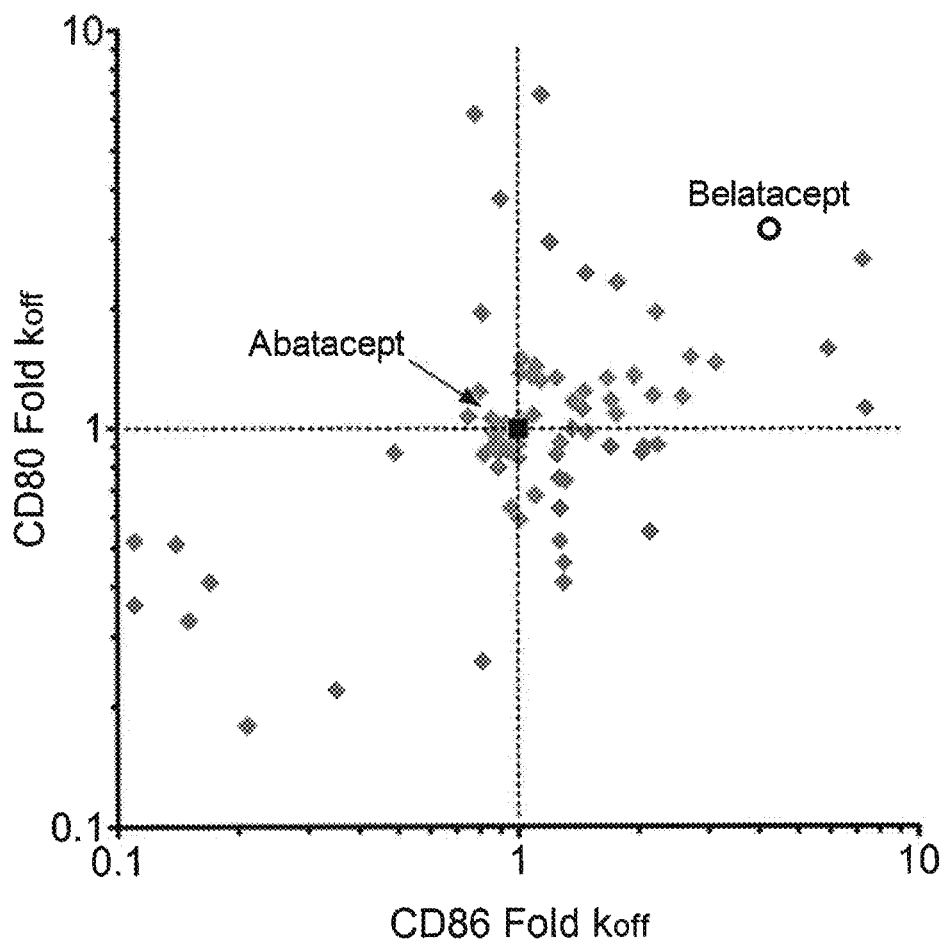
FIG. 6. Plot of the Fold($k_{off}$) relative to abatacept for all of the screened single substitution CTLA4-Ig variants, represented as gray triangles. The black square represents the parent CTLA4-Ig abatacept, and the black open circle represents belatacept.

The present invention is drawn to novel variant CTLA4-Ig immunoadhesins with improved B7 affinities and enhanced T-cell inhibitory activities. Such novel immunoadhesins are of benefit in a variety of applications as discussed in detail below.

CTLA4 (Cytotoxic T-Lymphocyte Antigen 4), also referred to as CTLA-4 and also known as CD152 (Cluster of differentiation 152), is a protein that plays an important regulatory role in the immune system. In humans, the CTLA4 protein is encoded by the CTLA4 gene, the translated amino acid sequence of which is provided in SEQ ID NO:1. CTLA4 is a member of the immunoglobulin superfamily, and is structurally homologous to CD28, a T cell costimulatory protein. CTLA4 binds to costimulatory ligands B7-1 and B7-2 on the surface of antigen presenting cells (APCs). CLTA4 inhibits immune response in two principal ways—it competes with CD28 for binding to B7-1 and B7-2 and thereby blocks costimulation, and it negatively signals to inhibit T cell activation. A particularly important region of the CTLA4 protein for the present invention is the extracellular domain (ECD) (SEQ ID NO:2), which mediates binding to B7-1 and B7-2 ligands on APCs.

As a result of the critical role of the B7 co-stimulatory pathway in promoting and maintaining immune response, it is desirable to provide therapeutic agents designed to antagonize this pathway. Accordingly, the present invention provides CTLA4Ig immunoadhesions

CTLA4-Ig Immunoadhesins

The Invention Provides CTLA4Ig Immunoadhesins.

"Immunoadhesin" refers to a protein wherein one or more polypeptides is operably linked to an Fc region. Immunoadhesin as used herein is synonymous with the terms "Fc fusion", "Ig fusion", "receptor Fc fusion", "Ig chimera", and "receptor globulin" (sometimes with dashes), and "TRAPs" as used in the prior art (Chamow et al., 1996, Trends Biotechnol 14:52-60; Ashkenazi et al., 1997, Curr Opin Immunol 9:195-200, both entirely incorporated by reference). An immunoadhesin combines the Fc region of an immunoglobulin with a fusion partner, which in general can be any protein or small molecule that has specificity for a target protein. Thus immunoadhesins have two principal portions—a target binding portion and an Fc portion. The target binding portion may have specificity for virtually any target or target antigen. The Fc portion may bind to one or more Fc receptors or Fc ligands. Fusion partners may be linked to any region of an Fc region, including at the N- or C-termini, or at some residue in-between the termini. While virtually any protein or small molecule may be linked to Fc to generate an Fc fusion, and thus target virtually any target, immunonoadhesins of the present invention comprise a CTLA4 or a variant of CTLA4 as a fusion partner. The fusion of CTLA4 with an Ig Fc region is referred to herein as a CTLA4-Ig or CTLA4-Ig protein.

CTLA4 Variants

The target binding portion or fusion partner of the immunoadhesins of the invention are comprised of the protein CTLA4. Thus the immunoadhesins of the invention are directed to bind B7-1, B7-2, and any other ligands or receptors, known or unknown, that are bound by CTLA4. The target binding portion of the invention may comprise an amino acid sequence that is made up of all, any, or part of the human CTLA4 protein (SEQ ID NO:1). Preferably the immunoadhesin binding portion comprises all or part of the ECD of CTLA4 (SEQ ID NO:2). As described in the examples, the immunoadhesin binding is preferably a variant of CTLA4 that improves binding to B7-1, B7-2, or both B7-1 and B7-2 and in some cases shows preferential binding to one or the other.

The CTLA4 variants comprise at least one amino acid modification in a native CTLA4 protein, generally the human CTLA4 protein depicted in SEQ ID NO;1, and in most cases, the variants are within the extracellular domain as the entire CTLA4 protein is generally not used in the fusion proteins of the invention. In this embodiment, one or more modifications are made at one or more of the following positions (numbering as in SEQ ID NO:2): 29, 30, 31, 33, 35, 49, 51, 53, 59, 61, 63, 64, 93, 95, 97, 98, 102, 103, 104, 105 or 106. In some embodiments, the modification is one or more of the following substitutions: A29E, A29F, A29H, A29K, A29N, A29Q, A29R, T30E, T30H, T30R, T30V, E31D, E31I, E31M, E31T, E31V, R33E, R33F, R33I, R33L, R33M, R33Q, R33T, R33W, R33Y, T35D, T35E, T35F, T35M, T35V, T35Y, A49D, A49E, A49F, A49T, A49W, A49Y, T51D, T51E, T51H, T51L, T51N, T51Q, T51R, T51S, T51V, M53E, M53F, M53H, M53Q, M53W, M53Y, T59H, T59I, T59L, T59N, T59Q, T59V, T59Y, L61A, L61D, L61E, L61F, L61G, L61H, L61I, L61K, L61M, L61N, L61P, L61Q, L61R, L61S, L61T, L61V, L61W, L61Y, D63E, S64K, S64R, S64Y, K93D, K93E, K93F, K93H, K93N, K93Q, K93R, K93S, K93T, K93V, K93W, K93Y, E95D, E95H, E95L, E95Q, E95Y, M97D, M97F, M97I, M97N, M97V, Y98F, Y98W, Y102F, Y102W, Y103D, Y103E, Y103F, Y103H, Y103N, Y103Q, Y103W, L104F, L104H, L104M, L104V, L104Y, G105D, G105E, I106E, and I106Y, Of particular use in some embodiments are CTLA4 variants that have one or more substitutions selected from A29H, T51N, M53Y, L61E, and K93Q, with combinations of particular use including A29H/K93Q, A29H/M53Y, A29H/T51N, T51N/K93Q, T51N/M53Y, A29H/L61E/K93Q, A29H/M53Y/K93Q, A29H/M53Y/L61E, A29H/T51N/L61E, M53Y/L61E/K93Q, T51N/L61E/K93Q, T51N/M53Y/L61E, A29H/M53Y/L61E/K93Q, A29H/T51N/L61E/K93Q, A29H/T51N/M53Y/K93Q, A29H/T51N/M53Y/L61E, T51N/M53Y/L61E/K93Q, and A29H/T51N/M53Y/L61E/K93Q, As for all the lists of positions and substitutions herein, it should be understood that combinations of individual substitutions can be made, of any and all possible combinations, and that any individual position or substitution can be independently included or excluded from the list of possibilities. In general, as compared to the wild-type or parent CTLA4 (or Fc region), generally the variants of the invention have 1, 2, 3, 4, or 5 amino acid substitutions in the CTLA4 region, although in some cases more substitutions can be used, as long as the desired function is preserved. Similarly, as described below, the Fc domain may have substitutions in this manner as well.

As described elsewhere, the CTLA4 variants generally preserve or enhance binding to one or more of the CTLA4 ligands, such as enhanced binding to B7-1 and/or B7-2.

Fc Domains

The Fc portion of the immunoadhesins of the invention are comprised of the Fc region or some portion of the Fc region of an antibody. Antibodies are immunoglobulins that bind a specific antigen. In most mammals, including humans and mice, antibodies are constructed from paired heavy and light polypeptide chains. The light and heavy chain variable regions show significant sequence diversity between antibodies, and are responsible for binding the target antigen. Each chain is made up of individual immunoglobulin (Ig) domains, and thus the generic term immunoglobulin is used for such proteins.

Traditional natural antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. IgA has several subclasses, including but not limited to IgA1 and IgA2. Thus, "isotype" as used herein is meant any of the classes and subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE. The distinguishing features between these antibody classes are their constant regions, although subtler differences may exist in the variable regions.

Each of the light and heavy chains are made up of two distinct regions, referred to as the variable and constant regions. The IgG heavy chain is composed of four immunoglobulin domains linked from N- to C-terminus in the order VH-CH1-CH2-CH3, referring to the heavy chain variable domain, heavy chain constant domain 1, heavy chain constant domain 2, and heavy chain constant domain 3 respectively (also referred to as VH-Cγ1-Cγ2-Cγ3, referring to the heavy chain variable domain, constant gamma 1 domain, constant gamma 2 domain, and constant gamma 3 domain respectively). The IgG light chain is composed of two immunoglobulin domains linked from N- to C-terminus in the order VL-CL, referring to the light chain variable domain and the light chain constant domain respectively. The constant regions show less sequence diversity, and are responsible for binding a number of natural proteins to elicit important biochemical events. The structure that constitutes the natural biological form of an antibody, including the variable and constant regions, is referred to herein as a "full length antibody". In most mammals, including humans and mice, the full length antibody of the IgG isotype is a tetramer and consists of two identical pairs of two immunoglobulin chains, each pair having one light and one heavy chain, each light chain comprising immunoglobulin domains VL and CL, and each heavy chain comprising immunoglobulin domains VH, Cγ1, Cγ2, and Cγ3.

The variable region, typically the amino-terminal portion of an antibody contains the antigen binding determinants of the molecule, and thus determines the specificity of an antibody for its target antigen. The variable region is so named because it is the most distinct in sequence from other antibodies within the same class.

The carboxy-terminal portion of each chain defines a constant region primarily responsible for effector function. In the IgG subclass of immunoglobulins, there are several immunoglobulin domains in the heavy chain referred to as heavy constant (CH) regions. In the context of IgG antibodies, the IgG isotypes each have three CH regions. Accordingly, "CH" domains in the context of IgG are as follows: "CH1" refers to positions 118-220 according to the EU index as in Kabat. "CH2" refers to positions 237-340 according to the EU index as in Kabat, and "CH3" refers to positions 341-447 according to the EU index as in Kabat.

Another important region of the heavy chain is the hinge region. By "hinge" or "hinge region" or "antibody hinge region" or "immunoglobulin hinge region" herein is meant the flexible polypeptide comprising the amino acids between the first and second constant domains of an antibody. Structurally, the IgG CH1 domain ends at EU position 220, and the IgG CH2 domain begins at residue EU position 237. Thus for IgG the antibody hinge is herein defined to include positions 221 (D221 in IgG1) to 236 (G236 in IgG1), wherein the numbering is according to the EU index as in Kabat. In some embodiments, for example in the context of an Fc region, the lower hinge is included, with the "lower hinge" generally referring to positions 226 or 230 to 236.

For all constant region positions discussed in the present invention, numbering is according to the EU index as in Kabat (Kabat et al., 1991, *Sequences of Proteins of Immunological Interest*, 5th Ed., United States Public Health Service, National Institutes of Health, Bethesda, entirely incorporated by reference). Those skilled in the art of antibodies will appreciate that these conventions consist of nonsequential numbering in specific regions of an immunoglobulin sequence, enabling a normalized reference to conserved positions in immunoglobulin families. Accordingly, the positions of any given immunoglobulin as defined by the EU index will not necessarily correspond to its sequential sequence.

The immunoadhesins of the invention are proteins that are fusions of CTLA4 with the Fc region of an antibody. By "Fc" or "Fc region", as used herein is meant the polypeptide comprising the constant region of an antibody excluding the first constant region immunoglobulin domain and in some cases, part of the hinge. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains Cgamma2 and Cgamma3 (Cγ2 and Cγ3) and the lower hinge region between Cgamma1 (Cγ1) and Cgamma2 (Cγ2). Although the boundaries of the Fc region may vary, the human IgG heavy chain Fc region is defined to include residue 230 to the C-terminus, wherein numbering is based on the EU numbering scheme. Fc may refer to this region in isolation, or this region in the context of an Fc polypeptide. By "Fc polypeptide" as used herein is meant a polypeptide that comprises all or part of an Fc region. Fc polypeptides include antibodies, Fc fusions, isolated Fc's, and Fc fragments.

The Fc region of an antibody interacts with a number of Fc receptors and ligands, imparting an array of important functional capabilities referred to as effector functions. For IgG the Fc region, Fc comprises Ig domains Cγ2 and Cγ3 and the N-terminal hinge leading into Cγ2. An important family of Fc receptors for the IgG class are the Fc gamma receptors (FcγRs). These receptors mediate communication between antibodies and the cellular arm of the immune system (Raghavan et al., 1996, Annu Rev Cell Dev Biol 12:181-220; Ravetch et al., 2001, Annu Rev Immunol 19:275-290, both hereby entirely incorporated by reference). In humans this protein family includes FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al., 2002, Immunol Lett 82:57-65, hereby entirely incorporated by reference). These receptors typically have an extracellular domain that mediates binding to Fc, a membrane spanning region, and an intracellular domain that may mediate some signaling event within the cell. These receptors are expressed in a variety of immune cells including monocytes, macrophages, neutrophils, dendritic cells, eosinophils, mast cells, platelets, B cells, large granular lymphocytes, Langerhans' cells, natural killer (NK) cells, and γδ T cells. Formation of the Fc/FcγR complex recruits these effector cells to sites of bound antigen, typically resulting in signaling events within the cells and important subsequent immune responses such as release of inflammation mediators, B cell activation, endocytosis, phagocytosis, and cytotoxic attack. The ability to mediate cytotoxic and phagocytic effector functions is a potential mechanism by which antibodies destroy targeted cells. The cell-mediated reaction wherein nonspecific cytotoxic cells that express FcγRs recognize bound antibody on a target cell and subsequently cause lysis of the target cell is referred to as antibody dependent cell-mediated cytotoxicity (ADCC) (Raghavan et al., 1996, Annu Rev Cell Dev Biol 12:181-220; Ghetie et al., 2000, Annu Rev Immunol 18:739-766; Ravetch et al., 2001, Annu Rev Immunol 19:275-290, both hereby entirely incorporated by reference). The cell-mediated reaction wherein nonspecific cytotoxic cells that express FcγRs recognize bound antibody on a target cell and subsequently cause phagocytosis of the target cell is referred to as antibody dependent cell-mediated phagocytosis (ADCP).

The different IgG subclasses have different affinities for the FcγRs, with IgG1 and IgG3 typically binding substantially better to the receptors than IgG2 and IgG4 (Jefferis et al., 2002, Immunol Lett 82:57-65, hereby entirely incorporated by reference). The FcγRs bind the IgG Fc region with different affinities. The extracellular domains of FcγRIIIa and FcγRIIIb are 96% identical, however FcγRIIIb does not have a intracellular signaling domain. Furthermore, whereas FcγRI, FcγRIIa/c, and FcγRIIIa are positive regulators of immune complex-triggered activation, characterized by having an intracellular domain that has an immunoreceptor tyrosine-based activation motif (ITAM), FcγRIIb has an immunoreceptor tyrosine-based inhibition motif (ITIM) and is therefore inhibitory. Thus the former are referred to as activation receptors, and FcγRIIb is referred to as an inhibitory receptor. Despite these differences in affinities and activities, all FcγRs bind the same region on Fc, at the N-terminal end of the Cγ2 domain and the preceding hinge.

An overlapping but separate site on Fc serves as the interface for the complement protein C1q. In the same way that Fc/FcγR binding mediates ADCC, Fc/C1q binding mediates complement dependent cytotoxicity (CDC). A site on Fc between the Cγ2 and Cγ3 domains mediates interaction with the neonatal receptor FcRn, the binding of which recycles endocytosed antibody from the endosome back to the bloodstream (Raghavan et al., 1996, Annu Rev Cell Dev Biol 12:181-220; Ghetie et al., 2000, Annu Rev Immunol 18:739-766, both hereby entirely incorporated by reference). This process, coupled with preclusion of kidney filtration due to the large size of the full length molecule, results in favorable antibody serum half-lives ranging from one to three weeks. Binding of Fc to FcRn also plays a key role in antibody transport. The binding site for FcRn on Fc is also the site at which the bacterial proteins A and G bind. The tight binding by these proteins is typically exploited as a means to purify antibodies by employing protein A or protein G affinity chromatography during protein purification. The fidelity of these regions, the complement and FcRn/protein A binding regions are important for both the clinical properties of antibodies and their development.

A key feature of the Fc region is the conserved N-linked glycosylation that occurs at N297. This carbohydrate, or oligosaccharide as it is sometimes referred, plays a critical structural and functional role for the antibody, and is one of the principle reasons that antibodies must be produced using mammalian expression systems. Efficient Fc binding to FcγR and C1q requires this modification, and alterations in the composition of the N297 carbohydrate or its elimination affect binding to these proteins.

The immunoglobulins of embodiments disclosed herein may be substantially encoded by immunoglobulin genes belonging to any of the antibody classes. In certain embodiments, the immunoglobulins disclosed herein comprise sequences belonging to the IgG class of antibodies, including IgG1, IgG2, IgG3, or IgG4. In alternate embodiments, immunoglobulins disclosed herein comprise sequences belonging to the IgA (including subclasses IgA1 and IgA2), IgD, IgE, IgG, or IgM classes of antibodies. The immunoglobulins disclosed herein may comprise more than one protein chain, e.g., may be an antibody or Fc fusion that is a monomer or an oligomer, including a homo- or hetero-oligomer.

Immunoglobulins disclosed herein may be substantially encoded by genes from any organism, e.g., mammals (including, but not limited to humans, rodents (including but not limited to mice and rats), lagomorpha (including but not limited to rabbits and hares), camelidae (including but not limited to camels, llamas, and dromedaries), and non-human primates, including but not limited to Prosimians, Platyrrhini (New World monkeys), Cercopithecoidea (Old World monkeys), and Hominoidea including the Gibbons and Lesser and Great Apes. In the most preferred embodiments, the immunoglobulins disclosed herein may be substantially human.

As is well known in the art, immunoglobulin polymorphisms exist in the human population. Gm polymorphism is determined by the IGHG1, IGHG2 and IGHG3 genes which have alleles encoding allotypic antigenic determinants referred to as G1m, G2m, and G3m allotypes for markers of the human IgG1, IgG2 and IgG3 molecules (no Gm allotypes have been found on the gamma 4 chain). Markers may be classified into 'allotypes' and 'isoallotypes'. These are distinguished on different serological bases dependent upon the strong sequence homologies between isotypes. Allotypes are antigenic determinants specified by allelic forms of the Ig genes. Allotypes represent slight differences in the amino acid sequences of heavy or light chains of different individuals. Even a single amino acid difference can give rise to an allotypic determinant, although in many cases there are several amino acid substitutions that have occurred. Allotypes are sequence differences between alleles of a subclass whereby the antisera recognize only the allelic differences. An isoallotype is an allele in one isotype which produces an epitope which is shared with a non-polymorphic homologous region of one or more other isotypes and because of this the antisera will react with both the relevant allotypes and the relevant homologous isotypes (Clark, 1997, IgG effector mechanisms, Chem Immunol. 65:88-110; Gorman & Clark, 1990, Semin Immunol 2(6):457-66, both hereby entirely incorporated by reference).

Allelic forms of human immunoglobulins have been well-characterized (WHO Review of the notation for the allotypic and related markers of human immunoglobulins. J Immunogen 1976, 3: 357-362; WHO Review of the notation for the allotypic and related markers of human immunoglobulins. 1976, Eur. J. Immunol. 6, 599-601; Loghem E van, 1986, Allotypic markers, Monogr Allergy 19: 40-51, all hereby entirely incorporated by reference). Additionally, other polymorphisms have been characterized (Kim et al., 2001, J. Mol. Evol. 54:1-9, hereby entirely incorporated by reference). At present, 18 Gm allotypes are known: G1m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b5, b0, b3, b4, s, t, g1, c5, u, v, g5) (Lefranc, et al., The human IgG subclasses: molecular analysis of structure, function and regulation. Pergamon, Oxford, pp. 43-78 (1990); Lefranc, G. et al., 1979, Hum. Genet.: 50, 199-211, both hereby entirely incorporated by reference). Allotypes that are inherited in fixed combinations are called Gm haplotypes. The immunoglobulins disclosed herein may be substantially encoded by any allotype, isoallotype, or haplotype of any immunoglobulin gene.

CTLA4 proteins may be linked to Fc regions via a linker. The term "linker" is used to denote polypeptides comprising two or more amino acid residues joined by peptide bonds and are used to link one or more antigen binding portions. Such linker polypeptides are well known in the art (see e.g., Holliger, P., et al. (1993) Proc. Natl. Acad. Sci. USA 90:6444-6448; Poljak, R. J., et al. (1994) Structure 2:1121-1123). A variety of linkers may find use in some embodiments described herein to covalently link Fc regions to a fusion partner. "Linker" herein is also referred to as "linker sequence", "spacer", "tethering sequence" or grammatical equivalents thereof. Homo- or hetero-bifunctional linkers as are well known (see, 1994 Pierce Chemical Company catalog, technical section on cross-linkers, pages 155-200, incorporated entirely by reference). A number of strategies may be used to covalently link molecules together. These include, but are not limited to polypeptide linkages between N- and C-termini of proteins or protein domains, linkage via disulfide bonds, and linkage via chemical cross-linking reagents. In one aspect of this embodiment, the linker is a peptide bond, generated by recombinant techniques or peptide synthesis. The linker peptide may predominantly include the following amino acid residues: Gly, Ser, Ala, or Thr. The linker peptide should have a length that is adequate to link two molecules in such a way that they assume the correct conformation relative to one another so that they retain the desired activity. In one embodiment, the linker is from about 1 to 20 amino acids in length, preferably about 1 to 30 amino acids in length. In one embodiment, linkers of 1 to 20 amino acids in length may be used. Useful linkers include glycine-serine polymers, including for example (GS)n, (GSGGS)n [SEQ ID NO: 39], (GGGGS)n [SEQ ID NO: 40], and (GGGS)n [SEQ ID NO: 41], where n is an integer of at least one, glycine-alanine polymers, alanine-serine polymers, and other flexible linkers. Alternatively, a variety of nonproteinaceous polymers, including but not limited to polyethylene glycol (PEG), polypropylene glycol, polyoxyalkylenes, or copolymers of polyethylene glycol and polypropylene glycol, may find use as linkers, that is may find use as linkers.

Preferred linkers of the invention comprise sequences from an antibody hinge region. Hinge regions sequences from any antibody isotype may be used, including for example hinge sequences from IgG1, IgG2, IgG3, and/or IgG4. Linker sequences may also include any sequence of any length of CL/CH1 domain but not all residues of CL/CH1 domain; for example the first 5-12 amino acid residues of the CL/CH1 domains. Linkers can be derived from immunoglobulin heavy chains of any isotype, including for example Cγ1, Cγ2, Cγ3, Cγ4, Cα1, Cα2, Cδ, Cε, and Cμ. Linkers can be derived from immunoglobulin light chain, for example Cκ or Cλ. Linker sequences may also be derived from other proteins such as Ig-like proteins (e.g. TCR, FcR, KIR), hinge region-derived sequences, and other natural sequences from other proteins.

Amino Acid Modifications in CTLA4-Ig Immunoadhesins

CTLA4-Ig immunoadhesins disclosed herein may comprise a variant CTLA4, a variant Fc region, or both a variant CTLA4 and a variant Fc region. A variant comprises one or more amino acid modifications relative to a parent CTLA4-Ig protein, wherein the amino acid modification(s) provide one or more optimized properties. By "modification" herein is meant an alteration in the physical, chemical, or sequence properties of a protein, polypeptide, antibody, or CTLA4-Ig immunoadhesin. By "amino acid" and "amino acid identity" as used herein is meant one of the 20 naturally occurring amino acids or any non-natural analogues that may be present at a specific, defined position. Thus "amino acid" as used herein means both naturally occurring and synthetic amino acids. For example, homophenylalanine, citrulline and norleucine are considered amino acids for the purposes of the invention. "Amino acid" also includes imino acid residues such as proline and hydroxyproline. The side chain may be in either the (R) or the (S) configuration. In the preferred embodiment, the amino acids are in the (S) or L-configuration. If non-naturally occurring side chains are used, non-amino acid substituents may be used, for example to prevent or retard in vivo degradation. An amino acid modification can be an amino acid substitution, insertion, and/or deletion in a polypeptide sequence. By "amino acid substitution" or "substitution" herein is meant the replacement of an amino acid at a particular position in a parent polypeptide sequence with another amino acid. By "amino acid insertion" or "insertion" as used herein is meant the addition of an amino acid at a particular position in a parent polypeptide sequence. By "amino acid deletion" or "deletion" as used herein is meant the removal of an amino acid at a particular position in a parent polypeptide sequence.

A variant disclosed herein differs in amino acid sequence from its parent by virtue of at least one amino acid modification. By "parent polypeptide", "parent protein", "precursor polypeptide", or "precursor protein" as used herein is meant an unmodified polypeptide that is subsequently modified to generate a variant. Said parent polypeptide may be a naturally occurring polypeptide, i.e. a WT or native protein, or a variant or engineered version of a naturally occurring polypeptide. Parent polypeptide may refer to the polypeptide itself, compositions that comprise the parent polypeptide, or the amino acid sequence that encodes it. By "wild type", "WT", or "native" herein is meant an amino acid sequence or a nucleotide sequence that is found in nature, including allelic variations. A WT protein, including for example a WT CTLA4 or WT Fc region protein, has an amino acid sequence or a nucleotide sequence that has not been intentionally modified.

The CTLA4-Ig immunoadhesins disclosed herein may have more than one amino acid modification as compared to the parent, for example from about one to fifty amino acid modifications, e.g., from about one to ten amino acid modifications, from about one to about five amino acid modifications, etc. compared to the parent. Thus the sequences of the variants and those of the parent polypeptide are substantially homologous. For example, the variant sequences herein will possess about 80% homology with the parent sequence, e.g., at least about 90% homology, at least about 95% homology, at least about 98% homology, at least about 99% homology, etc. Modifications disclosed herein also include glycoform modifications. Modifications may be made genetically using molecular biology, or may be made enzymatically or chemically.

Variants disclosed herein are defined according to the amino acid modifications that compose them. Thus, for example, the substitution T51N in CTLA4 refers a CTLA4 variant in which the threonine at position 51 is replaced with asparagine. As another example, the substitution N434S in the Fc region refers to an Fc variant in which the asparagine at position 434 is replaced with serine. Likewise, M428L/N434S defines an Fc variant with the substitutions M428L and N434S relative to the parent Fc polypeptide. The identity of the WT amino acid may be unspecified, in which case the aforementioned variant is referred to as 428L/434S. It is noted that the order in which substitutions are provided is arbitrary, that is to say that, for example, 428L/434S is the same Fc variant as 434S/428L For modifications in CTLA4, numbering of positions herein is according to the sequential numbering of the extracellular region of CTLA4 provided in SEQ ID NO:6. Antibody constant region and Fc region positions discussed herein are numbered according to the EU index or EU numbering scheme (Kabat et al., 1991, Sequences of Proteins of Immunological Interest, 5th Ed., United States Public Health Service, National Institutes of Health, Bethesda, hereby entirely incorporated by reference). The EU index or EU index as in Kabat or EU numbering scheme refers to the numbering of the EU antibody (Edelman et al., 1969, Proc Natl Acad Sci USA 63:78-85, hereby entirely incorporated by reference).

The goal of the variants herein is to provide one or more optimized properties, typically by altering affinity for a target ligand or Fc receptor. Affinity may be enhanced or reduced relative to a parent protein. By "greater affinity" or "improved affinity" or "enhanced affinity" or "better affinity" than a parent polypeptide, as used herein is meant that a variant binds to a ligand or receptor with a significantly higher equilibrium constant of association (KA or Ka) or lower equilibrium constant of dissociation (KD or Kd) than the parent polypeptide done under the same conditions, for example, when the amounts of variant and parent polypeptide in the binding assay are essentially the same.

For example, a CTLA4 variant with improved B7-2 binding affinity may display from about 1.2, 1.5, 2, 5, 10, 15, 20, 25, 30, 35, 40, 45, 50, 55, 60, 65, 70, 75, 80, 85, 90, 95, 100 fold or more, improvement in B7-2 binding affinity compared to the parent CTLA4 polypeptide, where B7-2 binding affinity is determined, for example, by the binding methods disclosed herein, including but not limited to Biacore™, by one skilled in the art.

Accordingly, by "reduced affinity" as compared to a parent polypeptide as used herein is meant that a variant binds a ligand or receptor with significantly lower KA or higher KD than the parent polypeptide. Greater or reduced affinity can also be defined relative to an absolute level of affinity.

The immunoadhesins herein preferably comprise a variant CTLA4. CTLA4 variants may improve binding to B7-1, B7-2, or both B7-1 and B7-2. CTLA4 variants may improve binding selectively to B7-2 relative to B7-1. That is, variants may enhance affinity of CTLA4 for B7-2, but either reduce affinity for B7-1, not affect affinity for B7-1, or improve affinity for B7-1 less than the affinity improvement to B7-2. Alternatively, variants may improve binding selectively to B7-1 relative to B7-2.

The immunoadhesins herein preferably comprise an Fc variant. The Fc variants disclosed herein may be optimized for improved or reduced binding to Fc receptors or Fc ligands. By "Fc receptor" or "Fc ligand" as used herein is meant a molecule, preferably a polypeptide, from any organism that binds to the Fc region of an antibody to form an Fc-ligand complex. Fc ligands include but are not limited to FcγRs, FcγRs, FcγRs, FcRn, C1q, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs. Fc ligands may include undiscovered molecules that bind Fc.

In preferred embodiments, CTLA4-Ig immunoadhesins disclosed herein incorporate Fc variants that improve FcRn binding. Such variants may enhance the in vivo pharmacokinetic properties of the CTLA4-Ig immunoadhesins. Preferred variants that increase binding to FcRn and/or improve pharmacokinetic properties include but are not limited to substitutions at positions 259, 308, 428, and 434, including but not limited to for example 259I, 308F, 428L, 428M, 434S, 434H, 434F, 434Y, and 434M (U.S. Ser. No. 12/341,769, filed Dec. 22, 2008, entitled "Fc Variants with Altered Binding to FcRn", entirely incorporated by reference). Other variants that increase Fc binding to FcRn include but are not limited to: 250E, 250Q, 428L, 428F, 250Q/428L (Hinton et al., 2004, J. Biol. Chem. 279(8): 6213-6216, Hinton et al. 2006 Journal of Immunology 176:346-356), 256A, 272A, 286A, 305A, 307A, 307Q, 311A, 312A, 376A, 378Q, 380A, 382A, 434A (Shields et al, Journal of Biological Chemistry, 2001, 276(9): 6591-6604, entirely incorporated by reference), 252F, 252T, 252Y, 252W, 254T, 256S, 256R, 256Q, 256E, 256D, 256T, 309P, 311S, 433R, 433S, 433I, 433P, 433Q, 434H, 434F, 434Y, 252Y/254T/256E, 433K/434F/436H, 308T/309P/311S (Dall Acqua et al. Journal of Immunology, 2002, 169: 5171-5180, Dall'Acqua et al., 2006, Journal of Biological Chemistry 281:23514-23524, entirely incorporated by reference). Other modifications for modulating FcRn binding are described in Yeung et al., 2010, J Immunol, 182:7663-7671.

Other Fc modifications for use in the present invention include variants that reduce or ablate binding to FcγRs and/or complement proteins, thereby reducing or ablating Fc-mediated effector functions such as ADCC, ADCP, and CDC. Such variants are also referred to herein as "knockout variants" or "KO variants". Variants that reduce binding to FcγRs and complement are useful for reducing unwanted interactions mediated by the Fc region and for tuning the selectivity of the CTLA4-Ig immunoadhesins. Preferred knockout variants are described in US 2008-0242845 A1, published on Oct. 2, 2008, entitled "Fc Variants with Optimized Properties, expressly incorporated by reference herein. Preferred modifications include but are not limited substitutions, insertions, and deletions at positions 234, 235, 236, 237, 267, 269, 325, and 328, wherein numbering is according to the EU index. Preferred substitutions include but are not limited to 234G, 235G, 236R, 237K, 267R, 269R, 325L, and 328R, wherein numbering is according to the EU index. A preferred variant comprises 236R/328R. Variants may be used in the context of any IgG isotype or IgG isotype Fc region, including but not limited to human IgG1, IgG2, IgG3, and/or IgG4. Preferred IgG Fc regions for reducing FcγR and complement binding and reducing Fc-mediated effector functions are IgG2 and IgG4 Fc regions. Hybrid isotypes may also be useful, for example hybrid IgG1/IgG2 isotypes as described in U.S. Ser. No. 11/256,060. Other modifications for reducing FcγR and complement interactions include but are not limited to substitutions 297A, 234A, 235A, 237A, 318A, 228P, 236E, 268Q, 309L, 330S, 331S, 220S, 226S, 229S, 238S, 233P, and 234V, as well as removal of the glycosylation at position 297 by mutational or enzymatic means or by production in organisms such as bacteria that do not glycosylate proteins. These and other modifications are reviewed in Strohl, 2009, Current Opinion in Biotechnology 20:685-691, incorporated by reference in its entirety.

Fc modifications that improve binding to FcγRs and/or complement may also find use in the CTLA4-Ig immunoadhesins herein. Such Fc variants may enhance Fc-mediated effector functions such as ADCC, ADCP, and/or CDC. Preferred modifications for improving FcγR and complement binding are described in US 2006-0024298 A1, published on Feb. 2, 2006, and US 2006-0235208 A1, published on Oct. 19, 2006, expressly incorporated herein by reference. Preferred modifications comprise a substitution at a position selected from the group consisting of 236, 239, 268, 324, and 332, wherein numbering is according to the EU index. Preferred substitutions include but are not limited to 236A, 239D, 239E, 268D, 267E, 268E, 268F, 324T, 332D, and 332E. Preferred variants include but are not limited to 239D/332E, 236A/332E, 236A/239D/332E, 268F/324T, 267E/268F, 267E/324T, and 267E/268F/324T. Other modifications for enhancing FcγR and complement interactions include but are not limited to substitutions 298A, 333A, 334A, 326A, 247I, 339D, 339Q, 280H, 290S, 298D, 298V, 243L, 292P, 300L, 396L, 305I, and 396L. These and other modifications are reviewed in Strohl, 2009, ibid.

In one embodiment, the CTLA4-Ig immunoadhesins disclosed herein may incorporate Fc variants that enhance affinity for an inhibitory receptor FcγRIIb. Such variants may provide the CTLA4-Ig immunoadhesins herein with immunomodulatory activities related to FcγRIIb+ cells, including for example B cells and monocytes. In one embodiment, the Fc variants provide selectively enhanced affinity to FcγRIIb relative to one or more activating receptors. Modifications for altering binding to FcγRIIb are described in U.S. Ser. No. 12/156,183, filed May 30, 2008, entitled "Methods and Compositions for Inhibiting CD32b Expressing Cells", herein expressly incorporated by reference. In particular, Fc variants that improve binding to FcγRIIb may include one or more modifications at a position selected from the group consisting of 234, 235, 236, 237, 239, 266, 267, 268, 325, 326, 327, 328, and 332, according to the EU index. Preferable substitutions for enhancing FcγRIIb affinity include but are not limited to 234D, 234E, 234W, 235D, 235F, 235R, 235Y, 236D, 236N, 237D, 237N, 239D, 239E, 266M, 267D, 267E, 268D, 268E, 327D, 327E, 328F, 328W, 328Y, and 332E. More preferably, substitutions include but are not limited to 235Y, 236D, 239D, 266M, 267E, 268D, 268E, 328F, 328W, and 328Y. Preferred Fc variants for enhancing binding to FcγRIIb include but are not limited to 235Y/267E, 236D/267E, 239D/268D, 239D/267E, 267E/268D, 267E/268E, and 267E/328F.

CTLA4-Ig immunoadhesins described herein can incorporate Fc modifications in the context of any IgG isotype or IgG isotype Fc region, including but not limited to human IgG1, IgG2, IgG3, and/or IgG4. The IgG isotype may be selected such as to alter FcγR- and/or complement-mediated effector function(s). Hybrid IgG isotypes may also be useful. For example, U.S. Ser. No. 11/256,060 describes a number of hybrid IgG1/IgG2 constant regions that may find use in the particular invention. In some embodiments of the invention, CTLA4-Ig immunoadhesins may comprise means for isotypic modifications, that is, modifications in a parent IgG to the amino acid type in an alternate IgG. For example, an IgG1/IgG3 hybrid variant may be constructed by a substitutional means for substituting IgG1 positions in the CH2 and/or CH3 region with the amino acids from IgG3 at positions where the two isotypes differ. Thus a hybrid variant IgG antibody may be constructed that comprises one or more substitutional means, e.g., 274Q, 276K, 300F, 339T, 356E, 358M, 384S, 392N, 397M, 422I, 435R, and 436F. In other embodiments of the invention, an IgG1/IgG2 hybrid variant may be constructed by a substitutional means for substituting IgG2 positions in the CH2 and/or CH3 region with amino acids from IgG1 at positions where the two isotypes differ. Thus a hybrid variant IgG antibody may be constructed that comprises one or more substitutional means, e.g., one or more of the following amino acid substations: 233E, 234L, 235L, -236G (referring to an insertion of a glycine at position 236), and 327A.

As will be appreciated by those in the art, the disclosure of individual and combination variants in the Fc region can be independently and optionally combined with any of the CTLA4 variants disclosed herein. That is, as described herein, CTLA4 variants are individually and optionally selected and/or combined within the set of disclosed variants, in any combination. Similarly, the lists above of suitable Fc domain variants can be individually and optionally combined in any way, not only within the Fc region but with any CTLA4 variants. That is, a CTLA4 variant may be selected that comprises a number of variants, for example A29H/T51N/L61E/K93Q, and these variants can be combined with Fc domain variants, such as 239D/332E, and/or 428L/434S. Thus, the disclosure of a "list" of possible individual variants is meant to include any and all possible combinations within the list as well as with other lists of variants for the same or other purposes.

Glycoform Modifications

Antibody Fc regions contain carbohydrate at conserved positions in the constant regions of the heavy chain. Each antibody isotype has a distinct variety of N-linked carbohydrate structures. Aside from the carbohydrate attached to the heavy chain, up to 30% of human IgGs have a glycosylated Fab region. IgG has a single N-linked biantennary carbohydrate at Asn297 of the CH2 domain. For IgG from either serum or produced ex vivo in hybridomas or engineered cells, the IgG are heterogeneous with respect to the Asn297 linked carbohydrate. For human IgG, the core oligosaccharide normally consists of GlcNAc2Man3GlcNAc, with differing numbers of outer residues.

The carbohydrate moieties of immunoadhesins disclosed herein will be described with reference to commonly used nomenclature for the description of oligosaccharides. A review of carbohydrate chemistry which uses this nomenclature is found in Hubbard et al. 1981, Ann. Rev. Biochem. 50:555-583. This nomenclature includes, for instance, Man, which represents mannose; GlcNAc, which represents 2-N-acetylglucosamine; Gal which represents galactose; Fuc for fucose; and Glc, which represents glucose. Sialic acids are described by the shorthand notation NeuNAc, for 5-N-acetyl-neuraminic acid, and NeuNGc for 5-glycolylneuraminic.

The term "glycosylation" means the attachment of oligosaccharides (carbohydrates containing two or more simple sugars linked together e.g. from two to about twelve simple sugars linked together) to a glycoprotein. The oligosaccharide side chains are typically linked to the backbone of the glycoprotein through either N- or O-linkages. The oligosaccharides of immunoadhesins disclosed herein occur generally are attached to a CH2 domain of an Fc region as N-linked oligosaccharides. "N-linked glycosylation" refers to the attachment of the carbohydrate moiety to an asparagine residue in a glycoprotein chain. The skilled artisan will recognize that, for example, each of murine IgG1, IgG2a, IgG2b and IgG3 as well as human IgG1, IgG2, IgG3, IgG4, IgA and IgD CH2 domains have a single site for N-linked glycosylation at residue 297.

For the purposes herein, a "mature core carbohydrate structure" refers to a processed core carbohydrate structure attached to an Fc region which generally consists of the following carbohydrate structure GlcNAc(Fucose)-GlcNAc-Man-(Man-GlcNAc)$_2$ typical of biantennary oligosaccharides. The mature core carbohydrate structure is attached to the Fc region of the glycoprotein, generally via N-linkage to Asn297 of a CH2 domain of the Fc region. A "bisecting GlcNAc" is a GlcNAc residue attached to the α1,4 mannose of the mature core carbohydrate structure. The bisecting GlcNAc can be enzymatically attached to the mature core carbohydrate structure by a α(1,4)-N-acetylglucosaminyl-transferase III enzyme (GnTIII). CHO cells do not normally express GnTIII (Stanley et al., 1984, J. Biol. Chem. 261: 13370-13378), but may be engineered to do so (Umana et al., 1999, Nature Biotech. 17:176-180).

Described herein are CTLA4-Ig immunoadhesins that comprise modified glycoforms or engineered glycoforms. By "modified glycoform" or "engineered glycoform" as used herein is meant a carbohydrate composition that is covalently attached to a protein, for example an antibody, wherein said carbohydrate composition differs chemically from that of a parent protein. Engineered glycoforms may be useful for a variety of purposes, including but not limited to enhancing or reducing FcγR-mediated effector function. In one embodiment, the CTLA4-Ig immunoadhesins disclosed herein are modified to control the level of fucosylated and/or bisecting oligosaccharides that are covalently attached to the Fc region.

A variety of methods are well known in the art for generating modified glycoforms (Umaña et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473; U.S. Ser. No. 12/434,533; all of which are expressly incorporated by reference). These techniques control the level of fucosylated and/or bisecting oligosaccharides that are covalently attached to the Fc region, for example by expressing an IgG in various organisms or cell lines, engineered or otherwise (for example Lec-13 CHO cells or rat hybridoma YB2/0 cells), by regulating enzymes involved in the glycosylation pathway (for example FUT8 [α-1,6-fucosyltranserase] and/or β1-4-N-acetylglucosaminyltransferase III [GnTIII]), by modifying carbohydrate(s) after the IgG has been expressed, or by expressing antibody in the presence of fucose analogs as enzymatic inhibitors. Other methods for modifying glycoforms of the CTLA4-Ig immunoadhesins disclosed herein include using glycoengineered strains of yeast (Li et al., 2006, Nature Biotechnology 24(2):210-215), moss (Nechansky et al., 2007, Mol Immunjol 44(7):1826-8), and plants (Cox et al., 2006, Nat Biotechnol 24(12):1591-7). The use of a particular method to generate a modified glycoform is not meant to constrain embodiments to that method. Rather, embodiments disclosed herein encompass CTLA4-Ig immunoadhesins with modified glycoforms irrespective of how they are produced.

In one embodiment, CTLA4-Ig immunoadhesins disclosed herein are glycoengineered to alter the level of sialylation. Higher levels of sialylated Fc glycans in CTLA4-Ig immunoadhesin G molecules can adversely impact functionality (Scallon et al., 2007, Mol Immunol. 44(7):1524-34), and differences in levels of Fc sialylation can result in modified anti-inflammatory activity (Kaneko et al., 2006, Science 313: 670-673). Because antibodies may acquire anti-inflammatory properties upon sialylation of Fc core polysaccharide, it may be advantageous to glycoengineer the CTLA4-Ig immunoadhesins disclosed herein for greater or reduced Fc sialic acid content.

Engineered glycoform typically refers to the different carbohydrate or oligosaccharide; thus for example an immuoglobulin may comprise an engineered glycoform. Alternatively, engineered glycoform may refer to the CTLA4-Ig immunoadhesin that comprises the different carbohydrate or oligosaccharide. In one embodiment, a composition disclosed herein comprises a glycosylated CTLA4-Ig immunoadhesin having an Fc region, wherein about 51-100% of the glycosylated antibody, e.g., 80-100%, 90-100%, 95-100%, etc. of the antibody in the composition comprises a mature core carbohydrate structure which lacks fucose. In another embodiment, the antibody in the composition both comprises a mature core carbohydrate structure that lacks fucose and additionally comprises at least one amino acid modification in the Fc region. In an alternative embodiment, a composition comprises a glycosylated CTLA4-Ig immunoadhesin having an Fc region, wherein about 51-100% of the glycosylated antibody, 80-100%, or 90-100%, of the antibody in the composition comprises a mature core carbohydrate structure which lacks sialic acid. In another embodiment, the antibody in the composition both comprises a mature core carbohydrate structure that lacks sialic acid and additionally comprises at least one amino acid modification in the Fc region. In yet another embodiment, a composition comprises a glycosylated CTLA4-Ig immunoadhesin having an Fc region, wherein about 51-100% of the glycosylated antibody, 80-100%, or 90-100%, of the antibody in the composition comprises a mature core carbohydrate structure which contains sialic acid. In another embodiment, the antibody in the composition both comprises a mature core carbohydrate structure that contains sialic acid and additionally comprises at least one amino acid modification in the Fc region. In another embodiment, the combination of engineered glycoform and amino acid modification provides optimal Fc receptor binding properties to the antibody.

Other Modifications

CTLA4-Ig immunoadhesins disclosed herein may comprise one or more modifications that provide optimized properties. Said modifications may be amino acid modifications, or may be modifications that are made enzymatically or chemically. Such modification(s) likely provide some improvement in the CTLA4-Ig immunoadhesin, for example an enhancement in its stability, solubility, function, or clinical use. Disclosed herein are a variety of improvements that may be made by coupling the CTLA4-Ig immunoadhesins disclosed herein with additional modifications.

In one embodiment, modifications are made to improve biophysical properties of the CTLA4-Ig immunoadhesins disclosed herein, including but not limited to stability, solubility, and oligomeric state. Modifications can include, for example, substitutions that provide more favorable intramolecular interactions in the CTLA4-Ig immunoadhesin such as to provide greater stability, or substitution of exposed nonpolar amino acids with polar amino acids for higher solubility.

Other modifications to the CTLA4-Ig immunoadhesins disclosed herein include those that enable the specific formation or homodimeric or homomultimeric molecules. Such modifications include but are not limited to engineered disulfides, as well as chemical modifications or aggregation methods.

In further embodiments, the CTLA4-Ig immunoadhesins disclosed herein comprise modifications that remove proteolytic degradation sites. These may include, for example, protease sites that reduce production yields, as well as protease sites that degrade the administered protein in vivo. In one embodiment, additional modifications are made to remove covalent degradation sites such as deamidation (i.e. deamidation of glutaminyl and asparaginyl residues to the corresponding glutamyl and aspartyl residues), oxidation, and proteolytic degradation sites. Deamidation sites that are particular useful to remove are those that have enhance propensity for deamidation, including, but not limited to asparaginyl and glutamyl residues followed by glycines (NG and QG motifs, respectively). In such cases, substitution of either residue can significantly reduce the tendency for deamidation. Common oxidation sites include methionine and cysteine residues. Other covalent modifications, that can either be introduced or removed, include hydroxylation of proline and lysine, phosphorylation of hydroxyl groups of seryl or threonyl residues, methylation of the "-amino groups of lysine, arginine, and histidine side chains, acetylation of the N-terminal amine, and amidation of any C-terminal carboxyl group. Additional modifications also may include but are not limited to posttranslational modifications such as N-linked or O-linked glycosylation and phosphorylation.

Modifications may include those that improve expression and/or purification yields from hosts or host cells commonly used for production of biologics. These include, but are not limited to various mammalian cell lines (e.g. CHO), yeast cell lines, bacterial cell lines, and plants. Additional modifications include modifications that remove or reduce the ability of heavy chains to form inter-chain disulfide linkages. Additional modifications include modifications that remove or reduce the ability of heavy chains to form intra-chain disulfide linkages.

The CTLA4-Ig immunoadhesins disclosed herein may comprise modifications that include the use of unnatural amino acids incorporated using, including but not limited to methods described in Liu & Schultz, 2010, Annu Rev Biochem 79:413-444, herein expressly incorporated by reference. In some embodiments, these modifications enable manipulation of various functional, biophysical, immunological, or manufacturing properties discussed above. In additional embodiments, these modifications enable additional chemical modification for other purposes.

Other modifications are contemplated herein. For example, the CTLA4-Ig immunoadhesin may be linked to one of a variety of nonproteinaceous polymers, e.g., polyethylene glycol (PEG), polypropylene glycol, polyoxyalkylenes, or copolymers of polyethylene glycol and polypropylene glycol. Additional amino acid modifications may be made to enable specific or non-specific chemical or posttranslational modification of the CTLA4-Ig immunoadhesins. Such modifications, include, but are not limited to PEGylation and glycosylation. Specific substitutions that can be utilized to enable PEGylation include, but are not limited to, introduction of novel cysteine residues or unnatural amino acids such that efficient and specific coupling chemistries can be used to attach a PEG or otherwise polymeric moiety. Introduction of specific glycosylation sites can be achieved by introducing novel N-X-T/S sequences into the CTLA4-Ig immunoadhesins disclosed herein.

Modifications to reduce immunogenicity may include modifications that reduce binding of processed peptides derived from the parent sequence to MHC proteins. For example, amino acid modifications would be engineered such that there are no or a minimal number of immune epitopes that are predicted to bind, with high affinity, to any prevalent MHC alleles. Several methods of identifying MHC-binding epitopes in protein sequences are known in the art and may be used to score epitopes in an antibody disclosed herein.

Covalent modifications are included within the scope of CTLA4-Ig immunoadhesins disclosed herein, and are generally, but not always, done post-translationally. For example, several types of covalent modifications can be introduced into the molecule by reacting specific amino acid residues with an organic derivatizing agent that is capable of reacting with selected side chains or the N- or C-terminal residues. In some embodiments, the covalent modification of the immunoglobulins disclosed herein comprises the addition of one or more labels. The term "labeling group" means any detectable label. In some embodiments, the labeling group is coupled to the CTLA4-Ig immunoadhesin via spacer arms of various lengths to reduce potential steric hindrance. Various methods for labeling proteins are known in the art and may be used in generating CTLA4-Ig immunoadhesins disclosed herein.

In one embodiment, the CTLA4-Ig immunoadhesins disclosed herein are "fusion proteins", sometimes referred to herein as "conjugates". The fusion partner or conjugate partner can be proteinaceous or non-proteinaceous; the latter generally being generated using functional groups on the CTLA4-Ig immunoadhesin and on the conjugate partner. Conjugate and fusion partners may be any molecule, including small molecule chemical compounds and polypeptides. For example, a variety of conjugates and methods are described in Trail et al., 1999, Curr. Opin. Immunol. 11:584-588, incorporated entirely by reference. Possible conjugate partners include but are not limited to cytokines, cytotoxic agents, toxins, radioisotopes, chemotherapeutic agent, antiangiogenic agents, a tyrosine kinase inhibitors, and other therapeutically active agents. In some embodiments, conjugate partners may be thought of more as payloads, that is to say that the goal of a conjugate is targeted delivery of the conjugate partner to a targeted cell, for example a cancer cell or immune cell, by the CTLA4-Ig immunoadhesin. Thus, for example, the conjugation of a toxin to an CTLA4-Ig immunoadhesin targets the delivery of said toxin to cells expressing the target antigen. As will be appreciated by one skilled in the art, in reality the concepts and definitions of fusion and conjugate are overlapping. The designation of a fusion or conjugate is not meant to constrain it to any particular embodiment disclosed herein. Rather, these terms are used loosely to convey the broad concept that any CTLA4-Ig immunoadhesin disclosed herein may be linked genetically, chemically, or otherwise, to one or more polypeptides or molecules to provide some desirable property.

Production of CTLA4-Ig Immunoadhesins

Also disclosed herein are methods for producing and experimentally testing CTLA4-Ig immunoadhesins. The disclosed methods are not meant to constrain embodiments to any particular application or theory of operation. Rather, the provided methods are meant to illustrate generally that one or more CTLA4-Ig immunoadhesins may be produced and experimentally tested to obtain CTLA4-Ig immunoadhesins. General methods for antibody and protein molecular biology, expression, purification, and screening are described in Antibody Engineering, edited by Kontermann & Dubel, Springer, Heidelberg, 2001; and Hayhurst & Georgiou, 2001, Curr Opin Chem Biol 5:683-689; Maynard & Georgiou, 2000, Annu Rev Biomed Eng 2:339-76;

In one embodiment disclosed herein, nucleic acids are created that encode the CTLA4-Ig immunoadhesins, and that may then be cloned into host cells, expressed and assayed, if desired. Thus, nucleic acids, and particularly DNA, may be made that encode each protein sequence. These practices are carried out using well-known procedures. For example, a variety of methods that may find use in generating CTLA4-Ig immunoadhesins disclosed herein are described in Molecular Cloning—A Laboratory Manual, 3rd Ed. (Maniatis, Cold Spring Harbor Laboratory Press, New York, 2001), and Current Protocols in Molecular Biology (John Wiley & Sons), both incorporated entirely by reference. There are a variety of techniques that may be used to efficiently generate DNA encoding CTLA4-Ig immunoadhesins disclosed herein. Such methods include but are not limited to gene assembly methods, PCR-based method and methods which use variations of PCR, ligase chain reaction-based methods, pooled oligo methods such as those used in synthetic shuffling, error-prone amplification methods and methods which use oligos with random mutations, classical site-directed mutagenesis methods, cassette mutagenesis, and other amplification and gene synthesis methods. As is known in the art, there are a variety of commercially available kits and methods for gene assembly, mutagenesis, vector subcloning, and the like, and such commercial products find use in for generating nucleic acids that encode CTLA4-Ig immunoadhesins.

The CTLA4-Ig immunoadhesin proteins disclosed herein may be produced by culturing a host cell transformed with nucleic acid, e.g., an expression vector, containing nucleic acid encoding the CTLA4-Ig immunoadhesins, under the appropriate conditions to induce or cause expression of the protein. The conditions appropriate for expression will vary with the choice of the expression vector and the host cell, and will be easily ascertained by one skilled in the art through routine experimentation. A wide variety of appropriate host cells may be used, including but not limited to mammalian cells, bacteria, insect cells, yeast, and plant cells. For example, a variety of cell lines that may find use in generating CTLA4-Ig immunoadhesins disclosed herein are described in the ATCC® cell line catalog, available from the American Type Culture Collection.

In one embodiment, the CTLA4-Ig immunoadhesins are expressed in mammalian expression systems, including systems in which the expression constructs are introduced into the mammalian cells using virus such as retrovirus or adenovirus. Any mammalian cells may be used, e.g., human, mouse, rat, hamster, and primate cells. Suitable cells also include known research cells, including but not limited to Jurkat T cells, NIH3T3, CHO, BHK, COS, HEK293, PER C.6, HeLa, Sp2/0, NS0 cells and variants thereof. In an alternate embodiment, library proteins are expressed in bacterial cells. Bacterial expression systems are well known in the art, and include *Escherichia coli* (*E. coli*), *Bacillus subtilis*, *Streptococcus cremoris*, and *Streptococcus lividans*. In alternate embodiments, CTLA4-Ig immunoadhesins are produced in insect cells (e.g. Sf21/Sf9, *Trichoplusia ni* Bti-Tn5b1-4) or yeast cells (e.g. *S. cerevisiae, Pichia*, etc). In an alternate embodiment, CTLA4-Ig immunoadhesins are expressed in vitro using cell free translation systems. In vitro translation systems derived from both prokaryotic (e.g. *E. coli*) and eukaryotic (e.g. wheat germ, rabbit reticulocytes) cells are available and may be chosen based on the expression levels and functional properties of the protein of interest. For example, as appreciated by those skilled in the art, in vitro translation is required for some display technologies, for example ribosome display. In addition, the CTLA4-Ig immunoadhesins may be produced by chemical synthesis methods. Also transgenic expression systems both animal (e.g. cow, sheep or goat milk, embryonated hen's eggs, whole insect larvae, etc.) and plant (e.g. corn, tobacco, duckweed, etc.)

The nucleic acids that encode the CTLA4-Ig immunoadhesins disclosed herein may be incorporated into an expression vector in order to express the protein. A variety of expression vectors may be utilized for protein expression. Expression vectors may comprise self-replicating extra-chromosomal vectors or vectors which integrate into a host genome. Expression vectors are constructed to be compatible with the host cell type. Thus expression vectors which find use in generating CTLA4-Ig immunoadhesins disclosed herein include but are not limited to those which enable protein expression in mammalian cells, bacteria, insect cells, yeast, and in in vitro systems. As is known in the art, a variety of expression vectors are available, commercially or otherwise, that may find use for expressing CTLA4-Ig immunoadhesins disclosed herein.

Expression vectors typically comprise a protein operably linked with control or regulatory sequences, selectable markers, any fusion partners, and/or additional elements. By "operably linked" herein is meant that the nucleic acid is placed into a functional relationship with another nucleic acid sequence. Generally, these expression vectors include transcriptional and translational regulatory nucleic acid operably linked to the nucleic acid encoding the CTLA4-Ig immunoadhesin, and are typically appropriate to the host cell used to express the protein. In general, the transcriptional and translational regulatory sequences may include promoter sequences, ribosomal binding sites, transcriptional start and stop sequences, translational start and stop sequences, and enhancer or activator sequences. As is also known in the art, expression vectors typically contain a selection gene or marker to allow the selection of transformed host cells containing the expression vector. Selection genes are well known in the art and will vary with the host cell used.

CTLA4-Ig immunoadhesins may be operably linked to a fusion partner to enable targeting of the expressed protein, purification, screening, display, and the like. Fusion partners may be linked to the CTLA4-Ig immunoadhesin sequence via a linker sequences. The linker sequence will generally comprise a small number of amino acids, typically less than ten, although longer linkers may also be used. Typically, linker sequences are selected to be flexible and resistant to degradation. As will be appreciated by those skilled in the art, any of a wide variety of sequences may be used as linkers. For example, a common linker sequence comprises the amino acid sequence GGGGS [SEQ ID NO: 40]. A fusion partner may be a targeting or signal sequence that directs CTLA4-Ig immunoadhesin and any associated fusion partners to a desired cellular location or to the extracellular media. As is known in the art, certain signaling sequences may target a protein to be either secreted into the growth media, or into the periplasmic space, located between the inner and outer membrane of the cell. A fusion partner may also be a sequence that encodes a peptide or protein that enables purification and/or screening. Such fusion partners include but are not limited to polyhistidine tags (His-tags) (for example H6 and H10 or other tags for use with Immobilized Metal Affinity Chromatography (IMAC) systems (e.g. Ni+2 affinity columns)), GST fusions, MBP fusions, Strep-tag, the BSP biotinylation target sequence of the bacterial enzyme BirA, and epitope tags which are targeted by antibodies (for example c-myc tags, flag-tags, and the like). As will be appreciated by those skilled in the art, such tags may be useful for purification, for screening, or both. For example, an CTLA4-Ig immunoadhesin may be purified using a His-tag by immobilizing it to a Ni+2 affinity column, and then after purification the same His-tag may be used to immobilize the antibody to a Ni+2 coated plate to perform an ELISA or other binding assay (as described below). A fusion partner may enable the use of a selection method to screen CTLA4-Ig immunoadhesins (see below). Fusion partners that enable a variety of selection methods are well-known in the art.

In one embodiment, CTLA4-Ig immunoadhesins are purified or isolated after expression. Proteins may be isolated or purified in a variety of ways known to those skilled in the art. Purification may be particularly useful in the invention for separating heterodimeric heavy chain species from homodimeric heavy chain species, as described herein. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, isoelectric focusing, immunological, precipitation, dialysis, and chromatofocusing techniques. Ultrafiltration and diafiltration techniques, in conjunction with protein concentration, are also useful. As is well known in the art, a variety of natural proteins bind Fc and antibodies, and these proteins can find use for purification of CTLA4-Ig immunoadhesins disclosed herein. For example, the bacterial proteins A and G bind to the Fc region. Likewise, the bacterial protein L binds to the Fab region of some antibodies, as of course does the antibody's target antigen. Purification can often be enabled by a particular fusion partner. For example, CTLA4-Ig immunoadhesins may be purified using glutathione resin if a GST fusion is employed, Ni+2 affinity chromatography if a His-tag is employed, or immobilized anti-flag antibody if a flag-tag is used. For general guidance in suitable purification techniques, see, e.g. incorporated entirely by reference Protein Purification: Principles and Practice, 3rd Ed., Scopes, Springer-Verlag, NY, 1994, incorporated entirely by reference. The degree of purification necessary will vary depending on the screen or use of the CTLA4-Ig immunoadhesins. In some instances no purification is necessary. For example in one embodiment, if the CTLA4-Ig immunoadhesins are secreted, screening may take place directly from the media. As is well known in the art, some methods of selection do not involve purification of proteins.

In Vitro Experimentation

CTLA4-Ig immunoadhesins may be tested experimentally using a variety of in vitro methods, including but not limited to those that use binding assays, cell-based assays, and selection technologies. Automation and high-throughput screening technologies may be utilized in the screening procedures. Screening may employ the use of a fusion partner or label. The use of fusion partners has been discussed above. By "labeled" herein is meant that the CTLA4-Ig immunoadhesins disclosed herein have one or more elements, isotopes, or chemical compounds attached to enable the detection in a screen. In general, labels fall into three classes: a) immune labels, which may be an epitope incorporated as a fusion partner that is recognized by an antibody, b) isotopic labels, which may be radioactive or heavy isotopes, and c) small molecule labels, which may include fluorescent and colorimetric dyes, or molecules such as biotin that enable other labeling methods. Labels may be incorporated into the compound at any position and may be incorporated in vitro or in vivo during protein expression.

In one embodiment, the functional and/or biophysical properties of CTLA4-Ig immunoadhesins are screened in an in vitro assay. In vitro assays may allow a broad dynamic range for screening properties of interest. Particularly relevant for the present invention, the CTLA4-Ig immunoadhesins may be tested for their affinity for one or more antigens. Properties that may be screened include but are not limited to stability, solubility, and affinity for Fc ligands, for example FcγRs. Multiple properties may be screened simultaneously or individually. Proteins may be purified or unpurified, depending on the requirements of the assay. In one embodiment, the screen is a qualitative or quantitative binding assay for binding of CTLA4-Ig immunoadhesins to a protein or nonprotein molecule that is known or thought to bind the CTLA4-Ig immunoadhesin. In one embodiment, the screen is a binding assay for measuring binding to the target antigen. In an alternate embodiment, the screen is an assay for binding of CTLA4-Ig immunoadhesins to an Fc ligand, including but are not limited to the family of FcγRs, the neonatal receptor FcRn, the complement protein C1q, and the bacterial proteins A and G. Said Fc ligands may be from any organism. In one embodiment, Fc ligands are from humans, mice, rats, rabbits, and/or monkeys. Binding assays can be carried out using a variety of methods known in the art, including but not limited to FRET (Fluorescence Resonance Energy Transfer) and BRET (Bioluminescence Resonance Energy Transfer)-based assays, AlphaScreen™ (Amplified Luminescent Proximity Homogeneous Assay), Scintillation Proximity Assay, ELISA (Enzyme-Linked Immunosorbent Assay), SPR (Surface Plasmon Resonance, also known as BIACORE®), isothermal titration calorimetry, differential scanning calorimetry, gel electrophoresis, and chromatography including gel filtration. These and other methods may take advantage of some fusion partner or label of the CTLA4-Ig immunoadhesin. Assays may employ a variety of detection methods including but not limited to chromogenic, fluorescent, luminescent, or isotopic labels.

The biophysical properties of CTLA4-Ig immunoadhesins, for example stability and solubility, may be tested using a variety of methods known in the art. Protein stability may be determined by measuring the thermodynamic equilibrium between folded and unfolded states. For example, CTLA4-Ig immunoadhesins disclosed herein may be unfolded using chemical denaturant, heat, or pH, and this transition may be monitored using methods including but not limited to circular dichroism spectroscopy, fluorescence spectroscopy, absorbance spectroscopy, NMR spectroscopy, calorimetry, and proteolysis. As will be appreciated by those skilled in the art, the kinetic parameters of the folding and unfolding transitions may also be monitored using these and other techniques. The solubility and overall structural integrity of an CTLA4-Ig immunoadhesin may be quantitatively or qualitatively determined using a wide range of methods that are known in the art. Methods which may find use for characterizing the biophysical properties of CTLA4-Ig immunoadhesins disclosed herein include gel electrophoresis, isoelectric focusing, capillary electrophoresis, chromatography such as size exclusion chromatography, ion-exchange chromatography, and reversed-phase high performance liquid chromatography, peptide mapping, oligosaccharide mapping, mass spectrometry, ultraviolet absorbance spectroscopy, fluorescence spectroscopy, circular dichroism spectroscopy, isothermal titration calorimetry, differential scanning calorimetry, analytical ultra-centrifugation, dynamic light scattering, proteolysis, and cross-linking, turbidity measurement, filter retardation assays, immunological assays, fluorescent dye binding assays, protein-staining assays, microscopy, and detection of aggregates via ELISA or other binding assay. Structural analysis employing X-ray crystallographic techniques and NMR spectroscopy may also find use. In one embodiment, stability and/or solubility may be measured by determining the amount of protein solution after some defined period of time. In this assay, the protein may or may not be exposed to some extreme condition, for example elevated temperature, low pH, or the presence of denaturant. Because function typically requires a stable, soluble, and/or well-folded/structured protein, the aforementioned functional and binding assays also provide ways to perform such a measurement. For example, a solution comprising an CTLA4-Ig immunoadhesin could be assayed for its ability to bind target antigen, then exposed to elevated temperature for one or more defined periods of time, then assayed for antigen binding again. Because unfolded and aggregated protein is not expected to be capable of binding antigen, the amount of activity remaining provides a measure of the CTLA4-Ig immunoadhesin's stability and solubility.

In one embodiment, CTLA4-Ig immunoadhesins may be tested using one or more cell-based or in vitro assays. For such assays, CTLA4-Ig immunoadhesins, purified or unpurified, are typically added exogenously such that cells are exposed to CTLA4-Ig immunoadhesins described herein. These assays are typically, but not always, based on the biology of the ability of the CTLA4-Ig immunoadhesin to bind to the target antigen and mediate some biochemical event, for example effector functions like cellular lysis, phagocytosis, ligand/receptor binding inhibition, inhibition of growth and/or proliferation, inhibition of calcium release and/or signaling, apoptosis and the like. Such assays often involve monitoring the response of cells to CTLA4-Ig immunoadhesin, for example cell survival, cell death, cellular phagocytosis, cell lysis, change in cellular morphology, or transcriptional activation such as cellular expression of a natural gene or reporter gene. For example, such assays may measure the ability of CTLA4-Ig immunoadhesins to elicit cell killing, for example ADCC, ADCP, and CDC. Assays that measure cellular killing that is mediated by co-engagement of antigens are particularly relevant for the invention. For some assays additional cells or components, that is in addition to the target cells, may need to be added, for example serum complement, or effector cells such as peripheral blood monocytes (PBMCs), NK cells, macrophages, T cells, and the like. Such additional cells may be from any organism, e.g., humans, mice, rat, rabbit, and monkey. Crosslinked or monomeric antibodies may cause apoptosis of certain cell lines expressing the antibody's target antigen, or they may mediate attack on target cells by immune cells which have been added to the assay. Methods for monitoring cell death or viability are known in the art, and include the use of dyes, fluorophores, immunochemical, cytochemical, and radioactive reagents. For example, caspase assays or annexin-flourconjugates may enable apoptosis to be measured, and uptake or release of radioactive substrates (e.g. Chromium-51 release assays) or the metabolic reduction of fluorescent dyes such as alamar blue may enable cell growth, proliferation or activation to be monitored. In one embodiment, the DELFIA EuTDA-based cytotoxicity assay (Perkin Elmer, Mass.) is used. Alternatively, dead or damaged target cells may be monitored by measuring the release of one or more natural intracellular proteins, for example lactate dehydrogenase. Transcriptional activation may also serve as a method for assaying function in cell-based assays. In this case, response may be monitored by assaying for natural genes or proteins which may be upregulated or down-regulated, for example the release of certain interleukins may be measured, or alternatively readout may be via a luciferase or GFP-reporter construct. Cell-based assays may also involve the measure of morphological changes of cells as a response to the presence of an CTLA4-Ig immunoadhesin. Cell types for such assays may be prokaryotic or eukaryotic, and a variety of cell lines that are known in the art may be employed. Alternatively, cell-based screens are performed using cells that have been transformed or transfected with nucleic acids encoding the CTLA4-Ig immunoadhesins.

In Vivo Experimentation

The biological properties of the CTLA4-Ig immunoadhesins disclosed herein may be characterized in cell, tissue, and whole organism experiments.

As shown herein, in general, testing of binding and associated affinities of the variant CTLA4 domains of the immunoadhesins of the invention is done using binding assays as outlined in the examples, As described above, affinity may be described as being enhanced when the KA of a variant polypeptide relative to parent polypeptide is significantly higher or the KD of a variant polypeptide is significantly lower relative to a parent polypeptide. When expressed in terms of a ratio, for example, KA (variant polypeptide)/KA (parent polypeptide) or KD (parent polypeptide)/KD (variant polypeptide), a significant increase in affinity is witnessed, for example, when one and/or both of these ratios is about 1.2, 1.5, 2.0, 3, 4, 5, 6, 7, 8, 9, 10, 11, 12, 13, 14, 15, 16, 17, 18, 19, 20, 25, 30, 35, 40, 50, 100, 250, 500, 1000 or more.

As is known in the art, drugs are often tested in animals, including but not limited to mice, rats, rabbits, dogs, cats, pigs, and monkeys, in order to measure a drug's efficacy for treatment against a disease or disease model, or to measure a drug's pharmacokinetics, toxicity, and other properties. Said animals may be referred to as disease models. With respect to the CTLA4-Ig immunoadhesins disclosed herein, a particular challenge arises when using animal models to evaluate the potential for in-human efficacy of candidate polypeptides—this is due, at least in part, to the fact that the Fc domains of the CTLA4-Ig immunoadhesins that have a specific effect on the affinity for a human Fc receptor may not have a similar affinity effect with the orthologous animal receptor. These problems can be further exacerbated by the inevitable ambiguities associated with correct assignment of true orthologues (Mechetina et al., 2002, Immunogenetics 54:463-468, incorporated entirely by reference), and the fact that some orthologues simply do not exist in the animal. Therapeutics are often tested in mice, including but not limited to nude mice, Rag-deficient mice, SCID mice, xenograft mice, and transgenic mice (including knockins and knockouts). Therapeutic CTLA4-Ig immunoadhesins herein can be tested in mouse strains NZB, NOD, BXSB, MRL/Ipr, K/BxN and transgenics (including knockins and knockouts). Such mice can develop various autoimmune conditions that resemble human organ specific, systemic autoimmune or inflammatory disease pathologies such as systemic lupus erythematosus (SLE) and rheumatoid arthritis (RA). For example, an CTLA4-Ig immunoadhesin disclosed herein intended for autoimmune diseases may be tested in such mouse models by treating the mice to determine the ability of the CTLA4-Ig immunoadhesin to reduce or inhibit the development of the disease pathology. Because of the incompatibility between the mouse and human Fcγ receptor system, an alternative approach is to use a murine SCID model in which immune deficient mice are engrafted with human PBLs or PBMCs (huPBL-SCID, huPBMC-SCID) providing a semi-functional human immune system with human effector cells and Fc receptors. Other organisms, e.g., mammals, may also be used for testing. For example, because of their genetic similarity to humans, monkeys can be suitable therapeutic models, and thus may be used to test the efficacy, toxicity, pharmacokinetics, or other property of the CTLA4-Ig immunoadhesins disclosed herein. Tests of the CTLA4-Ig immunoadhesins disclosed herein in humans are ultimately required for approval as drugs, and thus of course these experiments are contemplated. Thus the CTLA4-Ig immunoadhesins disclosed herein may be tested in humans to determine their therapeutic efficacy, toxicity, pharmacokinetics, and/or other clinical properties.

In some embodiments, CTLA4-Ig immunoadhesins disclosed herein may be assessed for efficacy in clinically relevant animal models of various human diseases. In many cases, relevant models include various transgenic animals for specific antigens and receptors.

In one embodiment, the testing of CTLA4-Ig immunoadhesins may include study of efficacy in primates (e.g. cynomolgus monkey model) to facilitate the evaluation of depletion of specific target cells harboring the target antigen. Additional primate models include but are not limited to use of the rhesus monkey to assess CTLA4-Ig immunoadhesins in therapeutic studies of autoimmune, transplantation and cancer.

Toxicity studies are performed to determine drug related-effects that cannot be evaluated in standard pharmacology profiles, or occur only after repeated administration of the agent. Most toxicity tests are performed in two species—a rodent and a non-rodent—to ensure that any unexpected adverse effects are not overlooked before new therapeutic entities are introduced into man. In general, these models may measure a variety of toxicities including genotoxicity, chronic toxicity, immunogenicity, reproductive/developmental toxicity and carcinogenicity. Included within the aforementioned parameters are standard measurement of food consumption, bodyweight, antibody formation, clinical chemistry, and macro- and microscopic examination of standard organs/tissues (e.g. cardiotoxicity). Additional parameters of measurement are injection site trauma and the measurement of neutralizing antibodies, if any. Traditionally, monoclonal antibody therapeutics, naked or conjugated, are evaluated for cross-reactivity with normal tissues, immunogenicity/antibody production, conjugate or linker toxicity and "bystander" toxicity of radiolabelled species. Nonetheless, such studies may have to be individualized to address specific concerns and following the guidance set by ICH S6 (Safety studies for biotechnological products, also noted above). As such, the general principles are that the products are sufficiently well characterized, impurities/contaminants have been removed, that the test material is comparable throughout development, that GLP compliance is maintained.

The pharmacokinetics (PK) of the CTLA4-Ig immunoadhesins disclosed herein may be studied in a variety of animal systems, with the most relevant being non-human primates such as the cynomolgus and rhesus monkeys. Single or repeated i.v./s.c. administrations over a dose range of 6000-fold (0.05-300 mg/kg) can be evaluated for half-life (days to weeks) using plasma concentration and clearance. Volume of distribution at a steady state and level of systemic absorbance can also be measured. Examples of such parameters of measurement generally include maximum observed plasma concentration (Cmax), the time to reach Cmax (Tmax), the area under the plasma concentration-time curve from time 0 to infinity [AUC(0-inf] and apparent elimination half-life (T½). Additional measured parameters could include compartmental analysis of concentration-time data obtained following i.v. administration and bioavailability.

Pharmacodynamic studies may include, but are not limited to, targeting specific cells or blocking signaling mechanisms, measuring inhibition of antigen-specific antibodies etc. The CTLA4-Ig immunoadhesins disclosed herein may target particular effector cell populations and thereby be direct drugs to induce certain activities to improve potency or to increase penetration into a particularly favorable physiological compartment. Such pharmacodynamic effects may be demonstrated in animal models or in humans.

Clinical Use

The CTLA4-Ig immunoadhesins disclosed herein may find use in a wide range of products. In one embodiment an CTLA4-Ig immunoadhesin disclosed herein is a therapeutic, a diagnostic, or a research reagent. The CTLA4-Ig immunoadhesins may find use in a composition that is monoclonal or polyclonal. The CTLA4-Ig immunoadhesins disclosed herein may be used for therapeutic purposes. The CTLA4-Ig immunoadhesins may be administered to a patient to treat disorders.

A "patient" for the purposes disclosed herein includes both humans and other animals, e.g., other mammals. Thus the CTLA4-Ig immunoadhesins disclosed herein have both human therapy and veterinary applications. The term "treatment" or "treating" as disclosed herein is meant to include therapeutic treatment, as well as prophylactic, or suppressive measures for a disease or disorder. Thus, for example, successful administration of an CTLA4-Ig immunoadhesin prior to onset of the disease results in treatment of the disease. As another example, successful administration of an optimized CTLA4-Ig immunoadhesin after clinical manifestation of the disease to combat the symptoms of the disease comprises treatment of the disease. "Treatment" and "treating" also encompasses administration of an optimized CTLA4-Ig immunoadhesin after the appearance of the disease in order to eradicate the disease. Successful administration of an agent after onset and after clinical symptoms have developed, with possible abatement of clinical symptoms and perhaps amelioration of the disease, comprises treatment of the disease. Those "in need of treatment" include mammals already having the disease or disorder, as well as those prone to having the disease or disorder, including those in which the disease or disorder is to be prevented.

The CTLA4-Ig immunoadhesins herein are preferably used to treat an immune related condition or disorder. Immune related conditions include but are not limited to autoimmune diseases, inflammatory disorders, and prevention of immune response associated with rejection of donor tissue.

The CTLA4-Ig immunoadhesins herein may be used to treat autoimmune diseases. "Autoimmune diseases" herein include allogenic islet graft rejection, alopecia areata, ankylosing spondylitis, antiphospholipid syndrome, autoimmune Addison's disease, antineutrophil cytoplasmic autoantibodies (ANCA), autoimmune diseases of the adrenal gland, autoimmune hemolytic anemia, autoimmune hepatitis, autoimmune myocarditis, autoimmune neutropenia, autoimmune oophoritis and orchitis, autoimmune thrombocytopenia, autoimmune urticaria, Behcet's disease, bullous pemphigoid, cardiomyopathy, Castleman's syndrome, celiac spruce-dermatitis, chronic fatigue immune disfunction syndrome, chronic inflammatory demyelinating polyneuropathy, Churg-Strauss syndrome, cicatrical pemphigoid, CREST syndrome, cold agglutinin disease, Crohn's disease, dermatomyositis, discoid lupus, essential mixed cryoglobulinemia, factor VIII deficiency, fibromyalgia-fibromyositis, glomerulonephritis, Grave's disease, Guillain-Barre, Goodpasture's syndrome, graft-versus-host disease (GVHD), Hashimoto's thyroiditis, hemophilia A, idiopathic pulmonary fibrosis, idiopathic thrombocytopenia purpura (ITP), IgA neuropathy, IgM polyneuropathies, immune mediated thrombocytopenia, juvenile arthritis, Kawasaki's disease, lichen plantus, lupus erthematosis, Meniere's disease, mixed connective tissue disease, multiple sclerosis, type 1 diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobinulinemia, primary biliary cirrhosis, psoriasis, psoriatic arthritis, Reynauld's phenomenon, Reiter's syndrome, rheumatoid arthritis, sarcoidosis, scleroderma, Sjorgen's syndrome, solid organ transplant rejection, stiff-man syndrome, systemic lupus erythematosus, takayasu arteritis, temporal arteristis/giant cell arteritis, thrombotic thrombocytopenia purpura, ulcerative colitis, uveitis, vasculitides such as dermatitis herpetiformis vasculitis, vitiligo, and Wegner's granulomatosis.

The CTLA4-Ig immunoadhesins herein may be used to treat inflammatory disorders. "Inflammatory disorders" herein include acute respiratory distress syndrome (ARDS), acute septic arthritis, adjuvant arthritis, juvenile idiopathic arthritis, allergic encephalomyelitis, allergic rhinitis, allergic vasculitis, allergy, asthma, atherosclerosis, chronic inflammation due to chronic bacterial or viral infectionis, chronic obstructive pulmonary disease (COPD), coronary artery disease, encephalitis, inflammatory bowel disease, inflammatory osteolysis, inflammation associated with acute and delayed hypersensitivity reactions, inflammation associated with tumors, peripheral nerve injury or demyelinating diseases, inflammation associated with tissue trauma such as burns and ischemia, inflammation due to meningitis, multiple organ injury syndrome, pulmonary fibrosis, sepsis and septic shock, Stevens-Johnson syndrome, undifferentiated arthropy, and undifferentiated spondyloarthropathy.

The CTLA4-Ig immunoadhesins herein may be used to prevent or suppressing an immune response associated with rejection of a donor tissue, cell, graft, or organ transplant by a recipient subject. Graft-related diseases or disorders include graft versus host disease (GVDH), such as associated with bone marrow transplantation, and immune disorders resulting from or associated with rejection of organ, tissue, or cell graft transplantation (e.g., tissue or cell allografts or xenografts), including, e.g., grafts of skin, muscle, neurons, islets, organs, parenchymal cells of the liver, etc. With regard to a donor tissue, cell, graft or solid organ transplant in a recipient subject, it is believed such molecules of the invention disclosed herein (e.g., variant CTLA-4 ECD polypeptide or variant CTLA-4-Ig fusion protein) may be effective in preventing acute rejection of such transplant in the recipient and/or for long-term maintenance therapy to prevent rejection of such transplant in the recipient (e.g., inhibiting rejection of insulin-producing islet cell transplant from a donor in the subject recipient suffering from diabetes).

Preferred immune related disorders that may be treated by the CTLA4-Ig immunoadhesins disclosed herein include Crohn's disease, systemic lupus erythematosus (SLE), lupus nephritis, psoriatic arthritis, psoriasis, rheumatoid arthritis, ulcerative colitis, and transplant rejection, including but not limited to kidney transplant, liver transplant, and pancreatic transplant.

The CTLA4-Ig immunoadhesins herein may be used to treat cancer. "Cancer" and "cancerous" herein refer to or describe the physiological condition in mammals that is typically characterized by unregulated cell growth. Examples of cancer include but are not limited to carcinoma, lymphoma, blastoma, sarcoma (including liposarcoma), neuroendocrine tumors, mesothelioma, schwanoma, meningioma, adenocarcinoma, melanoma, and leukemia or lymphoid malignancies.

The CTLA4-Ig immunoadhesins herein may be used to treat infectious diseases. By "infectious diseases" herein include diseases caused by pathogens such as viruses, bacteria, fungi, protozoa, and parasites.

Furthermore, CTLA4-Ig immunoadhesins disclosed herein may be used to prevent or treat additional conditions including but not limited to heart conditions such as congestive heart failure (CHF), myocarditis and other conditions of the myocardium; skin conditions such as rosecea, acne, and eczema; bone and tooth conditions such as bone loss, osteoporosis, Paget's disease, Langerhans' cell histiocytosis, periodontal disease, disuse osteopenia, osteomalacia, monostotic fibrous dysplasia, polyostotic fibrous dysplasia, bone metastasis, bone pain management, humoral malignant hypercalcemia, periodontal reconstruction, spinal cord injury, and bone fractures; metabolic conditions such as Gaucher's disease; endocrine conditions such as Cushing's syndrome; and neurological and neurodegenerative conditions such as Alzheimer's disease.

Formulation

Pharmaceutical compositions are contemplated wherein an CTLA4-Ig immunoadhesin disclosed herein and one or more therapeutically active agents are formulated. Formulations of the CTLA4-Ig immunoadhesins disclosed herein are prepared for storage by mixing said CTLA4-Ig immunoadhesin having the desired degree of purity with optional pharmaceutically acceptable carriers, excipients or stabilizers (Remington's Pharmaceutical Sciences 16th edition, Osol, A. Ed., 1980, incorporated entirely by reference), in the form of lyophilized formulations or aqueous solutions. Acceptable carriers, excipients, or stabilizers are nontoxic to recipients at the dosages and concentrations employed, and include buffers such as phosphate, citrate, acetate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or CTLA4-Ig immunoadhesins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; sweeteners and other flavoring agents; fillers such as microcrystalline cellulose, lactose, corn and other starches; binding agents; additives; coloring agents; salt-forming counter-ions such as sodium; metal complexes (e.g. Zn-protein complexes); and/or non-ionic surfactants such as TWEEN™, PLURONICS™ or polyethylene glycol (PEG). In one embodiment, the pharmaceutical composition that comprises the CTLA4-Ig immunoadhesin disclosed herein may be in a water-soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Some embodiments include at least one of the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine. The formulations to be used for in vivo administration may be sterile. This is readily accomplished by filtration through sterile filtration membranes or other methods.

The CTLA4-Ig immunoadhesins disclosed herein may also be formulated as immunoliposomes. A liposome is a small vesicle comprising various types of lipids, phospholipids and/or surfactant that is useful for delivery of a therapeutic agent to a mammal. Liposomes containing the CTLA4-Ig immunoadhesin are prepared by methods known in the art. The components of the liposome are commonly arranged in a bilayer formation, similar to the lipid arrangement of biological membranes. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The CTLA4-Ig immunoadhesin and other therapeutically active agents may also be entrapped in microcapsules prepared by methods including but not limited to coacervation techniques, interfacial polymerization (for example using hydroxymethylcellulose or gelatin-microcapsules, or poly-(methylmethacylate) microcapsules), colloidal drug delivery systems (for example, liposomes, albumin microspheres, microemulsions, nano-particles and nanocapsules), and macroemulsions. Such techniques are disclosed in Remington's Pharmaceutical Sciences 16th edition, Osol, A. Ed., 1980, incorporated entirely by reference. Sustained-release preparations may be prepared. Suitable examples of sustained-release preparations include semipermeable matrices of solid hydrophobic polymer, which matrices are in the form of shaped articles, e.g. films, or microcapsules. Examples of sustained-release matrices include polyesters, hydrogels (for example poly(2-hydroxyethyl-methacrylate), or poly(vinylalcohol)), polylactides, copolymers of L-glutamic acid and gamma ethyl-L-glutamate, non-degradable ethylene-vinyl acetate, degradable lactic acid-glycolic acid copolymers such as the Lupron Depot® (which are injectable microspheres composed of lactic acid-glycolic acid copolymer and leuprolide acetate), poly-D-(−)-3-hydroxybutyric acid, and Pro-Lease® (commercially available from Alkermes), which is a microsphere-based delivery system composed of the desired bioactive molecule incorporated into a matrix of poly-DL-lactide-co-glycolide (PLG).

Administration

Administration of the pharmaceutical composition comprising an CTLA4-Ig immunoadhesin disclosed herein, e.g., in the form of a sterile aqueous solution, may be done in a variety of ways, including, but not limited to orally, subcutaneously, intravenously, intranasally, intraotically, transdermally, topically (e.g., gels, salves, lotions, creams, etc.), intraperitoneally, intramuscularly, intrapulmonary, vaginally, parenterally, rectally, or intraocularly. In some instances, for example for the treatment of wounds, inflammation, etc., the CTLA4-Ig immunoadhesin may be directly applied as a solution or spray. As is known in the art, the pharmaceutical composition may be formulated accordingly depending upon the manner of introduction.

Subcutaneous administration may be used in circumstances where the patient may self-administer the pharmaceutical composition. Many protein therapeutics are not sufficiently potent to allow for formulation of a therapeutically effective dose in the maximum acceptable volume for subcutaneous administration. This problem may be addressed in part by the use of protein formulations comprising arginine-HCl, histidine, and polysorbate. CTLA4-Ig immunoadhesins disclosed herein may be more amenable to subcutaneous administration due to, for example, increased potency, improved serum half-life, or enhanced solubility. As is known in the art, protein therapeutics are often delivered by IV infusion or bolus. The CTLA4-Ig immunoadhesins disclosed herein may also be delivered using such methods. For example, administration may be by intravenous infusion with 0.9% sodium chloride as an infusion vehicle.

Pulmonary delivery may be accomplished using an inhaler or nebulizer and a formulation comprising an aerosolizing agent. For example, AERx® inhalable technology commercially available from Aradigm, or Inhance™ pulmonary delivery system commercially available from Nektar Therapeutics may be used. Furthermore, CTLA4-Ig immunoadhesins disclosed herein may be amenable to oral delivery.

In addition, any of a number of delivery systems are known in the art and may be used to administer the CTLA4-Ig immunoadhesins disclosed herein. Examples include, but are not limited to, encapsulation in liposomes, microparticles, microspheres (e.g., PLA/PGA microspheres), and the like. Alternatively, an implant of a porous, non-porous, or gelatinous material, including membranes or fibers, may be used. Sustained release systems may comprise a polymeric material or matrix such as polyesters, hydrogels, poly(vinylalcohol), polylactides, copolymers of L-glutamic acid and ethyl-L-glutamate, ethylene-vinyl acetate, lactic acid-glycolic acid copolymers such as the Lupron Depot®, and poly-D-(−)-3-hydroxybutyric acid. It is also possible to administer a nucleic acid encoding an CTLA4-Ig immunoadhesin disclosed herein, for example by retroviral infection, direct injection, or coating with lipids, cell surface receptors, or other transfection agents. In all cases, controlled release systems may be used to release the CTLA4-Ig immunoadhesin at or close to the desired location of action.

Dosing

The dosing amounts and frequencies of administration are, in one embodiment, selected to be therapeutically or prophylactically effective. As is known in the art, adjustments for protein degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

The concentration of the therapeutically active CTLA4-Ig immunoadhesin in the formulation may vary from about 0.1 to 100 weight %. In one embodiment, the concentration of the CTLA4-Ig immunoadhesin is in the range of 0.003 to 1.0 molar. In order to treat a patient, a therapeutically effective dose of the CTLA4-Ig immunoadhesin disclosed herein may be administered. By "therapeutically effective dose" herein is meant a dose that produces the effects for which it is administered. The exact dose will depend on the purpose of the treatment, and will be ascertainable by one skilled in the art using known techniques. Dosages may range from 0.0001 to 100 mg/kg of body weight or greater, for example 0.1, 1, 10, or 50 mg/kg of body weight. In one embodiment, dosages range from 1 to 10 mg/kg.

In some embodiments, only a single dose of the CTLA4-Ig immunoadhesin is used. In other embodiments, multiple doses of the CTLA4-Ig immunoadhesin are administered. The elapsed time between administrations may be less than 1 hour, about 1 hour, about 1-2 hours, about 2-3 hours, about 3-4 hours, about 6 hours, about 12 hours, about 24 hours, about 48 hours, about 2-4 days, about 4-6 days, about 1 week, about 2 weeks, or more than 2 weeks.

In other embodiments the CTLA4-Ig immunoadhesins disclosed herein are administered in metronomic dosing regimes, either by continuous infusion or frequent administration without extended rest periods. Such metronomic administration may involve dosing at constant intervals without rest periods. Typically such regimens encompass chronic low-dose or continuous infusion for an extended period of time, for example 1-2 days, 1-2 weeks, 1-2 months, or up to 6 months or more. The use of lower doses may minimize side effects and the need for rest periods.

In certain embodiments the CTLA4-Ig immunoadhesins disclosed herein and one or more other prophylactic or therapeutic agents are cyclically administered to the patient. Cycling therapy involves administration of a first agent at one time, a second agent at a second time, optionally additional agents at additional times, optionally a rest period, and then repeating this sequence of administration one or more times. The number of cycles is typically from 2-10. Cycling therapy may reduce the development of resistance to one or more agents, may minimize side effects, or may improve treatment efficacy.

Combination Therapies

The CTLA4-Ig immunoadhesins disclosed herein may be administered concomitantly with one or more other therapeutic regimens or agents. The additional therapeutic regimes or agents may be used to improve the efficacy or safety of the CTLA4-Ig immunoadhesin. Also, the additional therapeutic regimes or agents may be used to treat the same disease or a comorbidity rather than to alter the action of the CTLA4-Ig immunoadhesin. For example, an CTLA4-Ig immunoadhesin disclosed herein may be administered to the patient along with chemotherapy, radiation therapy, or both chemotherapy and radiation therapy.

The terms "in combination with" and "co-administration" are not limited to the administration of said prophylactic or therapeutic agents at exactly the same time. Instead, it is meant that the CTLA4-Ig immunoadhesin disclosed herein and the other agent or agents are administered in a sequence and within a time interval such that they may act together to provide a benefit that is increased versus treatment with only either the CTLA4-Ig immunoadhesin disclosed herein or the other agent or agents. In some embodiments, CTLA4-Ig immunoadhesins disclosed herein and the other agent or agents act additively, and sometimes synergistically. Such molecules are suitably present in combination in amounts that are effective for the purpose intended. The skilled medical practitioner can determine empirically, or by considering the pharmacokinetics and modes of action of the agents, the appropriate dose or doses of each therapeutic agent, as well as the appropriate timings and methods of administration.

The CTLA4-Ig immunoadhesin disclosed herein may be administered in combination with one or more other prophylactic or therapeutic agents, including but not limited to cytotoxic agents, chemotherapeutic agents, antibiotics, antifungal agents, antiviral agents, cytokines, growth inhibitory agents, anti-hormonal agents, kinase inhibitors, anti-angiogenic agents, cardioprotectants, immunostimulatory agents, immunosuppressive agents, agents that promote proliferation of hematological cells, angiogenesis inhibitors, protein tyrosine kinase (PTK) inhibitors, other antibodies, Fc fusions, or CTLA4-Ig immunoadhesins, or other therapeutic agents. The therapies of the invention may be combined with other immunotherapies. The therapies of the invention may be combined with antagonists of chemokines or cytokines, including but not limited to antibodies and Fc fusions.

The CTLA4-Ig immunoadhesins disclosed herein may be combined with other therapeutic regimens. For example, in one embodiment, the patient to be treated with an CTLA4-Ig immunoadhesin disclosed herein may also receive radiation therapy. Radiation therapy can be administered according to protocols commonly employed in the art and known to the skilled artisan. Such therapy includes but is not limited to cesium, iridium, iodine, or cobalt radiation. The radiation therapy may be whole body irradiation, or may be directed locally to a specific site or tissue in or on the body, such as the lung, bladder, or prostate. Optionally, the radiation therapy may be administered as a single dose or as multiple, sequential doses. The skilled medical practitioner can determine empirically the appropriate dose or doses of radiation therapy useful herein. In accordance with another, an CTLA4-Ig immunoadhesin disclosed herein and one or more other anti-cancer therapies are employed to treat cancer cells ex vivo. It is contemplated that such ex vivo treatment may be useful in bone marrow transplantation and particularly, autologous bone marrow transplantation. For instance, treatment of cells or tissue(s) containing cancer cells with CTLA4-Ig immunoadhesin and one or more other anti-cancer therapies, such as described above, can be employed to deplete or substantially deplete the cancer cells prior to transplantation in a recipient patient. It is of course contemplated that the CTLA4-Ig immunoadhesins disclosed herein may employ in combination with still other therapeutic techniques such as surgery.

Whereas particular embodiments of the invention have been described above for purposes of illustration, it will be appreciated by those skilled in the art that numerous variations of the details may be made without departing from the invention as described in the appended claims. All references cited herein are incorporated in their entirety.

EXAMPLES

Examples are provided below to illustrate the present invention. These examples are not meant to constrain the present invention to any particular application or theory of operation.

Example 1

Engineered CTLA4-Ig Variants that Enhance Binding of B7-1 and B7-2

The amino acid sequence of full length human CTLA4 is provided in FIG. 1. The extracellular domain (ECD) that is responsible for interaction with B7-1 and B7-2 is also provided in FIG. 1.

Immunoadhesins (Fc fusions) of CTLA4 can be constructed by linking the ECD (or some variant of the ECD) to the Fc region of an IgG. The Fc regions of the native human IgG's (IgG1, IgG2, IgG3, and IgG4) are provided in FIG. 2. Although the IgG1 Fc provided in FIG. 2 contains the 356D/358L haplotype, other haplotypic or allotypic forms may be used (for example 356E/358M). The Fc region herein is defined as position 230 to the C-terminus based on the EU numbering scheme. Abatacept is an immunoadhesin of CTLA4 linked to a modified IgG1 containing a P238S substitution (referred to as Fc(IgG1-238S in FIG. 2). The CTLA4-Igimmunoadhesins of the invention may include a serine or proline at position 238 (i.e. CTLA4-Ig immunoadhesins may comprise 238S or 238P). Other variant versions of IgG Fc regions are also provided in FIG. 2, including an IgG2 Fc region with four IgG1 modifications in the lower hinge region (referred to as Fc(IgG2-233E/234L/235L/236G).

The CTLA4 ECD may be linked to an Fc region via a variety of linkers. Linkers used in the present comprise sequences from the human IgG constant chains, including the C-terminal end of the CH1 domain and upper hinge. Exemplary linker sequences based on the natural IgG isotypes are provided in FIG. 3. Modified linkers may be used. An exemplary linker used in the present work is a modified IgG linker (for example an IgG1- or IgG2-based linker) where the cysteines are replaced with serines. Abatacept uses a modified IgG1 linker cysteine to serine substitutions in addition to the insertion of an N-terminal glutamine. Examples of such linkers are also provided in FIG. 3.

Examples of exemplary combinations of linkers and Fc regions used in the present study are provided in FIG. 4. These include the Fc region of abatacept, referred to as Ig(ab), as well as two fusions based on IgG2 Fc regions, referred to as Ig(G2) and Ig(G2-ELLG), which contains the four IgG1 modifications in the lower hinge (233E/234L/235L/236G) built into the IgG2 Fc region. Exemplary CTLA4-Ig immunoadhesins are provided in FIG. 5. These include abatacept, also referred to as CTLA4-Ig(ab), an IgG2 Fc-based version of abatacept referred to as CTLA4-Ig(G2), and belatacept, which is a variant version of abatacept with two substitutions A29Y and L104E in the CTLA4 portion that enhance affinity for B7-1 and B7-2.

In order to enhance the affinity of human CTLA4 for human B7-1 (CD80) and B7-2 (CD86), CTLA4 variants were designed using a rational structure-based approach. High resolution structures are available of the complexes between human CTLA4 and human B7-1 (Stamper et al., 2001, Nature 410:608-611) and B7-2 (Schwartz et al., 2001, Nature 410: 604-608). The library of designed variants is provided as follows: A29K, A29N, A29E, A29W, A29F, A29Y, A29H, A29Q, A29R, T30D, T30V, T30A, T30N, T30E, T30H, T30R, E31I, E31M, E31T, E31V, E31D, R33F, R33T, R33M, R33W, R33I, R33Y, R33L, R33E, R33Q, T35E, T35V, T35M, T35D, T35F, T35Y, A49T, A49F, A49Y, A49W, A49D, A49E, T51V, T51L, T51N, T51H, T51Q, T51E, T51S, T51R, T51D, M53E, M53Q, M53Y, M53W, M53F, M53H, T59V, T59L, T59N, T59Y, T59H, T59Q, T59I, L61D, L61E, L61I, L61A, L61F, L61G, L61H, L61K, L61M, L61N, L61P, L61Q, L61R, L61S, L61T, L61V, L61W, L61Y, D63E, S64K, S64R, S64Y, K93D, K93E, K93F, K93H, K93Q, K93R, K93T, K93V, K93W, K93Y, K93N, K93S, E95D, E95Q, E95Y, E95H, E95L, M97F, M97D, M97N, M97I, M97V, Y98F, Y98W, Y102F, Y102W, Y103F, Y103W, Y103H, Y103D, Y103E, Y103N, Y103Q, L104D, L104E, L104V, L104M, L104Y, L104W, L104F, L104H, G105D, G105E, I106E, and I106Y.

Genes encoding the CTLA4 protein were synthesized commercially (Blue Heron Biotechnologies, Bothell, Wash.), and subcloned into the mammalian expression vector pTT5 (Durocher Y, et al., 2002, Nucleic Acids Res 30[2]: E9), containing the human IgG constant region. Amino acid modifications were constructed on top of the abatacept CTLA4-Ig (ab) construct using site-directed mutagenesis using the QuikChange® site-directed mutagenesis methods (Stratagene, La Jolla Calif.). Belatacept CTLA4(A29Y/L104E)-Ig (ab) was also constructed as a control. All DNA was sequenced to confirm the fidelity of the sequences. Plasmids containing CTLA4-Ig genes were transfected into 293E cells (Durocher Y, et al., 2002, Nucleic Acids Res 30[2]: E9; Biotechnology Research Institute, National Research Council Canada) using Lipofectamine™ (Invitrogen, Carlsbad Calif.) at small (3 ml) scale in E-well plate format, and grown in FreeStyle™ 293 media (Invitrogen, Carlsbad Calif.). After 5 days of growth, the variant proteins were screened for target binding directly from the supernatants. After 5 days of growth, the proteins were purified from the culture supernatant by protein A affinity using the MabSelect™ resin (GE Healthcare).

Variant CTLA4-Ig Fc fusion proteins were screened for binding to B7-1 and B7-2 using surface plasmon resonance. Binding measurements were performed using a Biacore™ 3000 instrument (Biacore). Sensor chips were derivitized with anti-His-tag mAb followed by capture of B7-1-Ig or B7-2-Ig (both from R&D Systems) at 100 nM and 200 nM respectively for 1.5 min. Variant and control CTLA4-Ig proteins in HBS-EP buffer (Biacore) were injected for 1 min followed by a 2 min dissociation. Data were processed by zeroing time and response before the injection of receptor and by subtracting appropriate nonspecific signals (response of reference channel and injection of running buffer). Dissociation sensorgrams were fit using the BIAevaluation software to obtain dissociation rate constants (off-rate or $k_d$ or $k_{off}$). Results from three separate binding experiments are provided in Table 1, along with the fold improvement or reduction in the off-rate for binding to both antigens.

TABLE 1

Off-rates ($k_{off}$) for binding of CTLA4-Ig variants to B7-1 and B7-2

| Variant | B7-1 ($k_{off}$) | B7-2 ($k_{off}$) | Fold B7-1 | Fold B7-2 |
| --- | --- | --- | --- | --- |
| Experiment 1 | | | | |
| Abatacept (WT) | 9.32E−04 | 5.53E−03 | 1.00 | 1.00 |
| Belatacept | 2.92E−04 | 1.30E−03 | 3.19 | 4.25 |
| A29K | 6.35E−04 | 1.77E−03 | 1.47 | 3.12 |
| T30D | 1.03E−03 | 5.79E−03 | 0.90 | 0.96 |
| E31I | 2.26E−03 | 4.27E−03 | 0.41 | 1.30 |
| R33F | NB | NB | 0.00 | 0.00 |
| T35E | NB | NB | 0.00 | 0.00 |
| A49T | 4.18E−03 | 1.60E−02 | 0.22 | 0.35 |
| T51V | 9.52E−04 | 6.40E−03 | 0.98 | 0.86 |
| M53E | 1.00E−03 | 6.20E−03 | 0.93 | 0.89 |
| T59V | 1.04E−03 | 5.77E−03 | 0.90 | 0.96 |
| L61D | 1.02E−03 | 2.48E−03 | 0.91 | 2.23 |
| D63E | 1.05E−03 | 6.51E−03 | 0.89 | 0.85 |
| S64K | 7.51E−04 | 6.94E−03 | 1.24 | 0.80 |
| K93D | NB | NB | 0.00 | 0.00 |
| E95D | NB | NB | 0.00 | 0.00 |
| M97F | 3.33E−03 | NB | 0.28 | 0.00 |
| Y98F | 1.11E−03 | NB | 0.84 | 0.00 |
| Y102F | 3.67E−03 | NB | 0.25 | 0.00 |
| Y103F | 1.47E−03 | 4.35E−03 | 0.63 | 1.27 |
| L104D | 3.16E−04 | 4.62E−03 | 2.95 | 1.20 |
| G105D | NB | NB | 0.00 | 0.00 |
| Experiment 2 | | | | |
| Abatacept (WT) | 1.01E−03 | 5.19E−03 | 1.00 | 1.00 |
| Belatacept | 3.46E−04 | 1.32E−03 | 3.19 | 4.25 |
| A29K | 8.87E−04 | 2.07E−03 | 1.14 | 2.51 |
| A29N | 1.71E−03 | 5.16E−03 | 0.59 | 1.01 |
| A29E | 9.53E−04 | 6.04E−03 | 1.06 | 0.86 |
| A29W | 8.37E−04 | 2.38E−03 | 1.21 | 2.18 |
| A29F | 1.16E−03 | 0.0107 | 0.87 | 0.49 |
| A29Y | 7.56E−04 | 3.11E−03 | 1.34 | 1.67 |
| A29H | 6.63E−04 | 1.92E−03 | 1.52 | 2.70 |
| T30V | 1.26E−03 | 5.80E−03 | 0.80 | 0.89 |

TABLE 1-continued

Off-rates ($k_{off}$) for binding of CTLA4-Ig variants to B7-1 and B7-2

| Variant | B7-1 ($k_{off}$) | B7-2 ($k_{off}$) | Fold B7-1 | Fold B7-2 |
|---|---|---|---|---|
| T30A | 1.60E−03 | 5.39E−03 | 0.63 | 0.96 |
| T30N | 1.10E−03 | 4.10E−03 | 0.92 | 1.27 |
| T30E | 1.01E−03 | 3.83E−03 | 1.00 | 1.36 |
| T30H | 1.18E−03 | 4.17E−03 | 0.86 | 1.24 |
| T30R | 1.34E−03 | 4.12E−03 | 0.75 | 1.26 |
| E31M | 7.65E−04 | NB | 1.32 | 0.00 |
| E31T | 9.65E−04 | NB | 1.05 | 0.00 |
| E31V | 1.49E−03 | NB | 0.68 | 0.00 |
| E31D | 5.61E−03 | 0.0243 | 0.18 | 0.21 |
| R33T | NB | NB | 0.00 | 0.00 |
| R33M | NB | NB | 0.00 | 0.00 |
| R33W | NB | NB | 0.00 | 0.00 |
| R33I | NB | NB | 0.00 | 0.00 |
| R33Y | NB | NB | 0.00 | 0.00 |
| R33L | NB | NB | 0.00 | 0.00 |
| R33E | NB | NB | 0.00 | 0.00 |
| R33Q | 9.34E−03 | NB | 0.11 | 0.00 |
| T35V | NB | NB | 0.00 | 0.00 |
| T35M | NB | NB | 0.00 | 0.00 |
| T35D | NB | NB | 0.00 | 0.00 |
| T35F | NB | NB | 0.00 | 0.00 |
| T35Y | NB | NB | 0.00 | 0.00 |
| A49F | 2.49E−03 | 0.031 | 0.41 | 0.17 |
| A49Y | 1.98E−03 | 0.0379 | 0.51 | 0.14 |
| A49W | 3.86E−03 | 6.38E−03 | 0.26 | 0.81 |
| A49D | 3.10E−03 | 0.0337 | 0.33 | 0.15 |
| A49E | 4.06E−03 | NB | 0.25 | NB |
| T51L | 1.47E−03 | NB | 0.69 | NB |
| T51N | 1.85E−03 | 2.42E−03 | 0.55 | 2.14 |
| T51H | 2.81E−03 | 0.0475 | 0.36 | 0.11 |
| M53Q | 1.49E−03 | 4.71E−03 | 0.68 | 1.10 |
| M53Y | 7.01E−04 | 4.66E−03 | 1.44 | 1.11 |
| T59L | 9.54E−04 | 5.14E−03 | 1.06 | 1.01 |
| T59N | 1.11E−03 | 5.18E−03 | 0.91 | 1.00 |
| T59Y | 1.05E−03 | 5.29E−03 | 0.96 | 0.98 |
| T59H | 1.15E−03 | 5.51E−03 | 0.88 | 0.94 |
| T59Q | 1.20E−03 | 5.18E−03 | 0.84 | 1.00 |
| T59I | 1.14E−03 | 5.50E−03 | 0.89 | 0.94 |
| L61E | 1.03E−03 | 3.48E−03 | 0.98 | 1.49 |
| L61I | 1.18E−03 | 6.30E−03 | 0.86 | 0.82 |
| L61A | 8.66E−04 | 3.79E−03 | 1.17 | 1.37 |
| L61F | 1.04E−03 | 5.86E−03 | 0.97 | 0.89 |
| Experiment 3 | | | | |
| Abatacept (WT) | 1.16E−03 | 5.45E−03 | 1.00 | 1.00 |
| Belatacept | 3.98E−04 | 1.41E−03 | 2.91 | 3.87 |
| L61G | 9.66E−04 | 2.11E−03 | 1.20 | 2.58 |
| L61H | 8.67E−04 | 4.39E−03 | 1.34 | 1.24 |
| L61K | 1.29E−03 | 2.63E−03 | 0.90 | 2.07 |
| L61M | 1.07E−03 | 5.01E−03 | 1.08 | 1.09 |
| L61N | 1.33E−03 | 2.68E−03 | 0.87 | 2.03 |
| L61P | 8.55E−04 | 2.79E−03 | 1.36 | 1.95 |
| L61Q | 1.87E−04 | 6.98E−03 | 6.20 | 0.78 |
| L61R | 1.06E−03 | 3.10E−03 | 1.09 | 1.76 |
| L61S | 9.81E−04 | 3.18E−03 | 1.18 | 1.71 |
| L61T | 1.29E−03 | 3.20E−03 | 0.90 | 1.70 |
| L61V | 1.33E−03 | 6.09E−03 | 0.87 | 0.89 |
| L61W | 9.37E−04 | 3.74E−03 | 1.24 | 1.46 |
| L61Y | 8.76E−04 | 4.79E−03 | 1.32 | 1.14 |
| S64R | 1.08E−03 | 7.22E−03 | 1.07 | 0.75 |
| S64Y | NB | NB | 0.00 | 0.00 |
| K93E | NB | NB | 0.00 | 0.00 |
| K93F | NB | NB | 0.00 | 0.00 |
| K93H | NB | NB | 0.00 | 0.00 |
| K93Q | 4.72E−04 | 3.68E−03 | 2.46 | 1.48 |
| K93R | 3.06E−04 | 6.06E−03 | 3.79 | 0.90 |
| K93T | NB | NB | 0.00 | 0.00 |
| K93V | 1.67E−04 | 4.77E−03 | 6.95 | 1.14 |
| K93W | NB | NB | 0.00 | 0.00 |
| K93Y | NB | NB | 0.00 | 0.00 |
| E95Q | NB | NB | 0.00 | 0.00 |
| E95Y | NB | NB | 0.00 | 0.00 |
| E95H | NB | NB | 0.00 | 0.00 |
| E95L | NB | NB | 0.00 | 0.00 |
| M97D | NB | NB | 0.00 | 0.00 |
| M97N | 5.32E−03 | NB | 0.22 | 0.00 |
| M97I | 5.60E−03 | NB | 0.21 | 0.00 |
| M97V | 0.0527 | NB | 0.02 | 0.00 |
| Y98W | 3.25E−03 | NB | 0.36 | 0.00 |
| Y102W | NB | NB | 0.00 | 0.00 |
| Y103W | 2.21E−03 | 0.0499 | 0.52 | 0.11 |
| Y103H | 2.51E−03 | 4.19E−03 | 0.46 | 1.30 |
| Y103D | 5.88E−04 | 2.46E−03 | 1.97 | 2.22 |
| Y103E | 7.30E−04 | 9.16E−04 | 1.59 | 5.95 |
| Y103N | 1.03E−03 | 7.40E−04 | 1.13 | 7.36 |
| Y103Q | 4.35E−04 | 7.52E−04 | 2.67 | 7.25 |
| L104E | 4.96E−04 | 3.08E−03 | 2.34 | 1.77 |
| L104V | 1.04E−03 | 3.75E−03 | 1.12 | 1.45 |
| L104M | 1.57E−03 | 4.16E−03 | 0.74 | 1.31 |
| L104Y | 8.54E−04 | 5.03E−03 | 1.36 | 1.08 |
| L104W | 8.42E−04 | 5.38E−03 | 1.38 | 1.01 |
| L104F | 1.13E−03 | 5.85E−03 | 1.03 | 0.93 |
| L104H | 5.94E−04 | 6.70E−03 | 1.95 | 0.81 |
| G105E | NB | NB | 0.00 | 0.00 |
| I106E | 7.81E−04 | 5.35E−03 | 1.49 | 1.02 |
| I106Y | 2.24E−03 | 4.29E−03 | 0.52 | 1.27 |

Off-rates ($k_{off}$) are presented in scientific E notation where E represents times ten raised to the power of;
Fold B7-1 = $k_{off}$(abatacept)/$k_{off}$(variant) for binding to B7-1;
Fold B7-2 = $k_{off}$(abatacept)/$k_{off}$(variant) for binding to B7-2;
NB = No binding was observed.

A plot of the Fold($k_{off}$) relative to abatacept is shown in FIG. 6. As can be seen from Table 1 and FIG. 6, a number of substitutions showed slower dissociation (higher binding) than the abatacept parent protein.

Variants with dissociation rates for B7-1 and/or B7-2 that were slower than abatacept were re-expressed at a larger scale and purified as described above. Protein concentrations were determined by absorbance at 280 nm. Binding affinities to B7-1 and B7-2 were measured with Biacore™ using a concentration series of CTLA4-Ig proteins. All variant CTLA4-Ig proteins were normalized to 1 uM and then QCd by protein A binding. An anti-His-chip was generated as above, and B7-1 and B7-2 were immobilized for 1 min. at 50 nM and 2 min. at 100 nM respectively. CTLA4-Ig proteins were diluted in a 2-fold series starting at 50, 25, 12.5 and 6.25 nM and injected for 1 min followed by 2 min dissociation. Kinetic data were fit to a 1:1 binding model (Langmuir) using the BIAevaluation software to provide dissociation rate constants ($k_d$ or $k_{off}$), association rate constants ($k_a$ or $k_{on}$), and equilibrium dissociation constants (KD or $K_D$). Binding affinities are provided in Table 2 (B7-1) and Table 3 (B7-2).

TABLE 2

B7-1 binding affinities and kinetic constants of CTLA4-Ig variants

| Variant | $k_{on}$ (1/Ms) | $k_{off}$ (1/s) | $K_D$ (M) | Fold $K_D$ |
|---|---|---|---|---|
| Abatacept | 2.38E+06 | 1.64E−03 | 6.91E−10 | 1.00 |
| Belatacept | 2.16E+06 | 7.75E−04 | 3.59E−10 | 1.92 |
| A29K | 9.18E+05 | 1.39E−03 | 1.52E−09 | 0.45 |
| A29W | 1.97E+06 | 1.42E−03 | 7.22E−10 | 0.96 |
| A29Y | 3.07E+06 | 1.26E−03 | 4.09E−10 | 1.69 |
| A29H | 2.34E+06 | 1.08E−03 | 4.62E−10 | 1.50 |
| T51N | 1.95E+06 | 3.16E−03 | 1.62E−09 | 0.43 |
| M53Y | 2.64E+06 | 1.18E−03 | 4.45E−10 | 1.55 |
| L61D | 3.26E+06 | 2.04E−03 | 6.26E−10 | 1.10 |
| L61E | 2.63E+06 | 1.65E−03 | 6.25E−10 | 1.11 |
| L61G | 2.76E+06 | 1.52E−03 | 5.49E−10 | 1.26 |
| L61K | 2.24E+06 | 1.85E−03 | 8.27E−10 | 0.84 |
| L61N | 2.60E+06 | 2.03E−03 | 7.82E−10 | 0.88 |
| K93Q | 2.57E+06 | 8.75E−04 | 3.40E−10 | 2.03 |
| K93R | 1.16E+06 | 1.47E−03 | 1.26E−09 | 0.55 |
| K93V | 1.15E+06 | 7.54E−04 | 6.55E−10 | 1.05 |

TABLE 2-continued

B7-1 binding affinities and kinetic constants of CTLA4-Ig variants

| Variant | $k_{on}$ (1/Ms) | $k_{off}$ (1/s) | $K_D$ (M) | Fold $K_D$ |
|---|---|---|---|---|
| Y103D | 2.01E+06 | 0.0105 | 5.24E−09 | 0.13 |
| Y103E | 2.45E+06 | 0.0143 | 5.85E−09 | 0.12 |
| Y103N | 2.14E+06 | 0.0188 | 8.77E−09 | 0.08 |
| Y103Q | 1.83E+06 | 8.17E−03 | 4.48E−09 | 0.15 |
| L104D | 5.57E+05 | 2.11E−03 | 3.79E−09 | 0.18 |
| L104E | 2.47E+06 | 8.90E−04 | 3.60E−10 | 1.92 |
| L104V | 2.54E+06 | 1.54E−03 | 6.05E−10 | 1.14 |

$k_{on}$ = on-rate;
$k_{off}$ = off-rate;
$K_D$ = equilibrium dissociation constant;
Fold $K_D$ = $K_D$(abatacept)/$K_D$(variant)

TABLE 3

B7-2 binding affinities and kinetic constants of CTLA4-Ig variants

| Variant | $k_{on}$ (1/Ms) | $k_{off}$ (1/s) | $K_D$ (M) | Fold $K_D$ |
|---|---|---|---|---|
| Abatacept | 3.64E+06 | 1.66E−02 | 4.55E−09 | 1.00 |
| Belatacept | 3.35E+06 | 2.18E−03 | 6.52E−10 | 6.98 |
| A29K | 1.55E+06 | 3.96E−03 | 2.55E−09 | 1.78 |
| A29W | 3.28E+06 | 4.74E−03 | 1.44E−09 | 3.16 |
| A29Y | 4.45E+06 | 6.29E−03 | 1.41E−09 | 3.23 |
| A29H | 3.35E+06 | 3.42E−03 | 1.02E−09 | 4.46 |
| T51N | 2.86E+06 | 5.07E−03 | 1.77E−09 | 2.57 |
| M53Y | 3.90E+06 | 1.17E−02 | 3.01E−09 | 1.51 |
| L61D | 4.51E+06 | 1.55E−02 | 3.44E−09 | 1.32 |
| L61E | 4.18E+06 | 1.30E−02 | 3.11E−09 | 1.46 |
| L61G | 3.54E+06 | 2.05E−02 | 5.79E−09 | 0.79 |
| L61K | 2.63E+06 | 2.76E−02 | 1.05E−08 | 0.43 |
| L61N | 3.45E+06 | 2.01E−02 | 5.81E−09 | 0.78 |
| K93Q | 3.80E+06 | 8.43E−03 | 2.22E−09 | 2.05 |
| K93R | 1.79E+06 | 1.71E−02 | 9.55E−09 | 0.48 |
| K93V | 1.68E+06 | 1.22E−02 | 7.30E−09 | 0.62 |
| Y103D | 1.11E+06 | 9.28E−03 | 8.38E−09 | 0.54 |
| Y103E | 1.26E+06 | 8.38E−03 | 6.64E−09 | 0.69 |
| Y103N | 1.54E+06 | 0.0143 | 9.27E−09 | 0.49 |
| Y103Q | 1.53E+06 | 7.46E−03 | 4.89E−09 | 0.93 |
| L104D | 8.37E+05 | 1.75E−02 | 2.09E−08 | 0.22 |
| L104E | 3.93E+06 | 6.25E−03 | 1.59E−09 | 2.86 |
| L104V | 3.47E+06 | 1.47E−02 | 4.22E−09 | 1.08 |

$k_{on}$ = on-rate;
$k_{off}$ = off-rate;
$K_D$ = equilibrium dissociation constant;
Fold $K_D$ = $K_D$(abatacept)/$K_D$(variant)

Based on the results of the single substitution screen, a library of combination variants and additional single substitution variants was designed. The new variants are listed in Tables 4 and 5. Variants were constructed, expressed, and purified as described above. Binding to B7 targets was measured as described above, and fitted kinetic rate constants and affinities are provided in Table 4 (B7-1) and Table 5 (B7-2).

TABLE 4

B7-1 binding affinities and kinetic constants of CTLA4-Ig variants

| Variant | $k_{on}$ (1/Ms) | $k_{off}$ (1/s) | $K_D$ (M) | Fold $K_D$ abatacept |
|---|---|---|---|---|
| Abatacept | 2.26E+07 | 1.32E−03 | 5.85E−11 | 1.00 |
| Belatacept (A29Y/L104E) | 2.21E+07 | 5.57E−04 | 2.52E−11 | 2.32 |
| A29H/T51N/M53Y/L61E/K93Q | 2.71E+07 | 6.11E−04 | 2.25E−11 | 2.60 |
| A29H/T51N/M53Y/K93Q | 1.72E+07 | 6.87E−04 | 4.01E−11 | 1.46 |
| A29H/T51N/M53Y/L61E | 3.20E+07 | 1.10E−03 | 3.43E−11 | 1.71 |
| A29H/T51N/L61E/K93Q | 3.16E+07 | 5.18E−04 | 1.64E−11 | 3.57 |
| A29H/M53Y/L61E/K93Q | 3.35E+07 | 6.09E−04 | 1.82E−11 | 3.21 |
| T51N/M53Y/L61E/K93Q | 2.72E+07 | 6.90E−04 | 2.53E−11 | 2.31 |
| A29H/M53Y/K93Q | 1.95E+07 | 6.45E−04 | 3.31E−11 | 1.77 |
| A29H/L61E/K93Q | 2.48E+07 | 6.45E−04 | 2.60E−11 | 2.25 |
| A29H/T51N/L61E | 3.53E+07 | 1.03E−03 | 2.92E−11 | 2.00 |
| A29H/M53Y/L61E | 3.30E+07 | 7.92E−04 | 2.40E−11 | 2.44 |
| T51N/M53Y/L61E | 1.86E+07 | 1.99E−03 | 1.07E−10 | 0.55 |
| M53Y/L61E/K93Q | 2.13E+07 | 6.85E−04 | 3.22E−11 | 1.82 |
| T51N/L61E/K93Q | 2.14E+07 | 7.63E−04 | 3.57E−11 | 1.64 |
| A29H/T51N | 2.12E+07 | 1.64E−03 | 7.75E−11 | 0.75 |
| A29H/M53Y | 1.97E+07 | 7.62E−04 | 3.87E−11 | 1.51 |
| A29H/K93Q | 2.26E+07 | 6.35E−04 | 2.81E−11 | 2.08 |
| T51N/M53Y | 1.53E+07 | 3.56E−03 | 2.32E−10 | 0.25 |
| T51N/K93Q | 1.76E+07 | 7.94E−04 | 4.50E−11 | 1.30 |
| T51Q | 1.11E+07 | 0.0137 | 1.22E−09 | 0.05 |
| T51E | 1.31E+07 | 0.0474 | 3.62E−09 | 0.02 |
| T51S | 1.20E+07 | 1.29E−03 | 1.07E−10 | 0.55 |
| T51R | 7.08E+06 | 0.0181 | 2.56E−09 | 0.02 |
| T51D | 9.86E+06 | 0.0359 | 3.64E−09 | 0.02 |
| M53W | 1.28E+07 | 2.21E−03 | 1.72E−10 | 0.34 |
| M53F | 1.12E+07 | 1.08E−03 | 9.57E−11 | 0.61 |
| M53H | 1.51E+07 | 1.48E−03 | 9.80E−11 | 0.60 |
| K93N | NB | | | |
| K93S | 1.16E+04 | 3.42E−04 | 2.96E−08 | 0.00 |
| A29Q | 4.33E+06 | 2.12E−03 | 4.91E−10 | 0.12 |
| A29R | 1.04E+06 | 2.22E−03 | 2.13E−09 | 0.03 |

$k_{on}$ = on-rate;
$k_{off}$ = off-rate;
$K_D$ = equilibrium dissociation constant;
Fold $K_D$ = $K_D$(abatacept)/$K_D$(variant);
NB = no binding detected.

TABLE 5

B7-2 binding affinities and kinetic constants of CTLA4-Ig variants

| Variant | $k_{on}$ (1/Ms) | $k_{off}$ (1/s) | $K_D$ (M) | Fold $K_D$ abatacept |
|---|---|---|---|---|
| Abatacept | 3.10E+07 | 0.0135 | 4.37E−10 | 1.00 |
| Belatacept (A29Y/L104E) | 3.21E+07 | 2.18E−03 | 6.79E−11 | 6.44 |
| A29H/T51N/M53Y/L61E/K93Q | 3.59E+07 | 1.20E−03 | 3.35E−11 | 13.04 |
| A29H/T51N/M53Y/K93Q | 3.55E+07 | 1.31E−03 | 3.70E−11 | 11.81 |
| A29H/T51N/M53Y/L61E | 5.11E+07 | 2.50E−03 | 4.89E−11 | 8.94 |
| A29H/T51N/L61E/K93Q | 4.68E+07 | 1.07E−03 | 2.28E−11 | 19.17 |
| A29H/M53Y/L61E/K93Q | 4.86E+07 | 1.43E−03 | 2.94E−11 | 14.86 |
| T51N/M53Y/L61E/K93Q | 4.75E+07 | 2.39E−03 | 5.05E−11 | 8.65 |
| A29H/M53Y/K93Q | 3.86E+07 | 1.34E−03 | 3.48E−11 | 12.56 |
| A29H/L61E/K93Q | 4.86E+07 | 1.53E−03 | 3.14E−11 | 13.92 |
| A29H/T51N/L61E | 3.77E+07 | 2.32E−03 | 6.14E−11 | 7.12 |
| A29H/M53Y/L61E | 3.40E+07 | 2.47E−03 | 7.27E−11 | 6.01 |
| T51N/M53Y/L61E | 4.31E+07 | 4.64E−03 | 1.08E−10 | 4.05 |
| M53Y/L61E/K93Q | 5.38E+07 | 5.11E−03 | 9.50E−11 | 4.60 |
| T51N/L61E/K93Q | 5.68E+07 | 2.29E−03 | 4.04E−11 | 10.82 |
| A29H/T51N | 3.33E+07 | 2.56E−03 | 7.69E−11 | 5.68 |
| A29H/M53Y | 3.27E+07 | 2.41E−03 | 7.36E−11 | 5.94 |
| A29H/K93Q | 3.06E+07 | 1.73E−03 | 5.65E−11 | 7.73 |
| T51N/M53Y | 3.37E+07 | 5.54E−03 | 1.64E−10 | 2.66 |
| T51N/K93Q | 3.50E+07 | 2.20E−03 | 6.29E−11 | 6.95 |
| T51Q | 1.29E+07 | 0.15 | 1.16E−08 | 0.04 |
| T51E | NB | NB | | 0.00 |

TABLE 5-continued

B7-2 binding affinities and kinetic constants of CTLA4-Ig variants

| Variant | $k_{on}$ (1/Ms) | $k_{off}$ (1/s) | $K_D$ (M) | Fold $K_D$ abatacept |
|---|---|---|---|---|
| T51S | 1.41E+07 | 4.59E-03 | 3.26E-10 | 1.34 |
| T51R | 1.07E+07 | 0.0343 | 3.21E-09 | 0.14 |
| T51D | NB | NB | | 0.00 |
| M53W | 1.89E+07 | 7.46E-03 | 3.95E-10 | 1.11 |
| M53F | 2.41E+07 | 9.40E-03 | 3.90E-10 | 1.12 |
| M53H | 1.31E+07 | 0.0132 | 1.01E-09 | 0.43 |
| K93N | NB | NB | | 0.00 |
| K93S | NB | NB | | 0.00 |
| A29Q | 7.92E+06 | 0.0164 | 2.07E-09 | 0.21 |
| A29R | 1.57E+06 | 0.0112 | 7.15E-09 | 0.06 |

$k_{on}$ = on-rate;
$k_{off}$ = off-rate;
$K_D$ = equilbrium dissociation constant;
Fold $K_D$ = $K_D$(abatacept)/$K_D$(variant);
NB = no binding detected.

Figure 7:
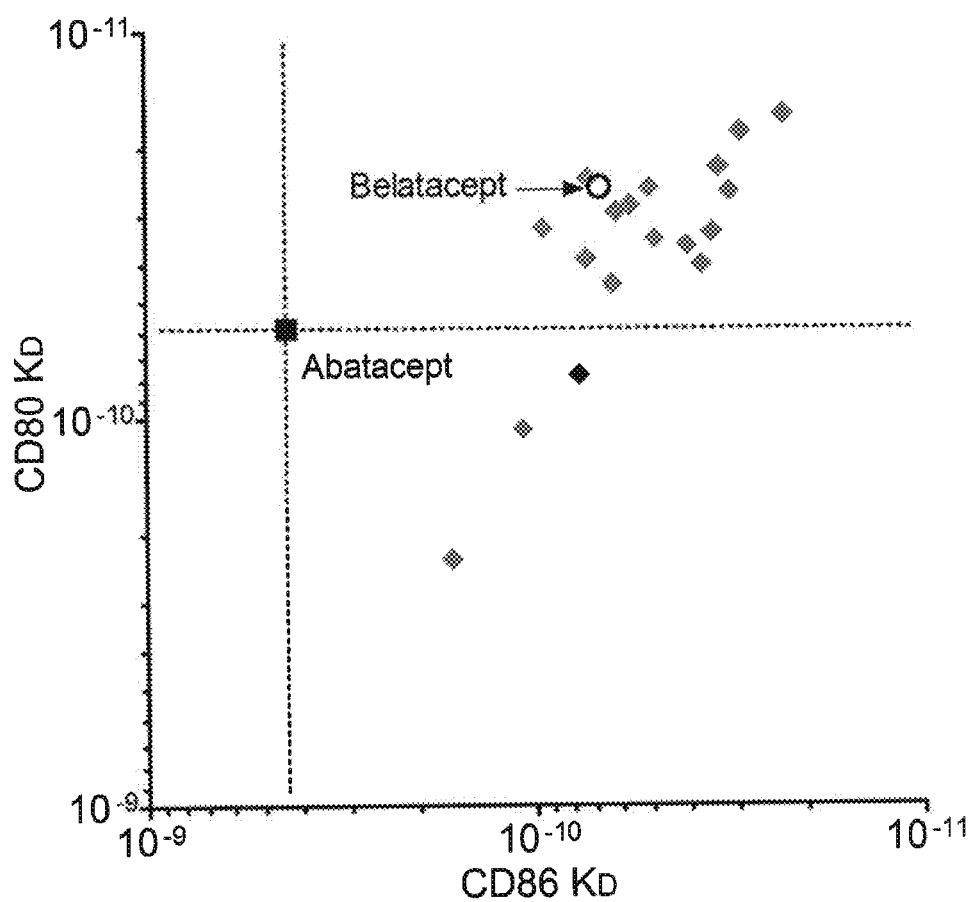
FIG. 7. Plot of the CD80 and CD86 $K_D$ for CTLA4-Ig variants compared to abatacept and belatacept. CTLA4-Ig variants of the present study are represented as gray triangles. The black square represents the parent CTLA4-Ig abatacept, and the black open circle represents belatacept.

A plot of the CD80 and CD86 KD for all of the variants compared to abatacept and belatacept is shown in FIG. 7. A number of the combination variants bound more tightly to both B7-1 (CD80) and B7-2 (CD86) relative to the abatacept parent CTLA4-Ig, providing up to 3.6-fold binding improvement to B7-1 and up to 19.2-fold binding improvement to B7-2. The best triple substitution variant for B7-2 binding was T51N/L61E/K93Q (referred to as NEQ), which improved B7-2 affinity from 437 pM to 40 pM, and which improved B7-1 affinity from 59 pM to 36 pM. The best quadruple substitution variant for B7-2 binding was A29H/T51N/L61E/K93Q (referred to as HNEQ), which improved B7-2 affinity from 437 pM to 23 pM, and which improved B7-1 affinity from 59 pM to 16 pM. A plot of the sensorgrams from the highest CTLA4-Ig concentration for the HNEQ variant compared to abatacept and belatacept is shown in FIG. 8. Amino acid sequences of these CTLA4 variant and CTLA4-Ig variant proteins are provided in FIG. 9.

Example 2

Engineered CTLA4-Ig Variants have Greater T-Cell Inhibitory Activity In Vitro The NEQ and HNEQ variant CTLA4-Ig proteins were tested in a cell-based assay for their capacity to inhibit T-cell proliferation. Abatacept, belatacept, and an anti-RSV IgG1 antibody with no specificity for B7-1 or B7-2 (negative control) were run as controls. In this assay, T cell activation and proliferation were stimulated using the anti-CD3 antibody OKT3 and recombinant B7-2 Fc fusion (R & D Systems). U shape tissues culture plates were coated with 2 ug/ml CD86-Fc and 0.5 ug/ml anti-OKT3 in PBS at 4° C. overnight. Plates were washed 3× with PBS. Human peripheral blood mononuclear cells (PBMCs) were purified from leukapheresis of anonymous healthy volunteers (HemaCare, VanNuys, Calif.) using Ficoll-Paque™ Plus density gradients (Amersham Biosciences, Newark, N.J.). T cells were isolated from PBMC using an EasySep® Human T Cell Enrichment Kit (StemCell Technologies) and labeled T cells with CSFE (10 uM). CTLA4-Ig protein variants and controls were added at 4-fold dilutions over 8 concentrations with the highest concentration at 50 ug/ml. Samples were run in duplicate. ~500,000 T cells were added to the coated plate and incubated for 4 days at 37° C. Control conditions were carried out with cells on CD86-Fc/OKT3 coated wells and cells only (without coating). After 4 days culture, samples were analyzed for FITC staining (CSFE) using a FACSCanto2™. The data in FIG. 10 show that the tested CTLA4-Ig variants T51N/L61E/K93Q and A29H/T51N/L61E/K93Q are superior to the parent CTLA4-Ig abatacept, consistent with their improved B7-1 and B7-2 affinities. Moreover, both T51N/L61E/K93Q and A29H/T51N/L61E/K93Q variant showed greater inhibitory activity relative to belatacept, consistent with their greater B7-2 affinity.

Example 3

CTLA4-Ig Immunoadhesins with Enhanced Binding to FcRn for Extended In Vivo Half-Life The Fc region of the CTLA4-Ig proteins were engineered to enhance affinity for the neonatal Fc receptor FcRn, with the goal of improving in vivo serum half-life. Fc variants that improve FcRn binding and may provide enhanced pharmacokinetic properties include but are not limited to substitutions at positions 259, 307, 308, 311, 378, 426, 428, 434, and 436 including but not limited to for example 259I, 307Q, 308F, 311I, 311V, 378V, 378T, 426V, 428L, 434S, 434H, 434F, 434Y, 434M, 436I, and 436V (U.S. Ser. No. 12/341,769, filed Dec. 22, 2008, herein expressly incorporated by reference). Other variants that increase Fc binding to FcRn include but are not limited to: 250E, 250Q, 428L, 428F, 250Q/428L (Hinton et al., 2004, J. Biol. Chem. 279(8): 6213-6216, Hinton et al. 2006 Journal of Immunology 176:346-356), 256A, 272A, 286A, 305A, 307A, 311A, 312A, 376A, 378Q, 380A, 382A, 434A (Shields et al, Journal of Biological Chemistry, 2001, 276(9):6591-6604, entirely incorporated by reference), 252F, 252T, 252Y, 252W, 254T, 256S, 256R, 256Q, 256E, 256D, 256T, 309P, 311S, 433R, 433S, 433I, 433P, 433Q, 434H, 434F, 434Y, 252Y/254T/256E, 433K/434F/436H, and 308T/309P/311S (Dall Acqua et al. Journal of Immunology, 2002, 169:5171-5180, Dall'Acqua et al., 2006, The Journal of Biological Chemistry 281:23514-23524, entirely incorporated by reference).

Substitutions M428L and N434S that provide enhanced FcRn affinity and extended half-life were engineered into the Fc region of abatacept CTLA4-Ig(ab), CTLA4-Ig(G2), belatacept, and Ig(G2-ELLG) versions of the CTLA4 (HNEQ) and CTLA4(NEQ) variants. Amino acid sequences of these CTLA4-Ig variant proteins are provided in FIG. 11.

CTLA4-Ig variant proteins were constructed, expressed, and purified as described above. Affinity of these variants to FcRn at pH 6.0 was measured using Biacore™ with an antigen-mediated immunoadhesin capture/human FcRn analyte format using a Biacore™ 3000 instrument (Biacore™). B7-1 and B7-2 were immobilized on CM5 chip to a density of 6500 and 8400 RUs respectively using standard amine coupling method. Ligands were diluted in pH 4.0 acetate buffer to 200 nM each. Surface was activated for 4 min with full-strength 1-Ethyl-3-[3-dimethylaminopropyl]carbodiimide hydrochloride (EDC)+N-hydroxysulfosuccinimide (Sulfo-NHS) followed by injection of B7-1 or B7-2 Fc fusion ligand (R&D Systems) for 15 min at 2 ul/min. Finally the surface was blocked with ethanolamine. Capture of CTLA4-Ig proteins was carried out in pH 6.0 phosphate buffer at either 20 nM (WT IgG1 Fc) or 10 nM (M428L/N434S variant Fc) for 2 minutes to achieve RUs of 1500 or 700 respectively. Then human FcRn analyte solutions at concentrations 500, 250, and 125 nM were injected at indicated concs followed by regeneration of B7 surface with pH 4.0 acetate+500 mM NaCl buffer before the next cycle. Due to Fc-fusion present on B7, there was a high background of hFcRn binding directly to the surface, therefore a concentration series of hFcRn was injected on non immobilized (empty) surface to manually subtract this background during Biaevaluation analysis. Following background/drift subtraction and axis-zeroing, sensograms were fit globally to a 1:1 Langmuir binding model using the BIAevaluation software (Biacore™)

Figure 12:
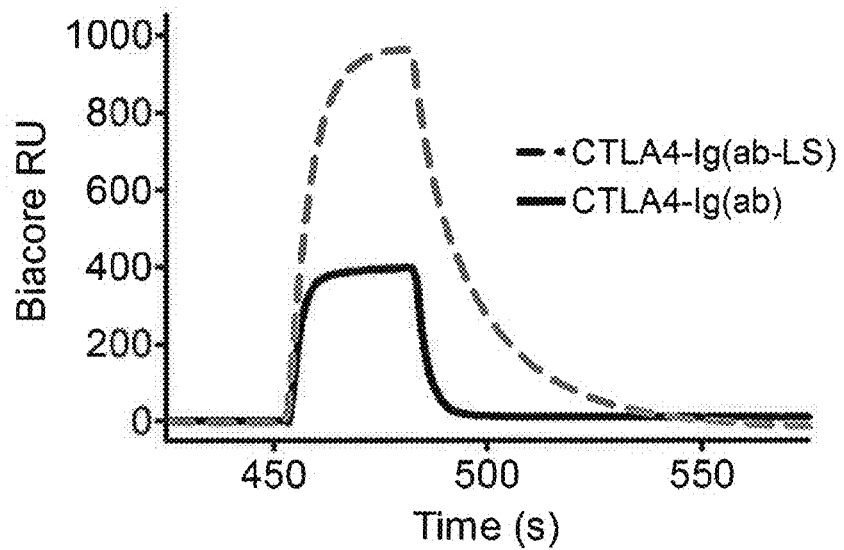
FIG. 12. Biacore sensorgrams for binding to human FcRn at pH 6.0 by native and Fc variant versions of CTLA4-Ig proteins. LS refers to the 428L/434S variant.
Figure 13:
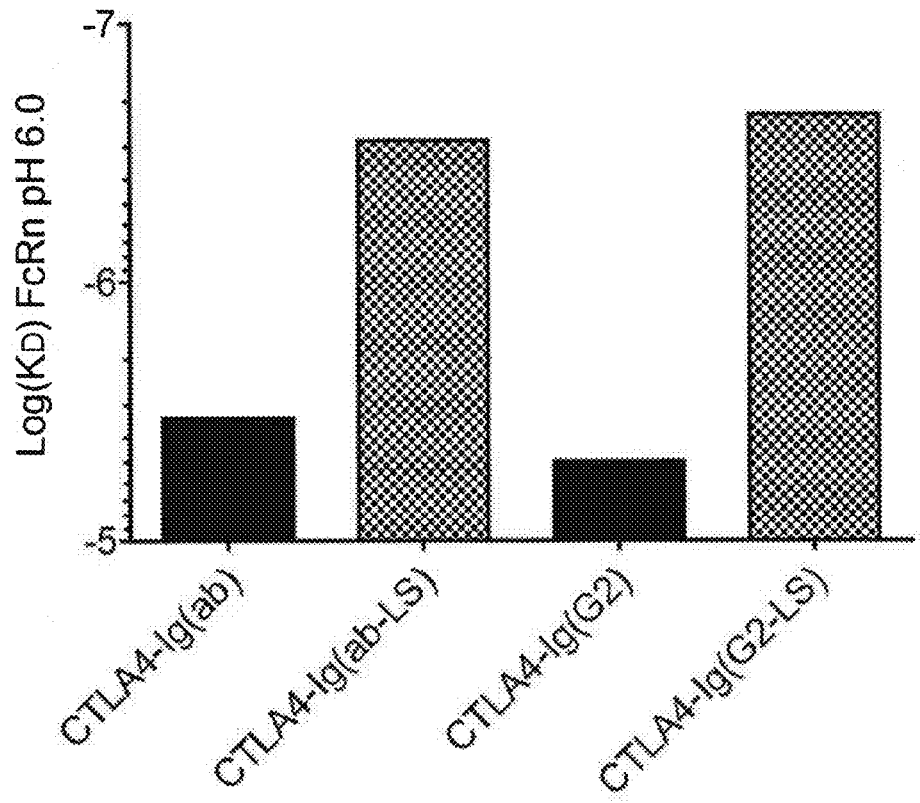
FIG. 13. Plot of FcRn binding affinities (pH 6.0) of native Fc and variant Fc versions of CTLA4-Ig proteins as determined by Biacore. LS refers to the 428L/434S variant.

Representative sensorgrams for binding of abatacept CTLA4-Ig(ab) and the Fc engineered version CTLA4-Ig(ab-LS) (LS=428L/434S) are shown in FIG. 12. Fitted affinities for binding to FcRn by abatacept CTLA4-Ig(ab) and CTLA4-Ig(G2) along with Fc engineered versions CTLA4-Ig(ab-LS) and CTLA4-Ig(G2-LS) are provided in Table 6 and plotted in FIG. 13. The results demonstrate the enhanced affinity for FcRn of the Fc engineered versions of the CTLA4-Ig proteins, and thus the potential of the Fc variant versions for longer half-life in vivo.

TABLE 6

Binding affinities of CTLA4-Ig proteins to human FcRn at pH 6.0

| Immunoadhesin | $K_D$ (uM) | Fold |
|---|---|---|
| Abatacept CTLA4-Ig(ab) | 3.4 | 1.0 |
| CTLA4-Ig(ab-428L/434S) | 0.28 | 12 |
| CTLA4-Ig(G2) | 5.0 | 1.0 |
| CTLA4-Ig(G2-428L/434S) | 0.23 | 22 |

Example 4

Figure 14:
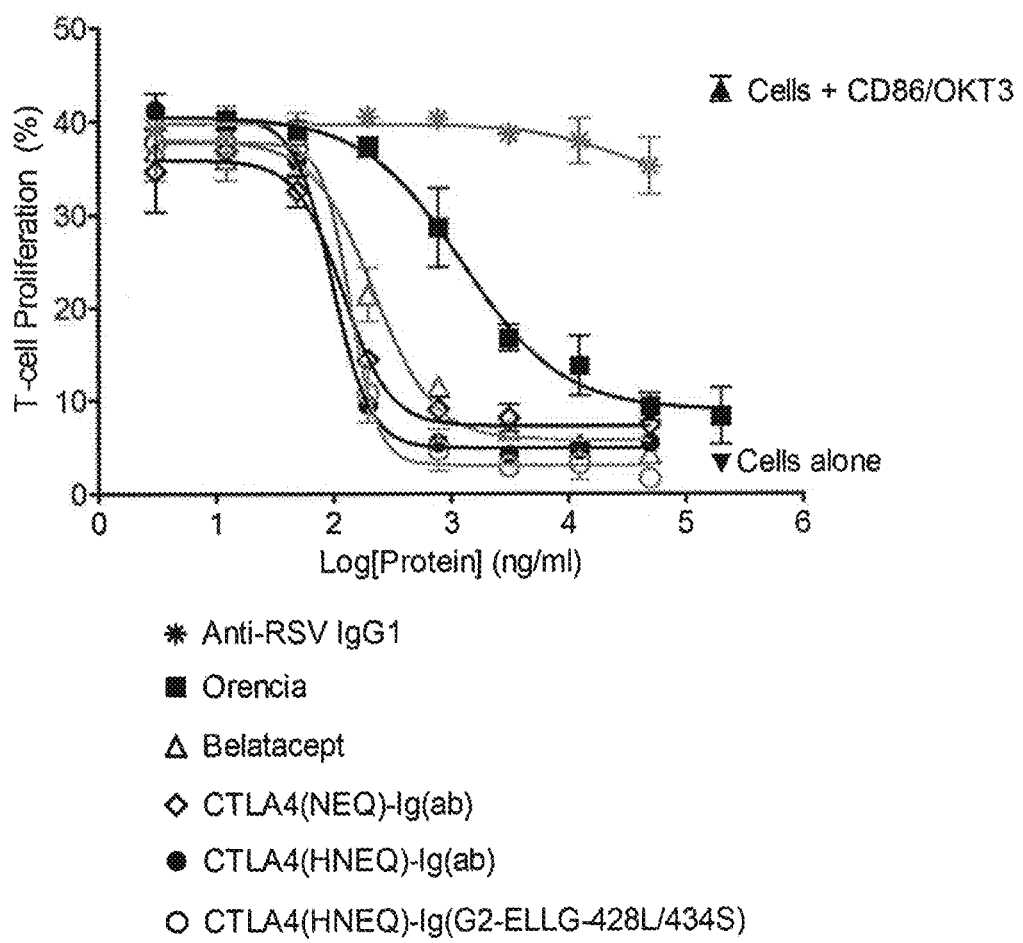
FIG. 14. T-cell inhibitory activity of CTLA4-Ig variants. T cells were activated by co-ligation of CD3 using an anti-CD3 antibody and B7-2 using recombinant B7-2-Ig. CFSE-labeled T cells were monitored using flow cytometry.

CTLA4-Ig Immunoadhesins with Enhanced T Cell Inhibitory Activity in Mixed Lymphocyte Reactions Select CTLA4-Ig variants with enhanced binding to FcRn were tested for their T-cell inhibitory activity. CTLA4-Ig proteins were tested in the cell-based assay described above where T-cell proliferation was stimulated using the anti-CD3 antibody and B7-2 Fc fusion. The data in FIG. 14 show the potent and superior inhibitory activity of the B7 affinity-enhanced CTLA4 variants (T51N/L61E/K93Q and A29H/T51N/L61E/K93Q) coupled with the FcRn affinity-enhancing Fc variants (M428L/N434S).

The T-cell inhibitory activities of the CTLA4-Ig variants were further measured by testing them in a mixed-lymphocyte reaction (also known as a mixed-leukocyte reaction or MLR). The MLR is an in vitro method for assaying T helper (TH) cell proliferation and for generating a population of cytotoxic T lymphocytes (CTLs). When allogeneic (different MHC haplotype) lymphocytes are cultured together, TH cell populations expand, followed by expansion of a CTL population. MHC/TCR and B7/CD28 co-stimulatory pathways are critical to allogeneic reaction. Interleukin-2 (IL-2) secretion was used to monitor T cell activation. In two separate experiments, two different sets of human PBMCs were purified from leukapheresis of two different anonymous healthy volunteers (HemaCare, VanNuys, Calif.) using Ficoll-Paque™ Plus density gradients (Amersham Biosciences, Newark, N.J.). PBMCs were mixed at ~1.2×10E6 per well each with 300 ul RPMI1640/10% FBS. In one of the two experiments, PBMCs from donors 2336 and 3070 were mixed, in the other experiment PBMCs from donors 3070 and 3995 were mixed. CTLA4-Ig proteins and anti-RSV IgG1 negative controls were prepared in a 10 point 4× dilution series and added at the indicated final concentrations to the mixed PBMCs. PBMCs alone (separately) were also run as controls. Plates were incubated for 6 days. Supernatant was collected and concentration of IL-2 was measured using an IL-2 ELISA LegendMax™ Kit (BioLegend). The results of the assays are provided in FIG. 15.

The data in FIG. 15 support the potent inhibitory activity of the CTLA4-Ig variants, as well as their superiority to Orencia® (abatacept). Surprisingly, the NEQ variant outperformed the HNEQ variant, despite the greater affinity of the HNEQ variant for both B7-1 and B7-2 (Tables 4 and 5). The HNEQ variant improves B7-1 affinity 3.6-fold and B7-2 affinity 19.2-fold relative to abatacept, while the NEQ variant improves B7-1 affinity 1.6-fold and B7-2 affinity 10.8-fold relative to abatacept. The greater T-cell inhibitory activity of the NEQ variant may reflect the different biological roles of B7-1 and B7-2 in immune response. Recent work has demonstrated that B7-2 is the dominant ligand of CD28, while B7-1 is the dominant ligand of CTLA4, and further that B7-2 is unable recruit CTLA-4 to the immune synapse (Collins et al., 2002, Immunity 17:201-210; Jansson et al., 2005, J Immunol 175:1575-1585). Because of the role of endogenous CTLA4 in downregulating T cells (Alegre et al., 2001, Nat Rev Immunol 1:220-8), as well as its role in regulatory T cell (Treg)-mediated suppression of immune response (Sakaguchi et al., 2009, International Immunology 21 [10]:1105-1111), increased affinity for B7-1, which preferentially engages endogenous CTLA4, may inhibit the natural inhibitor, thus promoting T-cell activation. In this light, for therapeutic purposes B7-2 may be the more important ligand to inhibit, and accordingly the optimal variant for CTLA4 optimization may be selective enhancement in affinity to B7-2 relative to B7-1. Substitutions that selectively improve affinity to B7-2 relative to B7-1 include for example A29H, A29K, T51N, L61E, and Y103Q. It is noted that for experimental purposes, testing this selectivity hypothesis may benefit from variants that provide the opposite selectivity, i.e. improved binding to B7-1 relative to B7-2, including for example K93V, L61Q, and L104H. Overall the results indicate that the NEQ combination variant T51N/L61E/K93Q is the optimal variant with regard to selectivity, providing 10.8-fold affinity enhancement to B7-2 but only marginally (1.6-fold) greater binding to B7-1. This affinity and selectivity profile is superior to belatacept, which improves affinity only 6.5-7-fold to B7-2 and 2.3-fold to B7-1 (Tables 2-5).

Example 5

In Vivo Activity of Novel CTLA4-Ig Immunoadhesins

An in vivo experiment in mice was carried out to test the activity of the engineered CTLA4-Ig variants. The capacity of the CTLA4-Ig proteins to inhibit a human immune response to tetanus was carried out in severe combined immunodeficiency (SCID) mice engrafted with human peripheral blood leukocytes (PBLs). SCID mice were chosen as the animal model for this study as these mice are immunocompromised and will accept engraftment of human PBMC. CTLA4-Ig proteins for in vivo studies were expressed in CHO cells (Biotechnology Research Institute, National Research Council Canada) and purified as described above.

Human peripheral blood mononuclear cells (PBMCs) were obtained from a leukopack collected from a random donor (Hemacare, Van Nuys, Calif.). PBMCs were purified by Ficoll density gradient centrifugation (Ficoll-Paque™ Plus, GE Healthcare), resuspended in RPMI 1640 (Mediatech) and injected intraperitoneally (i.p.) at a dose of $3\times10^7$ cells. One day prior to PBMC injection, mice were injected i.p. with 100 ul of anti-asialo GM (Wako, Richmond, Va.) to deplete murine NK cells. The next day, mice were injected i.p.

with 3×107 PBMC in a 0.5 ml volume. A total of approximately 70 mice were injected. The day of cell injection was defined as study day 0. All animals were injected with PBMC on the same day.

After PBMC injection, mice were randomly assigned to groups and weighed. On day 7 post PBMC injection, blood was collected from all mice via retro-orbital sinus/plexus (OSP) puncture for determination of human IgG levels (hIgG ELISA, ZeptoMetrix, Buffalo, N.Y.) On the same day after the blood collection (day 7), mice were injected i.p. 1 mg/kg test article or PBS as a negative control. Mice continued to receive injections every 3 or 4 days throughout the study. Test articles were injected on a mg/kg basis using the most recent body weight measurement. On day 9, mice were injected i.p. with 15 μg tetanus toxoid (List Biological Labs, Campbell, Calif., catalog #191B) or with PBS. On day 21 (12 days post antigen vaccination), blood was collected from all mice for determination of human IgG and anti-tetanus IgG.

Blood samples (25-50 ul) were collected at days 7 and 21 post-PBMC engraftment using Retro-orbital sinus/plexus (OSP) (using topical proparacaine anesthetic and inhalant isoflurane). Blood samples were transferred to serum separator tubes, allowed to sit for 30 mins-1 hour to allow the blood to clot and then spun in a centrifuge (3500 rpm for 30 mins). The resulting serum was transferred to polypropylene tubes labeled with study number, animal number, date, collection timepoint. Serum samples were stored at −20 C. Serum concentration of anti-tetanus antibody (anti-TT IgG) was measured using a standard anti-tetanus ELISA kit (IBL-America).

Figure 16:
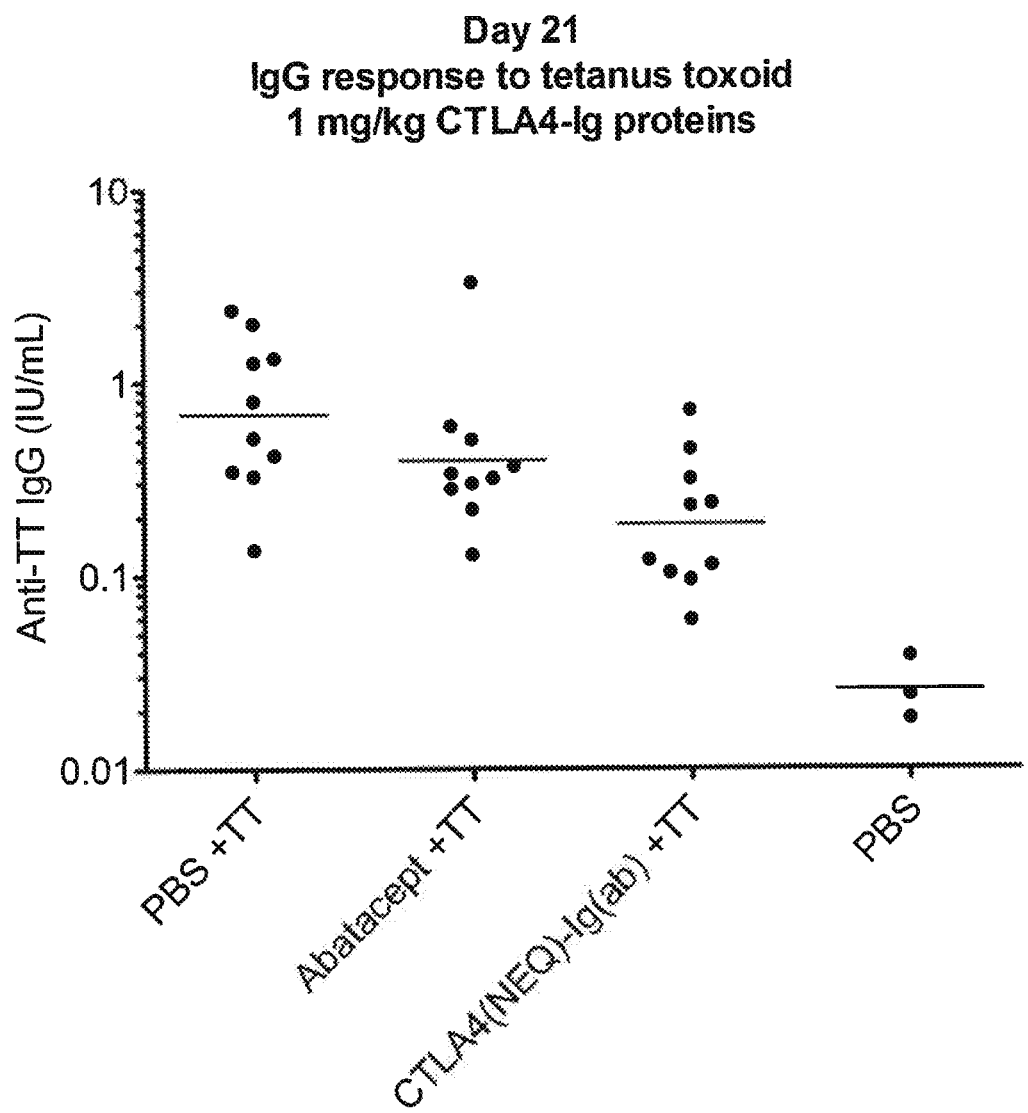
FIG. 16. Inhibitory activity of variant CTLA4-Ig proteins in vivo. The capacity of the CTLA4-Ig proteins to inhibit a human immune response to tetanus was-carried out in severe combined immunodeficiency (SCID) mice engrafted with human peripheral blood leukocytes (PBLs). The graph shows the serum level of anti-tetanus antibodies (Anti-TT IgG) after tetanus challenge at day 21 post-PBL engraftment when treated with PBS (PBS+TT), abatacept, and variant CTLA4 (NEQ)-Ig(ab) (51N/61E/93Q with enhanced affinity for B7-1 and B7-2). PBS alone (no tetanus) was run as a negative control.

The results in FIG. 16 demonstrate the activity of the affinity-enhanced NEQ variant CTLA4-Ig immunoadhesin relative to PBS+tetanus alone. Furthermore, the data show that the NEQ variant had more potent inhibitory activity than the parent CTLA4-Ig abatcept. These data support the use of the CTLA4-Ig variants described herein for treating immune related disorders.

All cited references are herein expressly incorporated by reference in their entirety. Whereas particular embodiments of the invention have been described above for purposes of illustration, it will be appreciated by those skilled in the art that numerous variations of the details may be made without departing from the invention as described in the appended claims.

We claim:

1. A method of inhibiting T cell activation in the presence of B7-expressing antigen presenting cells (APCs) comprising contacting said T cells with an immunoadhesin, said immunoadhesin comprising a first domain comprising a variant CTLA4 as compared to SEQ ID NO:6 and a second domain comprising an IgG Fc region, wherein said variant CTLA4 comprises an amino acid modification selected from the group consisting of T51N, A29H, M53Y, L61E, and K93Q, wherein the binding of said variant CTLA4 to B7-1 (CD80) and/or B7-2 (CD86) is increased as compared to SEQ ID NO:6.

2. The method of claim 1, wherein said B7-expressing antigen presenting cells express B7-2.

3. The method of claim 1, wherein the modification is T51N.

4. The method of claim 1, wherein the modification is A29H.

5. The method of claim 1, wherein the modification is M53Y.

6. The method of claim 1, wherein the modification is L61E.

7. The method of claim 1, wherein the modification is K93Q.

8. The method of claim 1, wherein the CTLA4 variant comprises a combination of substitutions selected from the group consisting of T51N/L61E/K93Q, A29H/T51N/L61E/K93Q, A29H/T51N, T51N/M53Y, and T51N/M53Y/L61E.

9. The method of claim 1, wherein the IgG is IgG1.

10. The method of claim 1, wherein the IgG is IgG2.

11. The method of claim 1, wherein the IgG is an IgG1/IgG2 hybrid.

12. The method of claim 1, wherein the B7-1 and/or B7-2 is expressed on peripheral blood monocyte cells (PBMCs).

13. The method of claim 8, wherein the CTLA4 variant comprises T51N/L61E/K93Q.

14. The method of claim 8, wherein the CTLA4 variant comprises A29H/T51N/L61E/K93Q.

15. The method of claim 8, wherein the CTLA4 variant comprises A29H/T51N.

16. The method of claim 8, wherein the CTLA4 variant comprises T51N/M53Y.

17. The method of claim 8, wherein the CTLA4 variant comprises T51N/M53Y/L61E.

18. The method of claim 8, wherein the CTLA4 variant further comprises a variant Fc region.

19. The method of claim 18, wherein the variant Fc region comprises an amino acid modification selected from the group consisting of 259I, 308F, 428L, and 434S.

20. The method of claim 19, wherein the modification is 434S.

21. The method of claim 19, wherein the modification is 428L/434S.

22. The method of claim 19, wherein the modification is 308F/259I.

23. The method of claim 19, wherein the modification is 259I/308F/428L.

* * * * *

SEQUENCE LISTING

```
<160> NUMBER OF SEQ ID NOS: 41

<210> SEQ ID NO 1
<211> LENGTH: 124
<212> TYPE: PRT
<213> ORGANISM: Artificial Sequence
<220> FEATURE:
<223> OTHER INFORMATION: First Domain of a Variant human CTLA4
<220> FEATURE:
<221> NAME/KEY: misc_feature
<222> LOCATION: (29)..(29)
<223> OTHER INFORMATION: where Xaa is alanine or histidine
<220> FEATURE:
<221> NAME/KEY: misc_feature
<222> LOCATION: (51)..(51)
<223> OTHER INFORMATION: where Xaa is threonine or asparagine
<220> FEATURE:
<221> NAME/KEY: misc_feature
<222> LOCATION: (53)..(53)
<223> OTHER INFORMATION: where Xaa is methionine or tyrosine
<220> FEATURE:
<221> NAME/KEY: misc_feature
<222> LOCATION: (61)..(61)
<223> OTHER INFORMATION: where Xaa is leucine or glutamic acid
<220> FEATURE:
<221> NAME/KEY: misc_feature
<222> LOCATION: (93)..(93)
<223> OTHER INFORMATION: where Xaa is lysine or glutamine

<400> SEQUENCE: 1

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Xaa Thr Glu Val
            20                  25                  30

Arg Val Thr Val Leu Arg Gln Ala Asp Ser Gln Val Thr Glu Val Cys
        35                  40                  45

Ala Ala Xaa Tyr Xaa Met Gly Asn Glu Leu Thr Phe Xaa Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Xaa Val Glu Leu
                85                  90                  95
```

```
Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 2
<211> LENGTH: 124
<212> TYPE: PRT
<213> ORGANISM: Artificial Sequence
<220> FEATURE:
<223> OTHER INFORMATION: First domain of a variant human CTLA4
<220> FEATURE:
<221> NAME/KEY: misc_feature
<222> LOCATION: (51)..(51)
<223> OTHER INFORMATION: where Xaa is threonine or asparagine
<220> FEATURE:
<221> NAME/KEY: misc_feature
<222> LOCATION: (53)..(53)
<223> OTHER INFORMATION: where Xaa is methionine or tyrosine
<220> FEATURE:
<221> NAME/KEY: misc_feature
<222> LOCATION: (61)..(61)
<223> OTHER INFORMATION: where Xaa is leucine or glutamic acid
<220> FEATURE:
<221> NAME/KEY: misc_feature
<222> LOCATION: (93)..(93)
<223> OTHER INFORMATION: where Xaa is lysine or glutamine

<400> SEQUENCE: 2

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys His Thr Glu Val
            20                  25                  30

Arg Val Thr Val Leu Arg Gln Ala Asp Ser Gln Val Thr Glu Val Cys
        35                  40                  45

Ala Ala Xaa Tyr Xaa Met Gly Asn Glu Leu Thr Phe Xaa Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Xaa Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 3
<211> LENGTH: 124
<212> TYPE: PRT
<213> ORGANISM: Artificial Sequence
<220> FEATURE:
<223> OTHER INFORMATION: First domain of a variant human CTLA4
<220> FEATURE:
<221> NAME/KEY: misc_feature
<222> LOCATION: (29)..(29)
<223> OTHER INFORMATION: where Xaa is alanine or histidine
<220> FEATURE:
<221> NAME/KEY: misc_feature
<222> LOCATION: (53)..(53)
<223> OTHER INFORMATION: where Xaa is methionine or tyrosine
<220> FEATURE:
<221> NAME/KEY: misc_feature
<222> LOCATION: (61)..(61)
<223> OTHER INFORMATION: where Xaa is leucine or glutamic acid
<220> FEATURE:
<221> NAME/KEY: misc_feature
<222> LOCATION: (93)..(93)
<223> OTHER INFORMATION: where Xaa is lysine or glutamine
```

-continued

```
<400> SEQUENCE: 3

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Xaa Thr Glu Val
            20                  25                  30

Arg Val Thr Val Leu Arg Gln Ala Asp Ser Gln Val Thr Glu Val Cys
        35                  40                  45

Ala Ala Asn Tyr Xaa Met Gly Asn Glu Leu Thr Phe Xaa Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Xaa Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 4
<211> LENGTH: 124
<212> TYPE: PRT
<213> ORGANISM: Artificial Sequence
<220> FEATURE:
<223> OTHER INFORMATION: First domain of a variant human CTLA4
<220> FEATURE:
<221> NAME/KEY: misc_feature
<222> LOCATION: (29)..(29)
<223> OTHER INFORMATION: where Xaa is alanine, glutamic acid,
      phenylanine, histidine, lysine, asparagine, glutamine, or arginine
<220> FEATURE:
<221> NAME/KEY: misc_feature
<222> LOCATION: (30)..(30)
<223> OTHER INFORMATION: where Xaa is threonine, histidine or valine
<220> FEATURE:
<221> NAME/KEY: misc_feature
<222> LOCATION: (31)..(31)
<223> OTHER INFORMATION: where Xaa is glutamic acid, aspartic acid,
      isoleucine, methionine, threonine, or valine
<220> FEATURE:
<221> NAME/KEY: misc_feature
<222> LOCATION: (33)..(33)
<223> OTHER INFORMATION: where Xaa is arginine, glutamic acid,
      phenylalanine, isoleucine, leucine, methionine, glutamine,
      threonine, tryptophan, or tyrosine
<220> FEATURE:
<221> NAME/KEY: misc_feature
<222> LOCATION: (35)..(35)
<223> OTHER INFORMATION: where Xaa is threonine, aspartic acid, glutamic
      acid, phenylalanine, methionine, valine or tyrosine
<220> FEATURE:
<221> NAME/KEY: misc_feature
<222> LOCATION: (49)..(49)
<223> OTHER INFORMATION: where Xaa is alanine, aspartic acid, glutamic
      acid, phenylalanine, threonine, tryptophan, or tyrosine
<220> FEATURE:
<221> NAME/KEY: misc_feature
<222> LOCATION: (51)..(51)
<223> OTHER INFORMATION: where Xaa is threonine, aspartic acid, glutamic
      acid, histidine, leucine, asparagine, glutamine, arginine, serine,
      or valine
<220> FEATURE:
<221> NAME/KEY: misc_feature
<222> LOCATION: (53)..(53)
<223> OTHER INFORMATION: where Xaa is methionine, glutamic acid,
      phenylalanine, histidine, glutamine, tryptophan, or tyrosine
<220> FEATURE:
<221> NAME/KEY: misc_feature
<222> LOCATION: (59)..(59)
<223> OTHER INFORMATION: where Xaa is threonine, histidine, isoleucine,
      leucine, asparagine, glutamine, valine, or tyrosine
<220> FEATURE:
```

-continued

```
<221> NAME/KEY: misc_feature
<222> LOCATION: (61)..(61)
<223> OTHER INFORMATION: where Xaa is leucine, alanine, glutamic acid,
      phynelalanine, glycine, histidine, isoleucine, lysine, methionine,
      asparagine, proline, glutamine, arginine, serine, threonine,
      valine, tryptophan, or tyrosine
<220> FEATURE:
<221> NAME/KEY: misc_feature
<222> LOCATION: (63)..(63)
<223> OTHER INFORMATION: where Xaa is aspartic acid or glutamic acid
<220> FEATURE:
<221> NAME/KEY: misc_feature
<222> LOCATION: (64)..(64)
<223> OTHER INFORMATION: where Xaa is serine, lysine, arginine or
      tyrosine
<220> FEATURE:
<221> NAME/KEY: misc_feature
<222> LOCATION: (93)..(93)
<223> OTHER INFORMATION: where Xaa is lysine, aspartic acid, glutamic
      acid, phenylalanine, histidine, asparagine, glutamine, arginine,
      serine, threonine, valine, tryptophan, or tyrosine
<220> FEATURE:
<221> NAME/KEY: misc_feature
<222> LOCATION: (95)..(95)
<223> OTHER INFORMATION: where Xaa is glutamic acid, aspartic acid,
      histidine, leucine, glutamine, or tyrosine
<220> FEATURE:
<221> NAME/KEY: misc_feature
<222> LOCATION: (97)..(97)
<223> OTHER INFORMATION: where Xaa is methionine, aspartic acid,
      phenylalanine, isoleucine, asparagine, or valine
<220> FEATURE:
<221> NAME/KEY: misc_feature
<222> LOCATION: (98)..(98)
<223> OTHER INFORMATION: where Xaa is tyrosine, phenlyalanine, or
      tryptophan
<220> FEATURE:
<221> NAME/KEY: misc_feature
<222> LOCATION: (102)..(102)
<223> OTHER INFORMATION: where Xaa is tyrosine, phenlyalanine, or
      tryptophan
<220> FEATURE:
<221> NAME/KEY: misc_feature
<222> LOCATION: (103)..(103)
<223> OTHER INFORMATION: where Xaa is tyrosine, aspartic acid, glutamic
      acid, phenylalanine, histidine, asparagine, glutamine, or
      tryptophan
<220> FEATURE:
<221> NAME/KEY: misc_feature
<222> LOCATION: (104)..(104)
<223> OTHER INFORMATION: where Xaa is leucine, phenlyalanine, histidine,
      methionine, valine, or tyrosine
<220> FEATURE:
<221> NAME/KEY: misc_feature
<222> LOCATION: (105)..(105)
<223> OTHER INFORMATION: where Xaa is glycine, aspartic acid, or
      glutamic acid
<220> FEATURE:
<221> NAME/KEY: misc_feature
<222> LOCATION: (106)..(106)
<223> OTHER INFORMATION: where Xaa is isoleucine, glutamic acid, or
      tyrosine

<400> SEQUENCE: 4

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Xaa Xaa Xaa Val
            20                  25                  30

Xaa Val Xaa Val Leu Arg Gln Ala Asp Ser Gln Val Thr Glu Val Cys
        35                  40                  45

Xaa Ala Xaa Tyr Xaa Met Gly Asn Glu Leu Xaa Phe Xaa Asp Xaa Xaa
    50                  55                  60

Ile Cys Thr Gly Thr Ser Ser Gly Asn Gln Val Asn Leu Thr Ile Gln
65                  70                  75                  80
```

```
Gly Leu Arg Ala Met Asp Thr Gly Leu Tyr Ile Cys Xaa Val Xaa Leu
                85                  90                  95

Xaa Xaa Pro Pro Pro Xaa Xaa Xaa Xaa Gly Asn Gly Thr Gln Ile
            100                 105                 110

Tyr Val Ile Asp Pro Glu Pro Cys Pro Asp Ser Asp
        115                 120

<210> SEQ ID NO 5
<211> LENGTH: 223
<212> TYPE: PRT
<213> ORGANISM: Homo sapiens

<400> SEQUENCE: 5

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
                20                  25                  30

Val Phe Cys Lys Ala Met His Val Ala Gln Pro Ala Val Val Leu Ala
            35                  40                  45

Ser Ser Arg Gly Ile Ala Ser Phe Val Cys Glu Tyr Ala Ser Pro Gly
        50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
210                 215                 220

<210> SEQ ID NO 6
<211> LENGTH: 124
<212> TYPE: PRT
<213> ORGANISM: Homo sapiens

<400> SEQUENCE: 6

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Asp Ser
        50                  55                  60

Ile Cys Thr Gly Thr Ser Ser Gly Asn Gln Val Asn Leu Thr Ile Gln
```

```
                65                  70                  75                  80
Gly Leu Arg Ala Met Asp Thr Gly Leu Tyr Ile Cys Lys Val Glu Leu
                    85                  90                  95

Met Tyr Pro Pro Pro Tyr Tyr Leu Gly Ile Gly Asn Gly Thr Gln Ile
                100                 105                 110

Tyr Val Ile Asp Pro Glu Pro Cys Pro Asp Ser Asp
            115                 120

<210> SEQ ID NO 7
<211> LENGTH: 124
<212> TYPE: PRT
<213> ORGANISM: Homo sapiens

<400> SEQUENCE: 7

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Tyr Thr Glu Val
                20                  25                  30

Arg Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Asp Ser
        50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                    85                  90                  95

Met Tyr Pro Pro Pro Tyr Tyr Glu Gly Ile Gly Asn Gly Thr Gln Ile
                100                 105                 110

Tyr Val Ile Asp Pro Glu Pro Cys Pro Asp Ser Asp
            115                 120

<210> SEQ ID NO 8
<211> LENGTH: 124
<212> TYPE: PRT
<213> ORGANISM: Artificial Sequence
<220> FEATURE:
<223> OTHER INFORMATION: Consensus sequence
<220> FEATURE:
<221> NAME/KEY: misc_feature
<222> LOCATION: (29)..(29)
<223> OTHER INFORMATION: where Xaa is alanine or histidine
<220> FEATURE:
<221> NAME/KEY: misc_feature
<222> LOCATION: (51)..(51)
<223> OTHER INFORMATION: where Xaa is threonine or asparagine
<220> FEATURE:
<221> NAME/KEY: misc_feature
<222> LOCATION: (53)..(53)
<223> OTHER INFORMATION: where Xaa is methionine or tyrosine
<220> FEATURE:
<221> NAME/KEY: misc_feature
<222> LOCATION: (61)..(61)
<223> OTHER INFORMATION: where Xaa is leucine or glutamic acid
<220> FEATURE:
<221> NAME/KEY: misc_feature
<222> LOCATION: (93)..(93)
<223> OTHER INFORMATION: where Xaa is lysine or glutamine

<400> SEQUENCE: 8

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Xaa Thr Glu Val
                20                  25                  30

Arg Val Thr Val Leu Arg Gln Ala Asp Ser Gln Val Thr Glu Val Cys
```

```
            35                  40                  45
Ala Ala Xaa Tyr Xaa Met Gly Asn Glu Leu Thr Phe Xaa Asp Asp Ser
 50                  55                  60

Ile Cys Thr Gly Thr Ser Ser Gly Asn Gln Val Asn Leu Thr Ile Gln
 65                  70                  75                  80

Gly Leu Arg Ala Met Asp Thr Gly Leu Tyr Ile Cys Xaa Val Glu Leu
                 85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 9
<211> LENGTH: 218
<212> TYPE: PRT
<213> ORGANISM: Homo sapiens

<400> SEQUENCE: 9

Pro Ala Pro Glu Leu Leu Gly Gly Pro Ser Val Phe Leu Phe Pro Pro
  1               5                  10                  15

Lys Pro Lys Asp Thr Leu Met Ile Ser Arg Thr Pro Glu Val Thr Cys
             20                  25                  30

Val Val Val Asp Val Ser His Glu Asp Pro Glu Val Lys Phe Asn Trp
         35                  40                  45

Tyr Val Asp Gly Val Glu Val His Asn Ala Lys Thr Lys Pro Arg Glu
     50                  55                  60

Glu Gln Tyr Asn Ser Thr Tyr Arg Val Val Ser Val Leu Thr Val Leu
 65                  70                  75                  80

His Gln Asp Trp Leu Asn Gly Lys Glu Tyr Lys Cys Lys Val Ser Asn
                 85                  90                  95

Lys Ala Leu Pro Ala Pro Ile Glu Lys Thr Ile Ser Lys Ala Lys Gly
            100                 105                 110

Gln Pro Arg Glu Pro Gln Val Tyr Thr Leu Pro Pro Ser Arg Asp Glu
        115                 120                 125

Leu Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215

<210> SEQ ID NO 10
<211> LENGTH: 217
<212> TYPE: PRT
<213> ORGANISM: Homo sapiens

<400> SEQUENCE: 10

Pro Ala Pro Pro Val Ala Gly Pro Ser Val Phe Leu Phe Pro Pro Lys
  1               5                  10                  15

Pro Lys Asp Thr Leu Met Ile Ser Arg Thr Pro Glu Val Thr Cys Val
             20                  25                  30
```

Val Val Asp Val Ser His Glu Asp Pro Glu Val Gln Phe Asn Trp Tyr
            35                  40                  45

Val Asp Gly Val Glu Val His Asn Ala Lys Thr Lys Pro Arg Glu Glu
 50                  55                  60

Gln Phe Asn Ser Thr Phe Arg Val Val Ser Val Leu Thr Val Val His
 65                  70                  75                  80

Gln Asp Trp Leu Asn Gly Lys Glu Tyr Lys Cys Lys Val Ser Asn Lys
                85                  90                  95

Gly Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
            115                 120                 125

Thr Lys Asn Gln Val Ser Leu Thr Cys Leu Val Lys Gly Phe Tyr Pro
            130                 135                 140

Ser Asp Ile Ala Val Glu Trp Glu Ser Asn Gly Gln Pro Glu Asn Asn
145                 150                 155                 160

Tyr Lys Thr Thr Pro Pro Met Leu Asp Ser Asp Gly Ser Phe Phe Leu
            165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
            210                 215

<210> SEQ ID NO 11
<211> LENGTH: 218
<212> TYPE: PRT
<213> ORGANISM: Homo sapiens

<400> SEQUENCE: 11

Pro Ala Pro Glu Leu Leu Gly Gly Pro Ser Val Phe Leu Phe Pro Pro
 1                   5                  10                  15

Lys Pro Lys Asp Thr Leu Met Ile Ser Arg Thr Pro Glu Val Thr Cys
             20                  25                  30

Val Val Val Asp Val Ser His Glu Asp Pro Glu Val Gln Phe Lys Trp
            35                  40                  45

Tyr Val Asp Gly Val Glu Val His Asn Ala Lys Thr Lys Pro Arg Glu
 50                  55                  60

Glu Gln Tyr Asn Ser Thr Phe Arg Val Val Ser Val Leu Thr Val Leu
 65                  70                  75                  80

His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Thr Lys Gly
            100                 105                 110

Gln Pro Arg Glu Pro Gln Val Tyr Thr Leu Pro Pro Ser Arg Glu Glu
            115                 120                 125

Met Thr Lys Asn Gln Val Ser Leu Thr Cys Leu Val Lys Gly Phe Tyr
            130                 135                 140

Pro Ser Asp Ile Ala Val Glu Trp Glu Ser Ser Gly Gln Pro Glu Asn
145                 150                 155                 160

Asn Tyr Asn Thr Thr Pro Pro Met Leu Asp Ser Asp Gly Ser Phe Phe
            165                 170                 175

Leu Tyr Ser Lys Leu Thr Val Asp Lys Ser Arg Trp Gln Gln Gly Asn
            180                 185                 190

```
Ile Phe Ser Cys Ser Val Met His Glu Ala Leu His Asn Arg Phe Thr
            195                 200                 205

Gln Lys Ser Leu Ser Leu Ser Pro Gly Lys
            210                 215

<210> SEQ ID NO 12
<211> LENGTH: 218
<212> TYPE: PRT
<213> ORGANISM: Homo sapiens

<400> SEQUENCE: 12

Pro Ala Pro Glu Phe Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser Gln Glu Asp Pro Glu Val Gln Phe Asn Trp
        35                  40                  45

Tyr Val Asp Gly Val Glu Val His Asn Ala Lys Thr Lys Pro Arg Glu
    50                  55                  60

Glu Gln Phe Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Gly Leu Pro Ser Ser Ile Glu Lys Thr Ile Ser Lys Ala Lys Gly
            100                 105                 110

Gln Pro Arg Glu Pro Gln Val Tyr Thr Leu Pro Pro Ser Gln Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Arg Leu Thr Val Asp Lys Ser Arg Trp Gln Glu Gly Asn
            180                 185                 190

Val Phe Ser Cys Ser Val Met His Glu Ala Leu His Asn His Tyr Thr
        195                 200                 205

Gln Lys Ser Leu Ser Leu Ser Leu Gly Lys
    210                 215

<210> SEQ ID NO 13
<211> LENGTH: 218
<212> TYPE: PRT
<213> ORGANISM: Homo sapiens

<400> SEQUENCE: 13

Pro Ala Pro Glu Leu Leu Gly Gly Ser Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Lys Phe Asn Trp
        35                  40                  45

Tyr Val Asp Gly Val Glu Val His Asn Ala Lys Thr Lys Pro Arg Glu
    50                  55                  60

Glu Gln Tyr Asn Ser Thr Tyr Arg Val Val Ser Val Leu Thr Val Leu
65                  70                  75                  80
```

-continued

```
His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Ala Lys Gly
            100                 105                 110

Gln Pro Arg Glu Pro Gln Val Tyr Thr Leu Pro Pro Ser Arg Asp Glu
        115                 120                 125

Leu Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215
```

```
<210> SEQ ID NO 14
<211> LENGTH: 218
<212> TYPE: PRT
<213> ORGANISM: Homo sapiens

<400> SEQUENCE: 14
```

```
Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Gln Phe Asn Trp
        35                  40                  45

Tyr Val Asp Gly Val Glu Val His Asn Ala Lys Thr Lys Pro Arg Glu
    50                  55                  60

Glu Gln Phe Asn Ser Thr Phe Arg Val Val Ser Val Leu Thr Val Val
65                  70                  75                  80

His Gln Asp Trp Leu Asn Gly Lys Glu Tyr Lys Cys Lys Val Ser Asn
                85                  90                  95

Lys Gly Leu Pro Ala Pro Ile Glu Lys Thr Ile Ser Lys Thr Lys Gly
            100                 105                 110

Gln Pro Arg Glu Pro Gln Val Tyr Thr Leu Pro Pro Ser Arg Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Met Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215
```

```
<210> SEQ ID NO 15
<211> LENGTH: 218
```

<212> TYPE: PRT
<213> ORGANISM: Homo sapiens

<400> SEQUENCE: 15

```
Pro Ala Pro Glu Leu Leu Gly Gly Ser Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Gln Phe Asn Trp
        35                  40                  45

Tyr Val Asp Gly Val Glu Val His Asn Ala Lys Thr Lys Pro Arg Glu
    50                  55                  60

Glu Gln Phe Asn Ser Thr Phe Arg Val Val Ser Val Leu Thr Val Val
65                  70                  75                  80

His Gln Asp Trp Leu Asn Gly Lys Glu Tyr Lys Cys Lys Val Ser Asn
                85                  90                  95

Lys Gly Leu Pro Ala Pro Ile Glu Lys Thr Ile Ser Lys Thr Lys Gly
            100                 105                 110

Gln Pro Arg Glu Pro Gln Val Tyr Thr Leu Pro Pro Ser Arg Glu Glu
        115                 120                 125

Met Thr Lys Asn Gln Val Ser Leu Thr Cys Leu Val Lys Gly Phe Tyr
130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Met Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215
```

<210> SEQ ID NO 16
<211> LENGTH: 14
<212> TYPE: PRT
<213> ORGANISM: Artificial Sequence
<220> FEATURE:
<223> OTHER INFORMATION: Linker(IgG1) (EU numbering 216-229)

<400> SEQUENCE: 16

```
Glu Pro Lys Ser Cys Asp Lys Thr His Thr Cys Pro Pro Cys
1               5                   10
```

<210> SEQ ID NO 17
<211> LENGTH: 11
<212> TYPE: PRT
<213> ORGANISM: Artificial Sequence
<220> FEATURE:
<223> OTHER INFORMATION: Linker(IgG2) (EU numbering 216-229)

<400> SEQUENCE: 17

```
Glu Arg Lys Cys Cys Val Glu Cys Pro Pro Cys
1               5                   10
```

<210> SEQ ID NO 18
<211> LENGTH: 61
<212> TYPE: PRT
<213> ORGANISM: Artificial Sequence
<220> FEATURE:
<223> OTHER INFORMATION: Linker(IgG3) (EU numbering 216-229)

<400> SEQUENCE: 18

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys
    50                  55                  60

<210> SEQ ID NO 19
<211> LENGTH: 11
<212> TYPE: PRT
<213> ORGANISM: Artificial Sequence
<220> FEATURE:
<223> OTHER INFORMATION: Linker(IgG4) (EU numbering 216-229)

<400> SEQUENCE: 19

Glu Ser Lys Tyr Gly Pro Pro Cys Pro Ser Cys
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Linker(IgG1-220S/226S/229S) (EU numbering
      216-229)

<400> SEQUENCE: 20

Glu Pro Lys Ser Ser Asp Lys Thr His Thr Ser Pro Pro Ser
1               5                   10

<210> SEQ ID NO 21
<211> LENGTH: 11
<212> TYPE: PRT
<213> ORGANISM: Artificial Sequence
<220> FEATURE:
<223> OTHER INFORMATION: LINKER(IGG2-219S/220S/226S/229S)

<400> SEQUENCE: 21

Glu Arg Lys Ser Ser Val Glu Ser Pro Pro Ser
1               5                   10

<210> SEQ ID NO 22
<211> LENGTH: 15
<212> TYPE: PRT
<213> ORGANISM: Artificial Sequence
<220> FEATURE:
<223> OTHER INFORMATION: Linker(Q-IgG1-220S/226S/229S) (aka abatacept
      linker)

<400> SEQUENCE: 22

Gln Glu Pro Lys Ser Ser Asp Lys Thr His Thr Ser Pro Pro Ser
1               5                   10                  15

<210> SEQ ID NO 23
<211> LENGTH: 12
<212> TYPE: PRT
<213> ORGANISM: Artificial Sequence
<220> FEATURE:
<223> OTHER INFORMATION: Linker(Q-IgG2-219S/220S/226S/229S)

<400> SEQUENCE: 23

Gln Glu Arg Lys Ser Ser Val Glu Ser Pro Pro Ser

<210> SEQ ID NO 24
<211> LENGTH: 233
<212> TYPE: PRT
<213> ORGANISM: Artificial Sequence
<220> FEATURE:
<223> OTHER INFORMATION: Ig(ab) [Linker(Q-IgG1-220S/226S/229S)+
Fc(IgG1-238S)

<400> SEQUENCE: 24

```
Gln Glu Pro Lys Ser Ser Asp Lys Thr His Thr Ser Pro Ser Pro
1               5                   10                  15

Ala Pro Glu Leu Leu Gly Gly Ser Ser Val Phe Leu Phe Pro Pro Lys
                20                  25                  30

Pro Lys Asp Thr Leu Met Ile Ser Arg Thr Pro Glu Val Thr Cys Val
            35                  40                  45

Val Val Asp Val Ser His Glu Asp Pro Glu Val Lys Phe Asn Trp Tyr
50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230
```

<210> SEQ ID NO 25
<211> LENGTH: 233
<212> TYPE: PRT
<213> ORGANISM: Artificial Sequence
<220> FEATURE:
<223> OTHER INFORMATION: Ig(ab-238P) [Linker(Q-IgG1-220S/226S/229S)+
Fc(IgG1)]

<400> SEQUENCE: 25

```
Gln Glu Pro Lys Ser Ser Asp Lys Thr His Thr Ser Pro Ser Pro
1               5                   10                  15

Ala Pro Glu Leu Leu Gly Gly Pro Ser Val Phe Leu Phe Pro Pro Lys
                20                  25                  30

Pro Lys Asp Thr Leu Met Ile Ser Arg Thr Pro Glu Val Thr Cys Val
            35                  40                  45

Val Val Asp Val Ser His Glu Asp Pro Glu Val Lys Phe Asn Trp Tyr
50                  55                  60
```

```
Val Asp Gly Val Glu Val His Asn Ala Lys Thr Lys Pro Arg Glu Glu
 65                  70                  75                  80

Gln Tyr Asn Ser Thr Tyr Arg Val Val Ser Val Leu Thr Val Leu His
             85                  90                  95

Gln Asp Trp Leu Asn Gly Lys Glu Tyr Lys Cys Lys Val Ser Asn Lys
        100                 105                 110

Ala Leu Pro Ala Pro Ile Glu Lys Thr Ile Ser Lys Ala Lys Gly Gln
    115                 120                 125

Pro Arg Glu Pro Gln Val Tyr Thr Leu Pro Pro Ser Arg Asp Glu Leu
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230
```

<210> SEQ ID NO 26
<211> LENGTH: 229
<212> TYPE: PRT
<213> ORGANISM: Artificial Sequence
<220> FEATURE:
<223> OTHER INFORMATION: Ig(G2) [Linker(Q-IgG2-219S/220S/226S/229S)+
      Fc(IgG2)]

<400> SEQUENCE: 26

```
Gln Glu Arg Lys Ser Ser Val Glu Ser Pro Pro Ser Pro Ala Pro Pro
1               5                   10                  15

Val Ala Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser His Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Phe Arg Val Val Ser Val Leu Thr Val Val His Gln Asp Trp Leu
                85                  90                  95

Asn Gly Lys Glu Tyr Lys Cys Lys Val Ser Asn Lys Gly Leu Pro Ala
            100                 105                 110

Pro Ile Glu Lys Thr Ile Ser Lys Thr Lys Gly Gln Pro Arg Glu Pro
        115                 120                 125

Gln Val Tyr Thr Leu Pro Pro Ser Arg Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Met Leu Asp Ser Asp Gly Ser Phe Phe Leu Tyr Ser Lys Leu
            180                 185                 190
```

```
Thr Val Asp Lys Ser Arg Trp Gln Gln Gly Asn Val Phe Ser Cys Ser
            195                 200                 205

Val Met His Glu Ala Leu His Asn His Tyr Thr Gln Lys Ser Leu Ser
    210                 215                 220

Leu Ser Pro Gly Lys
225

<210> SEQ ID NO 27
<211> LENGTH: 233
<212> TYPE: PRT
<213> ORGANISM: Artificial Sequence
<220> FEATURE:
<223> OTHER INFORMATION: Ig(G2-ELLG)
      [Linker(Q-IgG1-220S/226S/229S)+Fc(IgG2-233E/234L/235L/236G)]

<400> SEQUENCE: 27

Gln Glu Pro Lys Ser Ser Asp Lys Thr His Thr Ser Pro Pro Ser Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Gln Phe Asn Trp Tyr
50                  55                  60

Val Asp Gly Val Glu Val His Asn Ala Lys Thr Lys Pro Arg Glu Glu
65                  70                  75                  80

Gln Phe Asn Ser Thr Phe Arg Val Val Ser Val Leu Thr Val Val His
                85                  90                  95

Gln Asp Trp Leu Asn Gly Lys Glu Tyr Lys Cys Lys Val Ser Asn Lys
            100                 105                 110

Gly Leu Pro Ala Pro Ile Glu Lys Thr Ile Ser Lys Thr Lys Gly Gln
        115                 120                 125

Pro Arg Glu Pro Gln Val Tyr Thr Leu Pro Pro Ser Arg Glu Glu Met
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Met Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
210                 215                 220

Lys Ser Leu Ser Leu Ser Pro Gly Lys
225                 230

<210> SEQ ID NO 28
<211> LENGTH: 357
<212> TYPE: PRT
<213> ORGANISM: Artificial Sequence
<220> FEATURE:
<223> OTHER INFORMATION: Abatacept CTLA4-Ig(ab) (XENP8420)

<400> SEQUENCE: 28

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
```

```
                    20                  25                  30
Arg Val Thr Val Leu Arg Gln Ala Asp Ser Gln Val Thr Glu Val Cys
            35                  40                  45
Ala Ala Thr Tyr Met Met Gly Asn Glu Leu Thr Phe Leu Asp Asp Ser
        50                  55                  60
Ile Cys Thr Gly Thr Ser Ser Gly Asn Gln Val Asn Leu Thr Ile Gln
65                  70                  75                  80
Gly Leu Arg Ala Met Asp Thr Gly Leu Tyr Ile Cys Lys Val Glu Leu
                85                  90                  95
Met Tyr Pro Pro Pro Tyr Tyr Leu Gly Ile Gly Asn Gly Thr Gln Ile
            100                 105                 110
Tyr Val Ile Asp Pro Glu Pro Cys Pro Asp Ser Asp Gln Glu Pro Lys
        115                 120                 125
Ser Ser Asp Lys Thr His Thr Ser Pro Pro Ser Pro Ala Pro Glu Leu
    130                 135                 140
Leu Gly Gly Ser Ser Val Phe Leu Phe Pro Pro Lys Pro Lys Asp Thr
145                 150                 155                 160
Leu Met Ile Ser Arg Thr Pro Glu Val Thr Cys Val Val Val Asp Val
                165                 170                 175
Ser His Glu Asp Pro Glu Val Lys Phe Asn Trp Tyr Val Asp Gly Val
            180                 185                 190
Glu Val His Asn Ala Lys Thr Lys Pro Arg Glu Glu Gln Tyr Asn Ser
        195                 200                 205
Thr Tyr Arg Val Val Ser Val Leu Thr Val Leu His Gln Asp Trp Leu
    210                 215                 220
Asn Gly Lys Glu Tyr Lys Cys Lys Val Ser Asn Lys Ala Leu Pro Ala
225                 230                 235                 240
Pro Ile Glu Lys Thr Ile Ser Lys Ala Lys Gly Gln Pro Arg Glu Pro
                245                 250                 255
Gln Val Tyr Thr Leu Pro Pro Ser Arg Asp Glu Leu Thr Lys Asn Gln
            260                 265                 270
Val Ser Leu Thr Cys Leu Val Lys Gly Phe Tyr Pro Ser Asp Ile Ala
        275                 280                 285
Val Glu Trp Glu Ser Asn Gly Gln Pro Glu Asn Asn Tyr Lys Thr Thr
    290                 295                 300
Pro Pro Val Leu Asp Ser Asp Gly Ser Phe Phe Leu Tyr Ser Lys Leu
305                 310                 315                 320
Thr Val Asp Lys Ser Arg Trp Gln Gln Gly Asn Val Phe Ser Cys Ser
                325                 330                 335
Val Met His Glu Ala Leu His Asn His Tyr Thr Gln Lys Ser Leu Ser
            340                 345                 350
Leu Ser Pro Gly Lys
        355

<210> SEQ ID NO 29
<211> LENGTH: 353
<212> TYPE: PRT
<213> ORGANISM: Artificial Sequence
<220> FEATURE:
<223> OTHER INFORMATION: CTLA4-Ig(G2) (XENP8445)

<400> SEQUENCE: 29

Met His Val Ala Gln Pro Ala Val Val Leu Ala Ser Ser Arg Gly Ile
1               5                   10                  15
Ala Ser Phe Val Cys Glu Tyr Ala Ser Pro Gly Lys Ala Thr Glu Val
                20                  25                  30
```

Arg Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Asp Ser
 50                  55                  60

Ile Cys Thr Gly Thr Ser Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
                 85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Gln Glu Arg Lys
            115                 120                 125

Ser Ser Val Glu Ser Pro Pro Ser Pro Ala Pro Val Ala Gly Pro
            130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser His Glu Asp
                165                 170                 175

Pro Glu Val Gln Phe Asn Trp Tyr Val Asp Gly Val Glu Val His Asn
            180                 185                 190

Ala Lys Thr Lys Pro Arg Glu Glu Gln Phe Asn Ser Thr Phe Arg Val
        195                 200                 205

Val Ser Val Leu Thr Val Val His Gln Asp Trp Leu Asn Gly Lys Glu
210                 215                 220

Tyr Lys Cys Lys Val Ser Asn Lys Gly Leu Pro Ala Pro Ile Glu Lys
225                 230                 235                 240

Thr Ile Ser Lys Thr Lys Gly Gln Pro Arg Glu Pro Gln Val Tyr Thr
                245                 250                 255

Leu Pro Pro Ser Arg Glu Glu Met Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Met Leu
290                 295                 300

Asp Ser Asp Gly Ser Phe Phe Leu Tyr Ser Lys Leu Thr Val Asp Lys
305                 310                 315                 320

Ser Arg Trp Gln Gln Gly Asn Val Phe Ser Cys Ser Val Met His Glu
                325                 330                 335

Ala Leu His Asn His Tyr Thr Gln Lys Ser Leu Ser Leu Ser Pro Gly
            340                 345                 350

Lys

<210> SEQ ID NO 30
<211> LENGTH: 357
<212> TYPE: PRT
<213> ORGANISM: Artificial Sequence
<220> FEATURE:
<223> OTHER INFORMATION: Belatacept CTLA4(29Y/104E)-Ig(ab) (XENP8448)

<400> SEQUENCE: 30

Met His Val Ala Gln Pro Ala Val Val Leu Ala Ser Ser Arg Gly Ile
 1               5                  10                  15

Ala Ser Phe Val Cys Glu Tyr Ala Ser Pro Gly Lys Tyr Thr Glu Val
             20                  25                  30

Arg Val Thr Val Leu Arg Gln Ala Asp Ser Gln Val Thr Glu Val Cys

```
                35                  40                  45
Ala Ala Thr Tyr Met Met Gly Asn Glu Leu Thr Phe Leu Asp Asp Ser
 50                  55                  60

Ile Cys Thr Gly Thr Ser Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
                 85                  90                  95

Met Tyr Pro Pro Pro Tyr Glu Gly Ile Gly Asn Gly Thr Gln Ile
                100                 105                 110

Tyr Val Ile Asp Pro Glu Pro Cys Pro Asp Ser Asp Gln Glu Pro Lys
                115                 120                 125

Ser Ser Asp Lys Thr His Thr Ser Pro Pro Ser Pro Ala Pro Glu Leu
130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
                180                 185                 190

Glu Val His Asn Ala Lys Thr Lys Pro Arg Glu Glu Gln Tyr Asn Ser
                195                 200                 205

Thr Tyr Arg Val Val Ser Val Leu Thr Val Leu His Gln Asp Trp Leu
210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
                260                 265                 270

Val Ser Leu Thr Cys Leu Val Lys Gly Phe Tyr Pro Ser Asp Ile Ala
                275                 280                 285

Val Glu Trp Glu Ser Asn Gly Gln Pro Glu Asn Asn Tyr Lys Thr Thr
290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
                340                 345                 350

Leu Ser Pro Gly Lys
        355

<210> SEQ ID NO 31
<211> LENGTH: 124
<212> TYPE: PRT
<213> ORGANISM: Artificial Sequence
<220> FEATURE:
<223> OTHER INFORMATION: CTLA4(HNEQ) (29H/51N/61E/93Q) (H1.135)

<400> SEQUENCE: 31

Met His Val Ala Gln Pro Ala Val Val Leu Ala Ser Ser Arg Gly Ile
 1               5                  10                  15

Ala Ser Phe Val Cys Glu Tyr Ala Ser Pro Gly Lys His Thr Glu Val
                 20                  25                  30

Arg Val Thr Val Leu Arg Gln Ala Asp Ser Gln Val Thr Glu Val Cys
                 35                  40                  45
```

Ala Ala Asn Tyr Met Met Gly Asn Glu Leu Thr Phe Glu Asp Asp Ser
        50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Gln Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 32
<211> LENGTH: 124
<212> TYPE: PRT
<213> ORGANISM: Artificial Sequence
<220> FEATURE:
<223> OTHER INFORMATION: CTLA4(NEQ) (51N/61E/93Q) (H1.144)

<400> SEQUENCE: 32

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Asn Tyr Met Met Gly Asn Glu Leu Thr Phe Glu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Gln Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 33
<211> LENGTH: 357
<212> TYPE: PRT
<213> ORGANISM: Artificial Sequence
<220> FEATURE:
<223> OTHER INFORMATION: CTLA4(HNEQ)-Ig(ab) (XENP9360)

<400> SEQUENCE: 33

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys His Thr Glu Val
            20                  25                  30

Arg Val Thr Val Leu Arg Gln Ala Asp Ser Gln Val Thr Glu Val Cys
        35                  40                  45

Ala Ala Asn Tyr Met Met Gly Asn Glu Leu Thr Phe Glu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Gln Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Gln Glu Pro Lys
115                 120                 125

Ser Ser Asp Lys Thr His Thr Ser Pro Pro Ser Pro Ala Pro Glu Leu
130                 135                 140

Leu Gly Gly Ser Ser Val Phe Leu Phe Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
                180                 185                 190

Glu Val His Asn Ala Lys Thr Lys Pro Arg Glu Glu Gln Tyr Asn Ser
            195                 200                 205

Thr Tyr Arg Val Val Ser Val Leu Thr Val Leu His Gln Asp Trp Leu
            210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
                260                 265                 270

Val Ser Leu Thr Cys Leu Val Lys Gly Phe Tyr Pro Ser Asp Ile Ala
            275                 280                 285

Val Glu Trp Glu Ser Asn Gly Gln Pro Glu Asn Asn Tyr Lys Thr Thr
            290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355

<210> SEQ ID NO 34
<211> LENGTH: 357
<212> TYPE: PRT
<213> ORGANISM: Artificial Sequence
<220> FEATURE:
<223> OTHER INFORMATION: CTLA4(NEQ)-Ig(ab) (XENP9369)

<400> SEQUENCE: 34

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
            35                  40                  45

Ala Ala Asn Tyr Met Met Gly Asn Glu Leu Thr Phe Glu Asp Asp Ser
        50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Gln Val Glu Leu
                85                  90                  95

Met Tyr Pro Pro Pro Tyr Tyr Leu Gly Ile Gly Asn Gly Thr Gln Ile
                100                 105                 110

```
Tyr Val Ile Asp Pro Glu Pro Cys Pro Asp Ser Asp Gln Glu Pro Lys
            115                 120                 125

Ser Ser Asp Lys Thr His Thr Ser Pro Pro Ser Pro Ala Pro Glu Leu
130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
            165                 170                 175

Ser His Glu Asp Pro Glu Val Lys Phe Asn Trp Tyr Val Asp Gly Val
        180                 185                 190

Glu Val His Asn Ala Lys Thr Lys Pro Arg Glu Glu Gln Tyr Asn Ser
    195                 200                 205

Thr Tyr Arg Val Val Ser Val Leu Thr Val Leu His Gln Asp Trp Leu
210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
            245                 250                 255

Gln Val Tyr Thr Leu Pro Pro Ser Arg Asp Glu Leu Thr Lys Asn Gln
        260                 265                 270

Val Ser Leu Thr Cys Leu Val Lys Gly Phe Tyr Pro Ser Asp Ile Ala
    275                 280                 285

Val Glu Trp Glu Ser Asn Gly Gln Pro Glu Asn Asn Tyr Lys Thr Thr
290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
            325                 330                 335

Val Met His Glu Ala Leu His Asn His Tyr Thr Gln Lys Ser Leu Ser
        340                 345                 350

Leu Ser Pro Gly Lys
        355

<210> SEQ ID NO 35
<211> LENGTH: 357
<212> TYPE: PRT
<213> ORGANISM: Artificial Sequence
<220> FEATURE:
<223> OTHER INFORMATION: Abatacept CTLA4-Ig(ab-428L/434S) (XENP8441)

<400> SEQUENCE: 35

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
            85                  90                  95

Met Tyr Pro Pro Pro Tyr Tyr Leu Gly Ile Gly Asn Gly Thr Gln Ile
        100                 105                 110

Tyr Val Ile Asp Pro Glu Pro Cys Pro Asp Ser Asp Gln Glu Pro Lys
```

```
                  115                 120                 125
Ser Ser Asp Lys Thr His Thr Ser Pro Pro Ser Pro Ala Pro Glu Leu
        130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
        180                 185                 190

Glu Val His Asn Ala Lys Thr Lys Pro Arg Glu Glu Gln Tyr Asn Ser
                195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
        260                 265                 270

Val Ser Leu Thr Cys Leu Val Lys Gly Phe Tyr Pro Ser Asp Ile Ala
    275                 280                 285

Val Glu Trp Glu Ser Asn Gly Gln Pro Glu Asn Asn Tyr Lys Thr Thr
290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Leu His Glu Ala Leu His Ser His Tyr Thr Gln Lys Ser Leu Ser
        340                 345                 350

Leu Ser Pro Gly Lys
        355

<210> SEQ ID NO 36
<211> LENGTH: 353
<212> TYPE: PRT
<213> ORGANISM: Artificial Sequence
<220> FEATURE:
<223> OTHER INFORMATION: CTLA4-Ig(G2-428L/434S) (XENP8447)

<400> SEQUENCE: 36

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Asp Ser
        50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
                100                 105                 110

Tyr Val Ile Asp Pro Glu Pro Cys Pro Asp Ser Asp Gln Glu Arg Lys
            115                 120                 125
```

```
Ser Ser Val Glu Ser Pro Pro Ser Pro Ala Pro Pro Val Ala Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser His Glu Asp
                165                 170                 175

Pro Glu Val Gln Phe Asn Trp Tyr Val Asp Gly Val Glu Val His Asn
            180                 185                 190

Ala Lys Thr Lys Pro Arg Glu Glu Gln Phe Asn Ser Thr Phe Arg Val
        195                 200                 205

Val Ser Val Leu Thr Val Val His Gln Asp Trp Leu Asn Gly Lys Glu
    210                 215                 220

Tyr Lys Cys Lys Val Ser Asn Lys Gly Leu Pro Ala Pro Ile Glu Lys
225                 230                 235                 240

Thr Ile Ser Lys Thr Lys Gly Gln Pro Arg Glu Pro Gln Val Tyr Thr
                245                 250                 255

Leu Pro Pro Ser Arg Glu Glu Met Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Met Leu
290                 295                 300

Asp Ser Asp Gly Ser Phe Phe Leu Tyr Ser Lys Leu Thr Val Asp Lys
305                 310                 315                 320

Ser Arg Trp Gln Gln Gly Asn Val Phe Ser Cys Ser Val Leu His Glu
                325                 330                 335

Ala Leu His Ser His Tyr Thr Gln Lys Ser Leu Ser Leu Ser Pro Gly
            340                 345                 350

Lys

<210> SEQ ID NO 37
<211> LENGTH: 357
<212> TYPE: PRT
<213> ORGANISM: Artificial Sequence
<220> FEATURE:
<223> OTHER INFORMATION: CTLA4(HNEQ)-Ig(G2-ELLG-428L/434S) (XENP9523)

<400> SEQUENCE: 37

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys His Thr Glu Val
            20                  25                  30

Arg Val Thr Val Leu Arg Gln Ala Asp Ser Gln Val Thr Glu Val Cys
        35                  40                  45

Ala Ala Asn Tyr Met Met Gly Asn Glu Leu Thr Phe Glu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Gln Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Gln Glu Pro Lys
        115                 120                 125

Ser Ser Asp Lys Thr His Thr Ser Pro Pro Ser Pro Ala Pro Glu Leu
```

```
                130                 135                 140
Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Gln Phe Asn Trp Tyr Val Asp Gly Val
                180                 185                 190

Glu Val His Asn Ala Lys Thr Lys Pro Arg Glu Glu Gln Phe Asn Ser
                195                 200                 205

Thr Phe Arg Val Val Ser Val Leu Thr Val Val His Gln Asp Trp Leu
            210                 215                 220

Asn Gly Lys Glu Tyr Lys Cys Lys Val Ser Asn Lys Gly Leu Pro Ala
225                 230                 235                 240

Pro Ile Glu Lys Thr Ile Ser Lys Thr Lys Gly Gln Pro Arg Glu Pro
                245                 250                 255

Gln Val Tyr Thr Leu Pro Pro Ser Arg Glu Glu Met Thr Lys Asn Gln
                260                 265                 270

Val Ser Leu Thr Cys Leu Val Lys Gly Phe Tyr Pro Ser Asp Ile Ala
            275                 280                 285

Val Glu Trp Glu Ser Asn Gly Gln Pro Glu Asn Asn Tyr Lys Thr Thr
            290                 295                 300

Pro Pro Met Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Leu His Glu Ala Leu His Ser His Tyr Thr Gln Lys Ser Leu Ser
                340                 345                 350

Leu Ser Pro Gly Lys
            355

<210> SEQ ID NO 38
<211> LENGTH: 357
<212> TYPE: PRT
<213> ORGANISM: Artificial Sequence
<220> FEATURE:
<223> OTHER INFORMATION: CTLA4(NEQ)-Ig(G2-ELLG-428L/434S) (XENP9524)

<400> SEQUENCE: 38

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
            35                  40                  45

Ala Ala Asn Tyr Met Met Gly Asn Glu Leu Thr Phe Glu Asp Asp Ser
50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Gln Val Glu Leu
                85                  90                  95

Met Tyr Pro Pro Pro Tyr Tyr Leu Gly Ile Gly Asn Gly Thr Gln Ile
                100                 105                 110

Tyr Val Ile Asp Pro Glu Pro Cys Pro Asp Ser Asp Gln Glu Pro Lys
            115                 120                 125

Ser Ser Asp Lys Thr His Thr Ser Pro Pro Ser Pro Ala Pro Glu Leu
130                 135                 140
```

```
Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
            165                 170                 175

Ser His Glu Asp Pro Glu Val Gln Phe Asn Trp Tyr Val Asp Gly Val
        180                 185                 190

Glu Val His Asn Ala Lys Thr Lys Pro Arg Glu Glu Gln Phe Asn Ser
    195                 200                 205

Thr Phe Arg Val Val Ser Val Leu Thr Val Val His Gln Asp Trp Leu
210                 215                 220

Asn Gly Lys Glu Tyr Lys Cys Lys Val Ser Asn Lys Gly Leu Pro Ala
225                 230                 235                 240

Pro Ile Glu Lys Thr Ile Ser Lys Thr Lys Gly Gln Pro Arg Glu Pro
            245                 250                 255

Gln Val Tyr Thr Leu Pro Pro Ser Arg Glu Glu Met Thr Lys Asn Gln
        260                 265                 270

Val Ser Leu Thr Cys Leu Val Lys Gly Phe Tyr Pro Ser Asp Ile Ala
    275                 280                 285

Val Glu Trp Glu Ser Asn Gly Gln Pro Glu Asn Asn Tyr Lys Thr Thr
290                 295                 300

Pro Pro Met Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
            325                 330                 335

Val Leu His Glu Ala Leu His Ser His Tyr Thr Gln Lys Ser Leu Ser
        340                 345                 350

Leu Ser Pro Gly Lys
        355

<210> SEQ ID NO 39
<211> LENGTH: 5
<212> TYPE: PRT
<213> ORGANISM: Artificial Sequence
<220> FEATURE:
<223> OTHER INFORMATION: glycine-serine polymer linker

<400> SEQUENCE: 39

Gly Ser Gly Gly Ser
1               5

<210> SEQ ID NO 40
<211> LENGTH: 5
<212> TYPE: PRT
<213> ORGANISM: Artificial Sequence
<220> FEATURE:
<223> OTHER INFORMATION: glycine-serine polymer linker

<400> SEQUENCE: 40

Gly Gly Gly Gly Ser
1               5

<210> SEQ ID NO 41
<211> LENGTH: 4
<212> TYPE: PRT
```

-continued

```
<213> ORGANISM: Artificial Sequence
<220> FEATURE:
<223> OTHER INFORMATION: glycine-serine polymer linker

<400> SEQUENCE: 41

Gly Gly Gly Ser
1
```